(12) United States Patent
Guzman et al.

(10) Patent No.: US 8,198,268 B2
(45) Date of Patent: Jun. 12, 2012

(54) TIANEPTINE SULFATE SALT FORMS AND METHODS OF MAKING AND USING THE SAME

(75) Inventors: Hector Guzman, Jamaica Plain, MA (US); Alexey Popov, Waltham, MA (US); Thomas J. L. Rammeloo, Vosselaar (BE); Julius Remenar, Framingham, MA (US); Jihad B. Saoud, Groton, MA (US); Mark Tawa, Acton, MA (US)

(73) Assignee: Janssen Biotech, Inc., Horsham, PA (US)

( * ) Notice: Subject to any disclaimer, the term of this patent is extended or adjusted under 35 U.S.C. 154(b) by 57 days.

(21) Appl. No.: 12/604,977

(22) Filed: Oct. 23, 2009

(65) Prior Publication Data
US 2010/0112051 A1    May 6, 2010

Related U.S. Application Data

(60) Provisional application No. 61/110,009, filed on Oct. 31, 2008, provisional application No. 61/110,006, filed on Oct. 31, 2008, provisional application No. 61/110,001, filed on Oct. 31, 2008, provisional application No. 61/228,343, filed on Jul. 24, 2009.

(51) Int. Cl.
*C07D 281/02*   (2006.01)
*A61K 31/554*   (2006.01)
*A61P 25/24*    (2006.01)

(52) U.S. Cl. .................. 514/211.13; 540/549
(58) Field of Classification Search ............. 540/549; 514/211.13
See application file for complete search history.

(56) References Cited

U.S. PATENT DOCUMENTS

| | | |
|---|---|---|
| 3,758,528 A | 9/1973 | Malen et al. |
| 4,139,834 A | 2/1979 | Matsui et al. |
| 5,888,542 A | 3/1999 | Huet de Barochez et al. |
| 5,922,341 A | 7/1999 | Smith et al. |
| 6,403,597 B1 | 6/2002 | Wilson et al. |
| 6,441,165 B2 | 8/2002 | Blanchard et al. |
| 6,495,154 B1 | 12/2002 | Tam et al. |
| 6,599,896 B1 | 7/2003 | Deslandes et al. |
| 6,682,072 B2 | 1/2004 | Horikoshi et al. |
| 6,683,072 B1 | 1/2004 | Kucharik et al. |
| 6,946,141 B2 | 9/2005 | Tam et al. |
| 7,070,765 B2 | 7/2006 | Rabinowitz et al. |
| 7,078,019 B2 | 7/2006 | Rabinowitz et al. |
| 2001/0008896 A1 | 7/2001 | Smith et al. |
| 2001/0037021 A1 | 11/2001 | Blanchard et al. |
| 2002/0037828 A1 | 3/2002 | Wilson et al. |
| 2002/0161016 A1 | 10/2002 | Tam et al. |
| 2003/0082214 A1 | 5/2003 | Williams et al. |
| 2003/0235631 A1 | 12/2003 | Sobolov-Jaynes et al. |
| 2004/0076648 A1 | 4/2004 | Williams et al. |
| 2004/0171682 A1 | 9/2004 | Del Soldato et al. |

(Continued)

FOREIGN PATENT DOCUMENTS

CN       1823785 A       8/2006
(Continued)

OTHER PUBLICATIONS

CN 101029336 A (English Abstract), (2007).
(Continued)

*Primary Examiner* — Bruck Kifle
(74) *Attorney, Agent, or Firm* — Kiera K. Mathey

(57) ABSTRACT

Disclosed herein is a novel sulfate salt of tianeptine with improved properties. Also described herein are novel pharmaceutical compositions comprising tianeptine sulfate salt, methods of making, and related methods of treatment.

30 Claims, 24 Drawing Sheets

U.S. PATENT DOCUMENTS

| | | |
|---|---|---|
| 2004/0191338 A1 | 9/2004 | Burch et al. |
| 2004/0242594 A1 | 12/2004 | Peters et al. |
| 2005/0203130 A1 | 9/2005 | Buntinx |
| 2005/0227961 A1 | 10/2005 | Kucharik et al. |
| 2005/0233010 A1 | 10/2005 | Satow |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0199805 A1 | 9/2006 | Pyke et al. |
| 2006/0211685 A1 | 9/2006 | Pyke et al. |
| 2006/0258715 A1 | 11/2006 | Jandura et al. |
| 2006/0258721 A1 | 11/2006 | Maddaford et al. |
| 2006/0270608 A1 | 11/2006 | Ongini et al. |
| 2007/0042969 A1 | 2/2007 | Rauschkolb-Loffler et al. |
| 2007/0043120 A1 | 2/2007 | Beyreuther et al. |
| 2007/0060550 A1 | 3/2007 | Mudge |
| 2007/0078162 A1 | 4/2007 | Buntinx |
| 2007/0116729 A1 | 5/2007 | Palepu |
| 2007/0161576 A1 | 7/2007 | Soldato et al. |
| 2007/0225279 A1 | 9/2007 | Rosenzweig-Lipson |
| 2007/0225379 A1 | 9/2007 | Carrara et al. |
| 2008/0014252 A1 | 1/2008 | DelPrete |
| 2008/0066739 A1 | 3/2008 | LeMahieu et al. |
| 2008/0066741 A1 | 3/2008 | LeMahieu et al. |
| 2008/0078382 A1 | 4/2008 | LeMahieu et al. |
| 2008/0107756 A1 | 5/2008 | Satow |
| 2008/0113950 A1 | 5/2008 | Soldato et al. |
| 2008/0214613 A1 | 9/2008 | Renton et al. |
| 2008/0221081 A1 | 9/2008 | Sansone |
| 2008/0234237 A1 | 9/2008 | Maddaford et al. |
| 2008/0249302 A1 | 10/2008 | Maddaford et al. |
| 2008/0269321 A1 | 10/2008 | Jandura et al. |

FOREIGN PATENT DOCUMENTS

| | | | |
|---|---|---|---|
| CN | 101029336 A | | 9/2007 |
| CN | 101292967 A | | 10/2008 |
| DE | 2011806 A1 | | 10/1970 |
| DE | 2011806 B2 | | 10/1970 |
| DE | 2011806 C3 | | 10/1970 |
| DE | 2065635 A1 | | 9/1974 |
| DE | 69706748 T2 | | 7/2002 |
| DE | 60100321 T2 | | 4/2004 |
| DE | 102004011392 A1 | | 8/2005 |
| DE | 60214476 T2 | | 5/2007 |
| EP | 0004516 A2 | | 10/1979 |
| EP | 0671173 A1 | | 9/1995 |
| EP | 0803253 A1 | | 10/1997 |
| EP | 0806202 A1 | | 11/1997 |
| EP | 0803253 B1 | | 9/2001 |
| EP | 1138677 A1 | | 10/2001 |
| EP | 1165089 A1 | | 1/2002 |
| EP | 1273301 A2 | | 1/2003 |
| EP | 1273301 A3 | | 5/2003 |
| EP | 1138677 B1 | | 6/2003 |
| EP | 1541197 A1 | | 6/2005 |
| EP | 1273301 B1 | | 9/2006 |
| EP | 1752143 A1 | | 2/2007 |
| EP | 1902742 A1 | | 3/2008 |
| EP | 1911481 A2 | | 4/2008 |
| EP | 1965778 A2 | | 9/2008 |
| FR | 2635461 A1 | | 2/1990 |
| FR | 2747921 A1 | | 10/1997 |
| FR | 2791891 A1 | | 10/2000 |
| FR | 2807039 A1 | | 10/2001 |
| FR | 2881350 A1 | | 8/2006 |
| FR | 2902337 A1 | | 12/2007 |
| GB | 1269551 | | 4/1972 |
| GB | 2442365 A | | 4/2008 |
| IN | 2005MU01013 A | | 6/2007 |
| IN | 2005MU01012 A | | 8/2007 |
| JP | 53005661 B | | 3/1978 |
| JP | 10036268 A | | 2/1998 |
| RU | 2176087 C1 | | 11/2001 |
| RU | 2270001 C1 | | 2/2006 |
| RU | 2271197 C2 | | 3/2006 |
| RU | 2296580 C1 | | 4/2007 |
| RU | 2304971 C2 | | 8/2007 |
| WO | WO 98/22114 A1 | | 5/1998 |
| WO | WO 99/63932 A2 | | 12/1999 |
| WO | WO 00/48636 A1 | | 8/2000 |
| WO | WO 00/59511 A1 | | 10/2000 |
| WO | WO 02/41883 A2 | | 5/2002 |
| WO | WO 03/000343 A2 | | 1/2003 |
| WO | WO 03/000642 A2 | | 1/2003 |
| WO | WO 03/015699 A2 | | 2/2003 |
| WO | WO 03/042162 A1 | | 5/2003 |
| WO | WO 03/105902 A1 | | 12/2003 |
| WO | WO 2004/010977 A1 | | 2/2004 |
| WO | WO 2004/054965 A1 | | 7/2004 |
| WO | WO 2004/056305 A2 | | 7/2004 |
| WO | WO 2004/069188 A2 | | 8/2004 |
| WO | WO 2005/053796 A1 | | 6/2005 |
| WO | WO 2005/067916 A1 | | 7/2005 |
| WO | WO 2005/084654 A2 | | 9/2005 |
| WO | WO 2005/099714 A1 | | 10/2005 |
| WO | WO 2005/102366 A2 | | 11/2005 |
| WO | WO 2006/082588 A2 | | 8/2006 |
| WO | WO 2006/096434 A2 | | 9/2006 |
| WO | WO 2006/096435 A1 | | 9/2006 |
| WO | WO 2006/102521 A2 | | 9/2006 |
| WO | WO 2006/116149 A1 | | 11/2006 |
| WO | WO 2007/017764 A2 | | 2/2007 |
| WO | WO 2007/017768 A2 | | 2/2007 |
| WO | WO 2007/061529 A1 | | 5/2007 |
| WO | WO 2007/063418 A2 | | 6/2007 |
| WO | WO 2007/100668 A2 | | 9/2007 |
| WO | WO 2007/112014 A2 | | 10/2007 |
| WO | WO 2007/137247 A2 | | 11/2007 |
| WO | WO 2007/141018 A1 | | 12/2007 |
| WO | WO 2008/036798 A2 | | 3/2008 |
| WO | WO 2008/036801 A2 | | 3/2008 |
| WO | WO 2008/100727 A2 | | 8/2008 |
| WO | WO 2008/103442 A1 | | 8/2008 |
| WO | WO 2008/112641 A2 | | 9/2008 |
| WO | WO 2008/116165 A2 | | 9/2008 |
| WO | WO 2008/116308 A1 | | 10/2008 |
| WO | WO 2009/021058 A2 | | 2/2009 |
| WO | WO 2009/029705 A1 | | 3/2009 |

OTHER PUBLICATIONS

CN 101292967 A (English Abstract), (2008).
CN 1823785 A (English Abstract), (2006).
DE 102004011392 A1 (English Abstract), (2005).
EP 0004516 A2 (English Abstract), (1979).
EP 0671173 A1 (English Abstract), (1995).
EP 0803253 A1, B1 (English Abstract), (1997).
EP 1138677 A1, B1 (English Abstract), (2001).
FR 2635461 A1 (English Abstract), (1990).
FR 2791891 A1 (English Abstract), (2000).
FR 2881350 A1 (English Abstract), (2006).
FR 2902337 A1 (English Abstract), (2007).
JP 10036268 A (English Abstract), (1998).
Porsolt et al., Behavioural Despair in Mice: A Primary Screening Test for Antidepressants, Arch. Int. Pharmacodyn., 229(2), 327-336, 1977.

TIANEPTINE SULFATE SALT FORMS AND METHODS OF MAKING AND USING THE SAME

CROSS-REFERENCE TO RELATED APPLICATIONS

This application claims the benefit of U.S. Provisional Application No. 61/110,009, filed Oct. 31, 2008, U.S. Provisional Application No. 61/110,006, filed Oct. 31, 2008, U.S. Provisional Application No. 61/110,001, filed Oct. 31, 2008, and U.S. Provisional Application No. 61/228,343, filed Jul. 24, 2009, the entire disclosures of which are hereby incorporated in their entirety.

FIELD OF THE INVENTION

The present invention relates to salts of tianeptine, particularly a novel sulfate salt of tianeptine with improved properties, more particularly tianeptine hemisulfate monohydrate. The invention also provides methods of using tianeptine sulfate salt in an oral dosage pharmaceutical composition and related methods of treatment with tianeptine sulfate salt.

BACKGROUND OF THE INVENTION

Tianeptine is a tricyclic compound with the chemical name 7-[(3-chloro-6,11-dihydro-6-methyldibenzo[c,f][1,2]thiazepin-11-yl)amino]heptanoic acid S,S-dioxide. Tianeptine is an antidepressant. The free form of tianeptine is amphoteric and an amorphous sodium salt is known in the art.

Synthesis of tianeptine and its sodium salt is disclosed in U.S. Pat. No. 3,758,528. Tianeptine sodium (i.e., STABLON®, Coaxil®, or Tatinol®) is currently approved in some countries in Europe, Latin America, Asia, and part of the Middle East for the treatment of one or more depressive disorders. Tianeptine sodium (i.e., STABLON®, Coaxil®, or Tatinol®) is rapidly and completely absorbed and has a short terminal half-life and effective treatment often requires dosing multiple times each day.

Presently, a pharmaceutical composition of tianeptine sodium is generally dosed orally up to three times a day. This frequent oral dosing may lead to decreased compliance with the recommended dosing regimen. A controlled release pharmaceutical composition of tianeptine should enable better command over the release profile and consequently, a less demanding dosing regimen. The sulfate salt of tianeptine may be advantageous in the preparation of a controlled release pharmaceutical composition comprising tianeptine.

BRIEF SUMMARY OF THE INVENTION

The present invention relates to a novel sulfate salt of tianeptine, particularly tianeptine hemisulfate monohydrate, with improved properties. Such improved properties can include, but are not limited to, hygroscopicity, physical stability, and solubility. The invention also provides novel pharmaceutical compositions comprising tianeptine sulfate salt, methods of making tianeptine sulfate salt, and related methods of treatment. For example, tianeptine hemisulfate monohydrate provides an alternative in a pharmaceutical composition to the currently marketed form, tianeptine sodium.

The free form of tianeptine has the following structure (I):

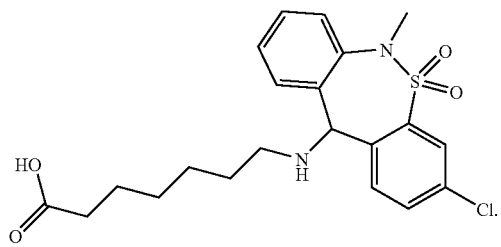

The sulfate salt of tianeptine can be used to provide pharmaceutical compositions for the treatment of conditions known in the art, such as one or more depressive disorders, irritable bowel syndrome (IBS), attention deficit hyperactivity disorder (ADHD), one or more neurodegenerative diseases, and asthma.

In some embodiments, the present invention provides 7-[(3-chloro-6,11-dihydro-6-methyldibenzo[c,f][1,2]thiazepin-11-yl)amino]heptanoic acid S,S-dioxide hemisulfate monohydrate, represented by formula (II):

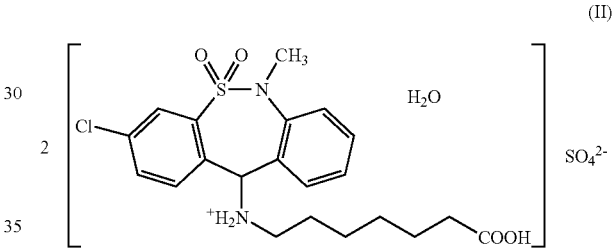

In some other embodiments, the present invention provides crystalline 7-[(3-chloro-6,11-dihydro-6-methyldibenzo[c,f][1,2]thiazepin-11-yl)amino]heptanoic acid S,S-dioxide hemisulfate monohydrate, characterized by an X-ray powder diffractogram including peaks at about 8.97, about 11.49, about 14.73, about 20.59, about 22.83 and about 23.27 degrees 2-theta.

In some other embodiments, the present invention provides a method of making 7-[(3-chloro-6,11-dihydro-6-methyldibenzo[c,f][1,2]thiazepin-11-yl)amino]heptanoic acid S,S-dioxide hemisulfate monohydrate of formula (II), including the steps of: (a) dissolving 7-[(3-chloro-6,11-dihydro-6-methyldibenzo[c,f][1,2]thiazepin-11-yl)amino]heptanoic acid S,S-dioxide or the sodium salt thereof in a mixture of water and acetic acid; (b) adding a solution of sulfuric acid in a solvent including water alone or in combination with acetic acid to the reaction mixture of step (a); and (c) crystallizing the compound of formula (II).

In still other embodiments, the present invention provides a controlled release matrix tablet including: a pharmaceutically effective amount of 7-[(3-chloro-6,11-dihydro-6-methyldibenzo[c,f][1,2]thiazepin-11-yl)amino]heptanoic acid S,S-dioxide hemisulfate monohydrate; and one or more release controlling polymers, wherein the tablet, when orally administered to a patient, provides a mean maximum plasma concentration ($C_{max}$) of 7-[(3-chloro-6,11-dihydro-6-methyldibenzo[c,f][1,2]thiazepin-11-yl)amino]heptanoic acid S,S-dioxide from about 100 ng/mL to about 150 ng/mL.

For a better understanding of the present invention, together with other and further embodiments thereof, reference is made to the accompanying drawings and detailed description.

DETAILED DESCRIPTION OF THE INVENTION

Figure 1:
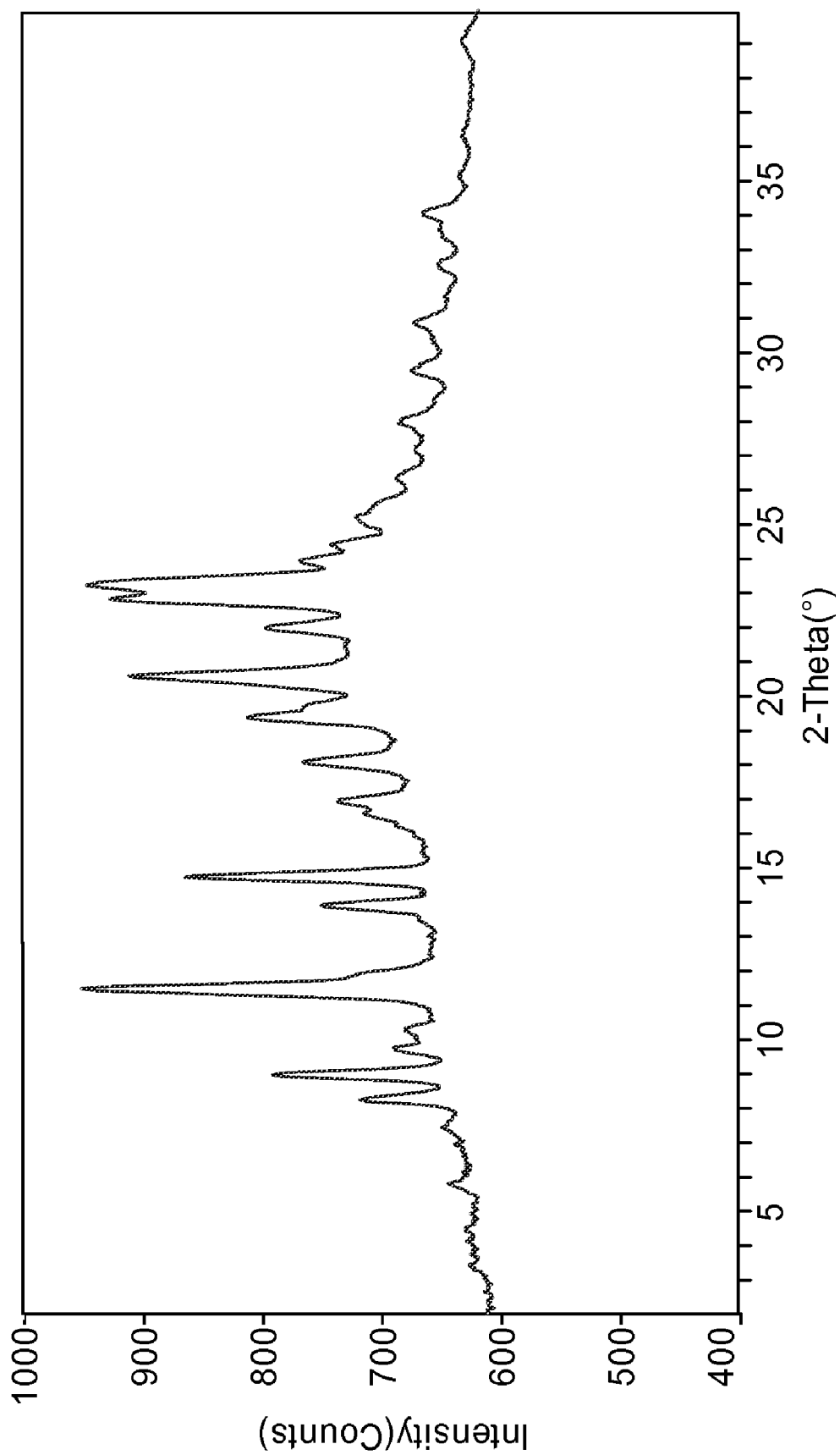
FIG. 1—PXRD diffractogram of tianeptine hemisulfate monohydrate
FIG. 2—DSC thermogram of tianeptine hemisulfate monohydrate
FIG. 3—TGA thermogram of tianeptine hemisulfate monohydrate
FIG. 4—DVS data of tianeptine hemisulfate monohydrate
FIG. 5—PXRD diffractogram of tianeptine hydrochloride
FIG. 6—DSC thermogram of tianeptine hydrochloride
FIG. 7—TGA thermogram of tianeptine hydrochloride
FIG. 8—DVS data of tianeptine hydrochloride
FIG. 9—PXRD diffractogram of tianeptine phosphate
FIG. 10—DSC thermogram of tianeptine phosphate
FIG. 11—TGA thermogram of tianeptine phosphate
FIG. 12—DVS data of tianeptine phosphate
FIG. 13—UV/visible spectrum of tianeptine hemisulfate monohydrate
FIG. 14—FTIR spectrum of tianeptine hemisulfate monohydrate
FIG. 15—Raman spectrum of tianeptine hemisulfate monohydrate
FIG. 16—DVS data of tianeptine sodium
FIG. 17—Solubility data of various tianeptine salts
FIG. 18—PXRD diffractogram of tianeptine Form II
FIG. 19—Solubility data of various tianeptine forms at 37° C. in various buffers
FIG. 20—Drug release from tablets prepared with tianeptine sodium salt and tianeptine hemisulfate monohydrate (in SGF)
FIG. 21—Drug release from tablets prepared with tianeptine sodium salt and tianeptine hemisulfate monohydrate (in SIF)
FIG. 22—Release rate from tablets prepared with tianeptine sodium salt and tianeptine hemisulfate monohydrate (in SGF)
FIG. 23—Release rate from tablets prepared with tianeptine sodium salt and tianeptine hemisulfate monohydrate (in logarithmic coordinates, in SGF)
FIG. 24—Linear mean plasma concentration-time profiles for STABLON® tablets as compared to tianeptine hemisulfate monohydrate tablets

The present invention relates to a novel sulfate salt of tianeptine, more particularly tianeptine hemisulfate monohydrate. The properties of the sulfate salt of tianeptine are improved relative to one or more known forms of tianeptine, such as tianeptine free base or tianeptine sodium (the currently available form of tianeptine). The sulfate salt can take several forms including, but not limited to, hydrates and solvates as well as various stoichiometric ratios of ionized tianeptine to sulfate counterion. The invention also includes other forms of tianeptine sulfate salt including, but not limited to, polymorphs, co-crystals, and amorphous forms. The invention also provides novel pharmaceutical compositions comprising these forms, methods of making these forms, and related methods of treatment.

All references to "tianeptine sulfate salt" herein also specifically refer to tianeptine hemisulfate monohydrate.

The salt of the present invention is a tianeptine sulfate salt. Tianeptine free base has the following structure (I):

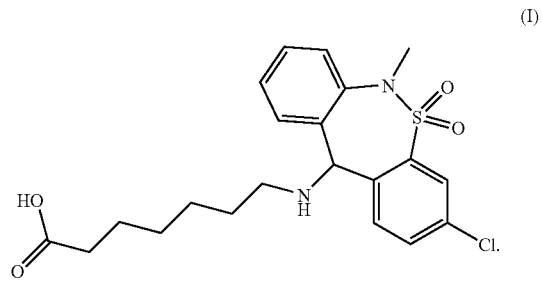

(I)

In a first embodiment, the present invention comprises tianeptine sulfate salt.

In a further embodiment, the sulfate salt of tianeptine can be incorporated into a pharmaceutical composition. In a further embodiment, the sulfate salt of tianeptine can be incorporated into a controlled release pharmaceutical composition.

In another embodiment, the sulfate salt of tianeptine can be incorporated into a pharmaceutical composition comprising two or more layers of tianeptine sulfate such that one layer is substantially released prior to the substantial release of another layer in vivo. In another embodiment, the sulfate salt of tianeptine can be incorporated into a pharmaceutical composition comprising pellets, wherein the pellets have varying extents or compositions of coating so as to enable release of tianeptine over a substantially longer period of time than that of the currently available tianeptine (e.g., STABLON®, Coaxil®, or Tatinol®).

In another embodiment, the sulfate salt of tianeptine can be incorporated into an osmotically active pharmaceutical composition suitable for oral administration. Osmotically active pharmaceutical compositions, osmotic pumps, osmotic drug delivery, and other osmotic technology suitable for oral administration can include, but are not limited to, OROS® Push-Pull and OROS® Tri-layer pharmaceutical compositions. In another embodiment, the sulfate salt of tianeptine can be incorporated into an OROS® drug delivery system. Such controlled release pharmaceutical compositions comprising the sulfate salt of tianeptine, such as an osmotically active pharmaceutical composition suitable for oral administration, may lead to a longer lasting therapeutic effect than that of tianeptine sodium salt in the currently marketed form.

In another embodiment, the present invention comprises tianeptine hemisulfate monohydrate. Tianeptine hemisulfate monohydrate has the following structure (II):

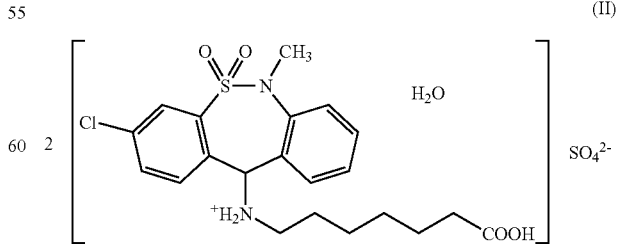

(II)

In some embodiments, the present invention is directed to tianeptine hemisulfate monohydrate in crystalline form.

In another embodiment, the tianeptine hemisulfate monohydrate is present, in at least a detectable amount, as crystalline tianeptine hemisulfate monohydrate. For instance, in some embodiments, the crystalline tianeptine hemisulfate monohydrate may be present in an amount of about 20% to about 100% by weight of the tianeptine hemisulfate monohydrate.

Figure 2:
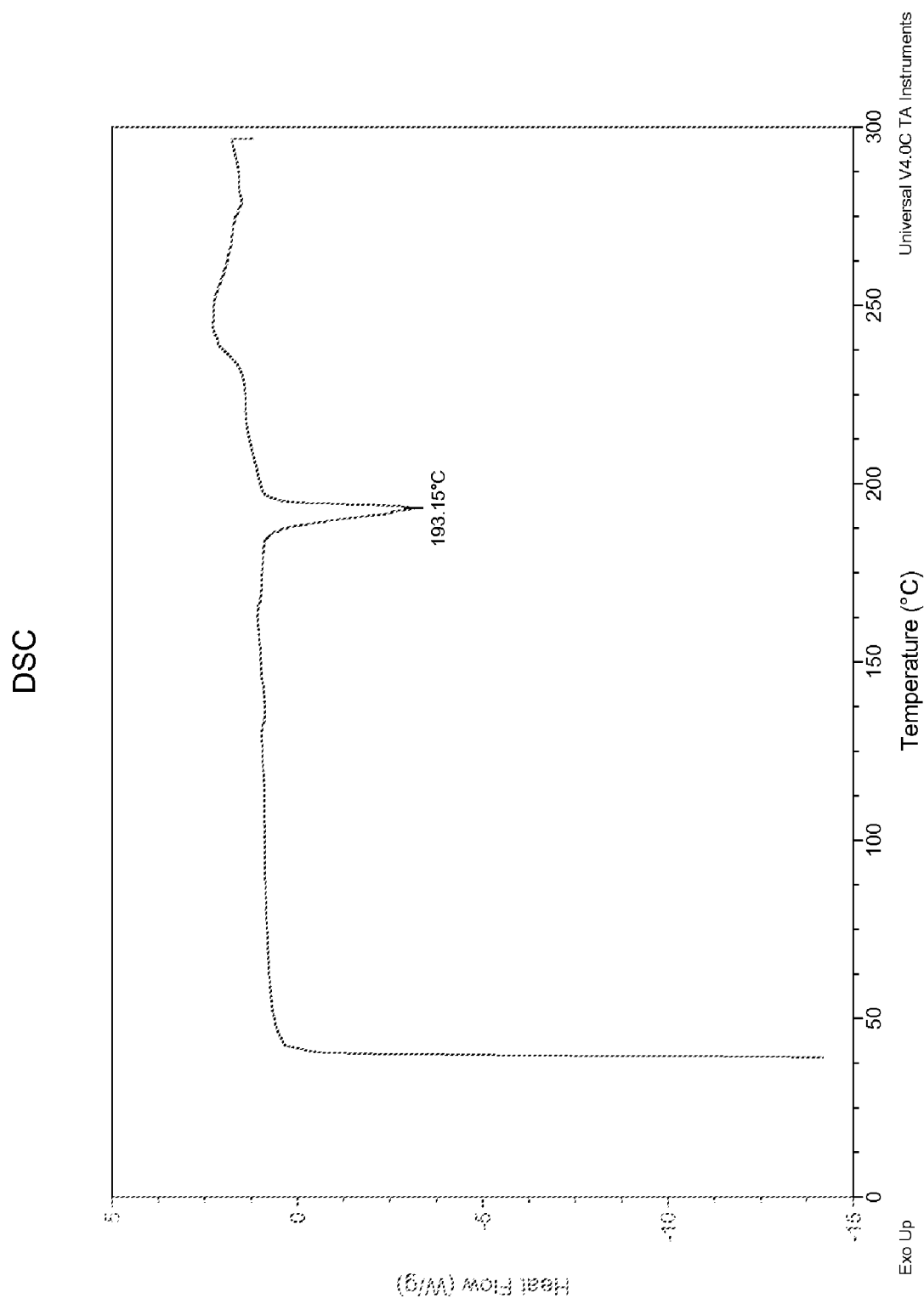
Figure 3:
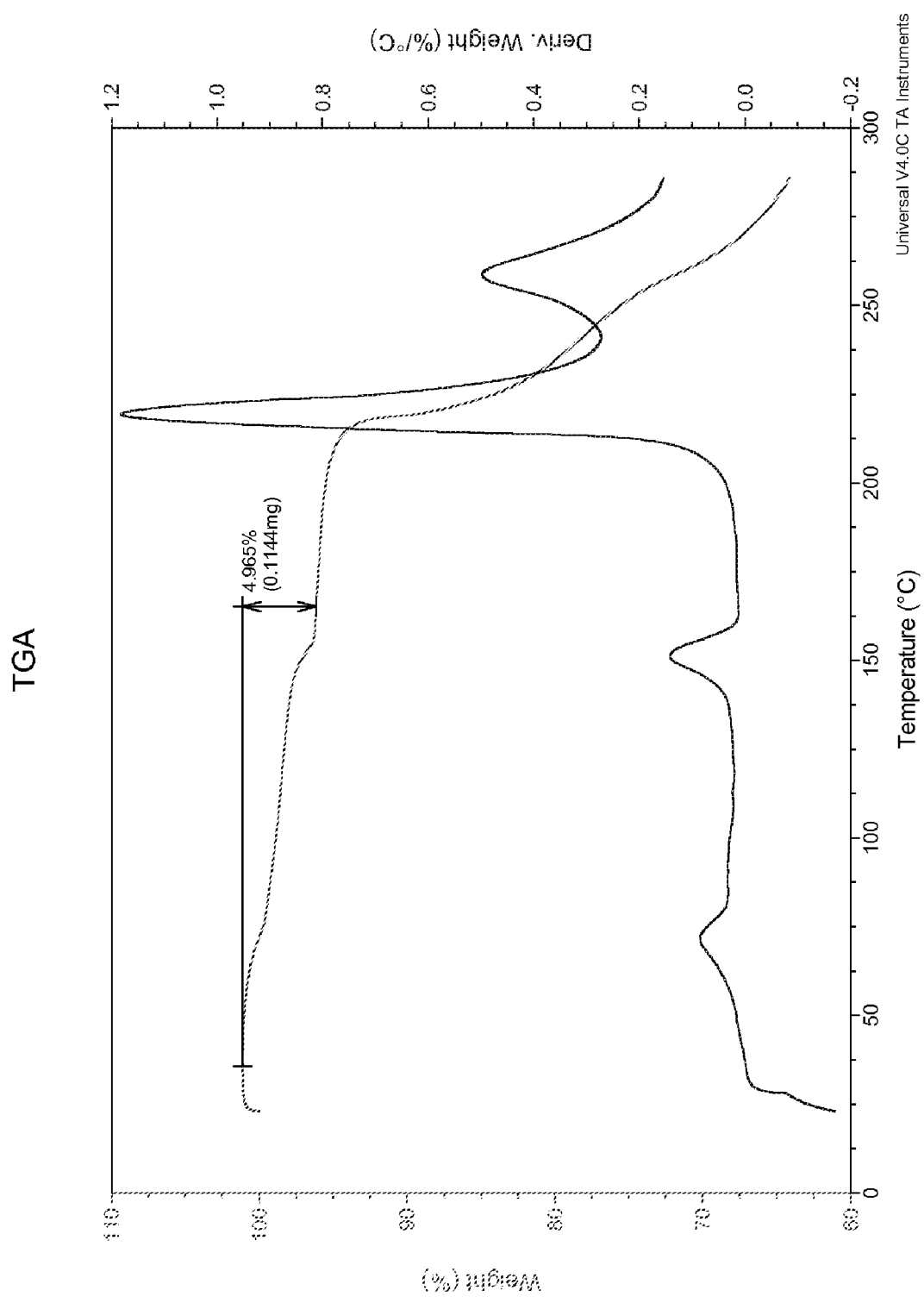

In another embodiment, the present invention comprises tianeptine hemisulfate monohydrate, wherein the hemisulfate monohydrate exhibits a PXRD diffractogram comprising a peak at about 8.97 degrees 2-theta. In another embodiment, the present invention comprises tianeptine hemisulfate monohydrate, wherein the hemisulfate monohydrate exhibits a PXRD diffractogram comprising a peak at about 8.25 degrees 2-theta. In another embodiment, the present invention comprises tianeptine hemisulfate monohydrate, wherein the hemisulfate monohydrate exhibits a PXRD diffractogram comprising a peak at about 11.49 degrees 2-theta. In another embodiment, the present invention comprises tianeptine hemisulfate monohydrate, wherein the hemisulfate monohydrate exhibits a PXRD diffractogram comprising peaks at about 8.25 and about 8.97 degrees 2-theta. In another embodiment, the present invention comprises tianeptine hemisulfate monohydrate, wherein the hemisulfate monohydrate exhibits a PXRD diffractogram comprising peaks at about 8.97 and about 11.49 degrees 2-theta. In another embodiment, the present invention comprises tianeptine hemisulfate monohydrate, wherein the hemisulfate monohydrate exhibits a PXRD diffractogram comprising peaks at about 13.91 and about 14.73 degrees 2-theta. In another embodiment, the present invention comprises tianeptine hemisulfate monohydrate, wherein the hemisulfate monohydrate exhibits a PXRD diffractogram comprising peaks at about 8.25, about 8.97, and about 11.49 degrees 2-theta. In another embodiment, the present invention comprises tianeptine hemisulfate monohydrate, wherein the hemisulfate monohydrate exhibits a PXRD diffractogram comprising peaks at about 8.97, about 14.73, about 18.07, and about 19.39 degrees 2-theta. In another embodiment, the present invention comprises tianeptine hemisulfate monohydrate, wherein the hemisulfate monohydrate exhibits a PXRD diffractogram comprising peaks at about 8.25, about 11.49, about 13.91, about 16.95, and about 20.59 degrees 2-theta. In another embodiment, the present invention comprises tianeptine hemisulfate monohydrate, wherein the hemisulfate monohydrate exhibits a PXRD diffractogram comprising peaks at about 16.95, about 18.07, about 19.39, and about 20.59 degrees 2-theta. In another embodiment, the present invention comprises tianeptine hemisulfate monohydrate, wherein the hemisulfate monohydrate exhibits a PXRD diffractogram comprising peaks at about 13.91, about 14.73, about 22.83, and about 23.27 degrees 2-theta. In another embodiment, the present invention comprises tianeptine hemisulfate monohydrate, wherein the hemisulfate monohydrate exhibits a PXRD diffractogram comprising peaks at about 8.25, about 8.97, about 11.49, about 13.91, and about 14.73 degrees 2-theta. In another embodiment, the present invention comprises tianeptine hemisulfate monohydrate, wherein the hemisulfate monohydrate exhibits a PXRD diffractogram comprising peaks at about 16.95, about 18.07, about 19.39, about 20.59, about 21.99, and about 23.27 degrees 2-theta. In another embodiment, the present invention comprises tianeptine hemisulfate monohydrate, wherein the hemisulfate monohydrate exhibits a PXRD diffractogram comprising peaks at about 8.25, about 8.97, about 11.49, about 13.91, about 14.73, about 16.95, about 18.07, about 19.39, about 20.59, about 21.99, about 22.83, and about 23.27 degrees 2-theta. In another embodiment, the present invention comprises tianeptine hemisulfate monohydrate, wherein the hemisulfate monohydrate exhibits a PXRD diffractogram comprising peaks at about 8.25, about 13.91, and about 14.73 degrees 2-theta. In another embodiment, the present invention comprises tianeptine hemisulfate monohydrate, wherein the hemisulfate monohydrate exhibits a PXRD diffractogram comprising peaks at about 8.97, about 18.07, about 19.39, and about 20.59 degrees 2-theta. In another embodiment, the present invention comprises tianeptine hemisulfate monohydrate, wherein the hemisulfate monohydrate exhibits a PXRD diffractogram comprising peaks at about 8.97, about 11.49, about 13.91, about 18.07, about 19.39 and about 20.59 degrees 2-theta. In another embodiment, the present invention comprises tianeptine hemisulfate monohydrate, wherein the hemisulfate monohydrate exhibits a PXRD diffractogram substantially similar to FIG. 1. In another embodiment, the present invention comprises tianeptine hemisulfate monohydrate, wherein the hemisulfate monohydrate exhibits a DSC thermogram comprising an endothermic transition at about 193 degrees C. In another embodiment, the present invention comprises tianeptine hemisulfate monohydrate, wherein the hemisulfate monohydrate exhibits a DSC thermogram substantially similar to FIG. 2. In another embodiment, the present invention comprises tianeptine hemisulfate monohydrate, wherein the hemisulfate monohydrate exhibits a TGA thermogram substantially similar to FIG. 3. In another embodiment, the present invention comprises tianeptine hemisulfate monohydrate, wherein the hemisulfate monohydrate exhibits dynamic vapor sorption (DVS) characteristics substantially similar to FIG. 4. In another embodiment, tianeptine hemisulfate monohydrate is incorporated into a controlled release pharmaceutical composition.

In another embodiment, the present invention comprises a tianeptine sulfate salt, wherein the sulfate salt is nonhygroscopic. In another embodiment, the present invention comprises a tianeptine sulfate salt, wherein the sulfate salt is nonhygroscopic from about 10% relative humidity to about 90% relative humidity. In another embodiment, the present invention comprises tianeptine hemisulfate monohydrate, wherein the hemisulfate monohydrate is nonhygroscopic from about 10% relative humidity to about 90% relative humidity as measured at 25 degrees C. by DVS. In another embodiment, the present invention comprises a tianeptine sulfate salt, wherein the sulfate salt is nonhygroscopic from about 20% relative humidity to about 80% relative humidity. In another embodiment, the present invention comprises a tianeptine sulfate salt, wherein the sulfate salt is nonhygroscopic from about 30% relative humidity to about 70% relative humidity. In another embodiment, the present invention comprises a tianeptine sulfate salt, wherein the sulfate salt is physically stable. In another embodiment, the present invention comprises a tianeptine sulfate salt, wherein the sulfate salt is physically stable from about 10% relative humidity to about 90% relative humidity. In another embodiment, the present invention comprises a tianeptine sulfate salt, wherein the sulfate salt is physically stable from about 20% relative humidity to about 80% relative humidity. In another embodiment, the present invention comprises a tianeptine sulfate salt, wherein the sulfate salt is physically stable from about 30% relative humidity to about 70% relative humidity.

According to the present invention, tianeptine sulfate salt can have various stoichiometric ratios of ionized tianeptine (cation) to sulfate counterion (anion). For example, the ratio of cation:anion can be about 1:1 or 2:1. Other stoichiometric ratios are also included in the invention. In some embodiments, tianeptine hemisulfate monohydrate comprises an about 2:1:2 ratio of ionized tianeptine to sulfuric acid to water.

In another embodiment, the present invention comprises tianeptine sulfate salt, and methods of making and using the same. In another embodiment, the present invention comprises a hydrate of tianeptine sulfate salt, and methods of making and using the same. In another embodiment, the present invention comprises a solvate of tianeptine sulfate salt. In another embodiment, the present invention comprises one or more polymorphs of tianeptine sulfate salt or one or more polymorphs of a hydrate or a solvate of tianeptine sulfate salt. In another embodiment, the present invention comprises a co-crystal of tianeptine sulfate salt. In another embodiment, the present invention comprises an amorphous form of tianeptine sulfate salt, and methods of making and using the same.

In another embodiment, a tianeptine sulfate salt form can exist in a form such as, but not limited to, an anhydrous form, a hydrate form, a dehydrate form, or a solvate form. Such hydrate and solvate forms can have various stoichiometric ratios of ionized tianeptine to water or solvate molecules such as, but not limited to, about 1:1, 1:1.5, 2:1, or 1:2.

In another embodiment, the present invention provides a method of making a sulfate salt of tianeptine, comprising:
(a) providing tianeptine or a sodium salt thereof; and
(b) contacting said tianeptine or a sodium salt thereof with sulfuric acid so as to crystallize said sulfate salt of tianeptine.

In a specific embodiment, said tianeptine is in the form of the sodium salt. In another embodiment, a solvent is added to said tianeptine or a sodium salt thereof prior to said sulfuric acid. In another embodiment, step (b) is completed in the presence of a solvent such that a solution is formed prior to crystallization of the sulfate salt. In another embodiment, step (b) is completed in the presence of a solvent such that a suspension is formed prior to crystallization of the sulfate salt. In certain embodiments, a solvent is selected from the group consisting of: acetone, ethanol, nitromethane, methanol, acetonitrile, dichloromethane, water, and tetrahydrofuran (THF). In another embodiment, a solvent comprises a mixture of any two or more solvents, including, but not limited to, acetone, ethanol, nitromethane, methanol, acetonitrile, dichloromethane, water, and tetrahydrofuran.

In another embodiment, the present invention provides a method of making tianeptine hemisulfate monohydrate, including the steps of:
(a) dissolving tianeptine or a sodium salt thereof in a mixture of water and acetic acid:
(b) adding a solution of sulfuric acid in a solvent comprising water alone or in combination with acetic acid to the reaction mixture of step (a); and
(c) crystallizing tianeptine hemisulfate monohydrate.

In some embodiments, the method may further include the steps of:
(d) isolating tianeptine hemisulfate monohydrate obtained in step (c) above from the reaction mixture;
(e) washing the tianeptine hemisulfate monohydrate with a mixture of water and acetic acid;
(f) further washing the tianeptine hemisulfate monohydrate with water; and
(g) drying the tianeptine hemisulfate monohydrate.

In some embodiments, the method is carried out without isolating an intermediate of the following formula:

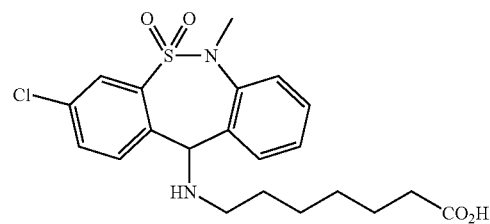

Tianeptine free base and tianeptine sodium can be prepared by one or more methods available in the art, including, but not limited to, the method in U.S. Pat. No. 3,758,528.

In one embodiment of the present invention, an amount of tianeptine sulfate salt effective to modulate a mammal's physiology and/or to treat a mammal is administered to said mammal. In one aspect, the tianeptine sulfate salt is administered in an amount sufficient to effect modulation of a mammal's physiology and/or treatment.

In another embodiment, a method of treating a mammal suffering from depression is provided, comprising administering to said mammal an effective amount of a tianeptine sulfate salt. In another embodiment, a method of treating a mammal suffering from irritable bowel syndrome is provided, comprising administering to said mammal an effective amount of a tianeptine sulfate salt. In another embodiment, a method of treating a mammal suffering from attention deficit hyperactivity disorder is provided, comprising administering to said mammal an effective amount of a tianeptine sulfate salt. In another embodiment, a method of treating a mammal suffering from asthma is provided, comprising administering to said mammal an effective amount of a tianeptine sulfate salt. In another embodiment, said mammal is a human.

In another embodiment, the present invention includes the preparation of a medicament comprising a sulfate salt of tianeptine. Such a medicament can be used for treating depression, irritable bowel syndrome, attention deficit hyperactivity disorder, one or more neurodegenerative diseases, or asthma, in a mammal in need of such treatment. In another embodiment, said mammal is a human.

Pharmaceutical dosage forms of tianeptine sulfate salt can be administered in several ways including, but not limited to, oral administration. Oral pharmaceutical compositions and dosage forms are exemplary dosage forms. Optionally, the oral dosage form is a solid dosage form, such as a tablet, a caplet, a hard gelatin capsule, a starch capsule, a hydroxypropyl methylcellulose (HPMC) capsule, or a soft elastic gelatin capsule. Tablets of the present invention may be made by any means known in the art. Conventional methods for tablet production include direct compression ("dry blending"), dry granulation followed by compression, and wet granulation followed by drying and compression. Other methods include the use of compacting roller technology such as a chilsonator or drop roller, or molding, casting, or extrusion technologies. All of these methods are known in the art, and are described in detail in, for example, Lachman, et al., "The Theory and Practice of Industrial Pharmacy," Chapter 11, (3$^{rd}$ Ed. 1986), which is incorporated by reference herein. Liquid dosage forms may also be provided by the present invention, including such non-limiting examples as a suspension, solution, syrup, or emulsion.

Tianeptine sulfate salt can be administered by controlled or delayed release means. Controlled release pharmaceutical products generally have a common goal of improving drug therapy over that achieved by their non-controlled release counterparts. Ideally, the use of an optimally designed controlled release preparation in medical treatment is characterized by a minimum of API (active pharmaceutical ingredient) substance being employed to cure or control the condition in a minimum amount of time. Advantages of controlled release pharmaceutical compositions generally include: 1) extended activity of the API; 2) reduced dosage frequency; 3) increased patient compliance; 4) usage of less total API; 5) reduction in local or systemic side effects; 6) minimization of API accumulation; 7) reduction in blood level fluctuations; 8) improvement in efficacy of treatment; 9) reduction of potentiation or loss of API activity; and 10) improvement in speed of control of diseases or conditions. (Kim, Cherng-ju, Controlled Release Dosage Form Design, 2 Technomic Publishing, Lancaster, Pa.: 2000).

In some embodiments, typical daily dosage forms of the invention comprise tianeptine sulfate salt, in an amount of from about 10.0 mg to about 50.0 mg, from about 12.5 mg to about 50.0 mg, from about 12.5 mg to 37.5 mg, or from about 25.0 mg to about 37.5 mg. In a particular embodiment, the tianeptine sulfate salt for use in such a composition is tianeptine hemisulfate monohydrate. The dosage amounts described herein are expressed in amounts of tianeptine free base and do not include the weight of a counterion (e.g., sulfate) or any water or solvent molecules.

In another embodiment of the invention, a pharmaceutical composition comprising tianeptine sulfate salt is administered orally as needed in an amount of from about 10.0 mg to about 50.0 mg, from about 12.5 mg to about 50.0 mg, from about 25.0 mg to about 50.0 mg, or from about 37.5 mg to about 50.0 mg tianeptine. For example, about 12.5 mg, about 25.0 mg, or about 37.5 mg. In specific embodiments, pharmaceutical compositions comprising tianeptine sulfate salt can be administered orally in amounts of about 25.0 mg or about 37.5 mg. The dosage amounts can be administered in single or divided doses. In some embodiments, the dosage form is administered one time per day. In some other embodiments, the dosage form is administered multiple times per day. In another embodiment, a daily dose of a pharmaceutical composition comprising tianeptine sulfate salt comprises up to about 50.0 mg tianeptine.

In some embodiments, daily dosage forms of the invention comprise tianeptine sulfate salt, in an amount of from about 25.0 mg to about 200.0 mg, from about 25.0 mg to about 150.0 mg, from about 25.0 mg to about 100.0 mg, or from about 25.0 mg to about 75.0 mg. In a particular embodiment, the tianeptine sulfate salt for use in such a composition is tianeptine hemisulfate monohydrate. The dosage amounts described herein are expressed in amounts of tianeptine free base and do not include the weight of a counterion (e.g., sulfate) or any water or solvent molecules.

In another embodiment of the invention, a pharmaceutical composition comprising tianeptine sulfate salt is administered orally as needed in an amount of from about 25.0 mg to about 200.0 mg, from about 25.0 mg to about 150.0 mg, from about 25.0 mg to about 100.0 mg, from about 25.0 mg to about 75.0 mg, or from about 50.0 mg to about 75.0 mg tianeptine. For example, about 25.0 mg, about 50.0 mg, or about 75.0 mg. In specific embodiments, pharmaceutical compositions comprising tianeptine sulfate salt can be administered orally in amounts of about 25.0 mg, about 50.0 mg, or about 75.0 mg. In another embodiment, a daily dose of a pharmaceutical composition comprising tianeptine sulfate salt comprises up to about 100.0 mg tianeptine.

In some embodiments, daily dosage forms of the invention comprise tianeptine sulfate salt, in an amount of from about 30.0 mg to about 200.0 mg, from about 30.0 mg to about 150.0 mg, from about 30.0 mg to about 100.0 mg, or from about 30.0 mg to about 60.0 mg. In a particular embodiment, the tianeptine sulfate salt for use in such a composition is tianeptine hemisulfate monohydrate. The dosage amounts described herein are expressed in amounts of tianeptine free base and do not include the weight of a counterion (e.g., sulfate) or any water or solvent molecules.

In another embodiment of the invention, a pharmaceutical composition comprising tianeptine sulfate salt is administered orally as needed in an amount of from about 30.0 mg to about 200.0 mg, from about 30.0 mg to about 150.0 mg, from about 30.0 mg to about 100.0 mg, or from about 30.0 mg to about 60.0 mg tianeptine. For example, about 30.0 mg, about 60.0 mg, or about 100.0 mg. In specific embodiments, pharmaceutical compositions comprising tianeptine sulfate salt can be administered orally in amounts of about 30.0 mg, about 60.0 mg, or about 100.0 mg. In another embodiment, a daily dose of a pharmaceutical composition comprising tianeptine sulfate salt comprises up to about 100.0 mg tianeptine.

In some embodiments, typical daily dosage forms of the invention comprise tianeptine sulfate salt, in an amount of from about 10 mg to about 50 mg, from about 12.5 mg to about 50 mg, from about 12.5 mg to about 37.5 mg, or from about 25 mg to about 37.5 mg. In a particular embodiment, the tianeptine sulfate salt for use in such a composition is tianeptine hemisulfate monohydrate. The dosage amounts described herein are expressed in amounts of tianeptine free base and do not include the weight of a counterion (e.g., sulfate) or any water or solvent molecules.

In another embodiment of the invention, a pharmaceutical composition comprising tianeptine sulfate salt is administered orally as needed in an amount of from about 10 mg to about 50 mg, from about 12.5 mg to about 50 mg, from about 25 mg to about 50 mg, or from about 37.5 mg to about 50 mg tianeptine. For example, about 12.5 mg, about 25 mg, or about 37.5 mg. In specific embodiments, pharmaceutical compositions comprising tianeptine sulfate salt can be administered orally in amounts of about 25 mg or about 37.5 mg. The dosage amounts can be administered in single or divided doses. In another embodiment, a daily dose of a pharmaceutical composition comprising tianeptine sulfate salt comprises up to about 50 mg tianeptine.

In some embodiments, daily dosage forms of the invention comprise tianeptine sulfate salt, in an amount of from about 25 mg to about 200 mg, from about 25 mg to about 150 mg, from about 25 mg to about 100 mg, or from about 25 mg to about 75 mg. In a particular embodiment, the tianeptine sulfate salt for use in such a composition is tianeptine hemisulfate monohydrate. The dosage amounts described herein are expressed in amounts of tianeptine free base and do not include the weight of a counterion (e.g., sulfate) or any water or solvent molecules.

In another embodiment of the invention, a pharmaceutical composition comprising tianeptine sulfate salt is administered orally as needed in an amount of from about 25 mg to about 200 mg, from about 25 mg to about 150 mg, from about 25 mg to about 100 mg, from about 25 mg to about 75 mg, or from about 50 mg to about 75 mg tianeptine. For example, about 25 mg, about 50 mg, or about 75 mg. In specific embodiments, pharmaceutical compositions comprising tianeptine sulfate salt can be administered orally in amounts of about 25 mg, about 50 mg, or about 75 mg. In another embodiment, a daily dose of a pharmaceutical composition comprising tianeptine sulfate salt comprises up to about 100 mg tianeptine.

In some embodiments, daily dosage forms of the invention comprise tianeptine sulfate salt, in an amount of from about 30 mg to about 200 mg, from about 30 mg to about 150 mg, from about 30 mg to about 100 mg, or from about 30 mg to about 60 mg. In a particular embodiment, the tianeptine sulfate salt for use in such a composition is tianeptine hemisulfate monohydrate. The dosage amounts described herein are expressed in amounts of tianeptine free base and do not include the weight of a counterion (e.g., sulfate) or any water or solvent molecules.

In another embodiment of the invention, a pharmaceutical composition comprising tianeptine sulfate salt is administered orally as needed in an amount of from about 30 mg to about 200 mg, from about 30 mg to about 150 mg, from about 30 mg to about 100 mg, or from about 30 mg to about 60 mg tianeptine. For example, about 30 mg, about 60 mg, or about 100 mg. In specific embodiments, pharmaceutical compositions comprising tianeptine sulfate salt can be administered orally in amounts of about 30 mg, about 60 mg, or about 100 mg. In another embodiment, a daily dose of a pharmaceutical composition comprising tianeptine sulfate salt comprises up to about 100 mg tianeptine.

In other embodiments, the present invention is directed to compositions comprising tianeptine sulfate salt as described herein and one or more diluents, carriers, and/or excipients suitable for the administration to a mammal for the treatment or prevention of one or more of the conditions described herein. In some embodiments, a pharmaceutical composition includes tianeptine hemisulfate monohydrate and a pharmaceutically acceptable carrier. In some embodiments, the pharmaceutical composition is a controlled release pharmaceutical composition. In one embodiment, a controlled release pharmaceutical composition of tianeptine sulfate requires a less complex mixture of excipients than other pharmaceutical compositions comprising another form of tianeptine.

The tianeptine sulfate salt of the present invention may also be used to prepare pharmaceutical dosage forms other than the oral dosage forms described above, such as topical dosage forms, parenteral dosage forms, transdermal dosage forms, and mucosal dosage forms. For example, such forms include creams, lotions, solutions, suspensions, emulsions, ointments, powders, patches, suppositories, and the like.

In other embodiments, the present invention is directed to a controlled release matrix tablet including a pharmaceutically effective amount of tianeptine sulfate salt, particularly tianeptine hemisulfate monohydrate, and one or more release controlling polymers, wherein the tablet, when orally administered to a patient, provides a mean maximum plasma concentration ($C_{max}$) of tianeptine from about 100 ng/mL to about 150 ng/mL. In some embodiments, the tablet, when orally administered to a patient, provides a mean maximum plasma concentration ($C_{max}$) of tianeptine from about 100 ng/mL to about 120 ng/mL. The tablet may include a 25 mg dose of tianeptine.

In some embodiments, the controlled release matrix tablet has a dissolution rate in vitro, when measured using a USP dissolution apparatus, type II (paddle) at 100 rpm in 900 mL simulated gastric fluid (pH about 1.2) at about 37° C., of less than 14% tianeptine hemisulfate monohydrate released after 1 hour, between 45% and 80% tianeptine hemisulfate monohydrate released after 7 hours, and greater than 90% tianeptine hemisulfate monohydrate released after 16 hours, by weight.

In some other embodiments, the controlled release matrix tablet has a dissolution rate in vitro, when measured using a USP dissolution apparatus, type II (paddle) at 100 rpm in 900 mL simulated gastric fluid (pH about 1.2) at about 37° C., of less than 20% tianeptine hemisulfate monohydrate released after 2 hours, between 50% and 80% tianeptine hemisulfate monohydrate released after 8 hours, and greater than 90% tianeptine hemisulfate monohydrate released after 14 hours, by weight.

In some embodiments, the tablet, when orally administered to a patient, provides a median time to mean maximum plasma concentration ($T_{max}$) of tianeptine ranging from about 2.5 hours to about 3.0 hours. In some embodiments, the tablet, when orally administered to a patient, provides a plasma concentration time curve with a mean area under the curve ranging from about 1170 ng.hr/mL to about 1380 ng.hr/mL. The tablet may include a 25 mg dose of tianeptine.

In some embodiments, the one or more release controlling polymers contained in the tablet includes cellulosic polymers, such as, but not limited to, hydroxypropyl methylcellulose. More specifically, the one or more release controlling polymers may include a first hydroxypropyl methylcellulose having a viscosity of 80 to 120 cps (2% solution in water) and a second hydroxypropyl methylcellulose having a viscosity of 3,000 to 5,600 cps (2% solution in water). In some embodiments, the first hydroxypropyl methylcellulose and the second hydroxypropyl methylcellulose are present in a ratio of about 2:1 to about 4:1.

In some embodiments, the controlled release matrix tablet further includes a filler, such as, for example, microcrystalline cellulose. The tablet also may further include a lubricant, such as, for example, magnesium stearate. In some embodiments, the tablet also may further include colloidal silica.

The tianeptine sulfate salt forms of the present invention can be characterized, e.g., by the TGA, DSC, DVS, single crystal x-ray diffractometer data, or by any one, any two, any three, any four, any five, any six, any seven, any eight, any nine, any ten, or any single integer number of PXRD 2-theta angle peaks, or by any combination of the data acquired from the analytical techniques described herein.

The present invention also relates to a novel hydrochloride salt of tianeptine. The properties of the hydrochloride salt of tianeptine are improved relative to one or more known forms of tianeptine, such as tianeptine free base or tianeptine sodium (the currently available form of tianeptine). The hydrochloride salt can take several forms including, but not limited to, hydrates and solvates as well as various stoichiometric ratios of ionized tianeptine to chloride counterion. The invention also includes other forms of tianeptine hydrochloride salt including, but not limited to, polymorphs, co-crystals, and amorphous forms. The invention also provides novel pharmaceutical compositions comprising these forms, methods of making these forms, and related methods of treatment.

In one embodiment, the present invention comprises tianeptine hydrochloride salt.

In a further embodiment, the hydrochloride salt of tianeptine can be incorporated into a pharmaceutical composition. In a further embodiment, the hydrochloride salt of tianeptine can be incorporated into a controlled release pharmaceutical composition.

In another embodiment, the hydrochloride salt of tianeptine can be incorporated into a pharmaceutical composition comprising two or more layers of tianeptine hydrochloride such that one layer is substantially released prior to the substantial release of another layer in vivo. In another embodiment, the hydrochloride salt of tianeptine can be incorporated into a pharmaceutical composition comprising pellets, wherein the pellets have varying extents or compositions of coating so as to enable release of tianeptine over a substantially longer period of time than that of the currently available tianeptine (e.g., STABLON®).

In another embodiment, the hydrochloride salt of tianeptine can be incorporated into an osmotically active pharmaceutical composition suitable for oral administration. Osmotically active pharmaceutical compositions, osmotic pumps, osmotic drug delivery, and other osmotic technology suitable for oral administration can include, but are not limited to, OROS® Push-Pull and OROS® Tri-layer pharmaceutical compositions. In another embodiment, the hydrochloride salt of tianeptine can be incorporated into an OROS® drug delivery system. Such controlled release pharmaceutical compositions comprising the hydrochloride salt of tianeptine, such as an osmotically active pharmaceutical composition suitable for oral administration, may lead to a longer lasting therapeutic effect than that of tianeptine sodium salt in the currently marketed form.

Figure 5:
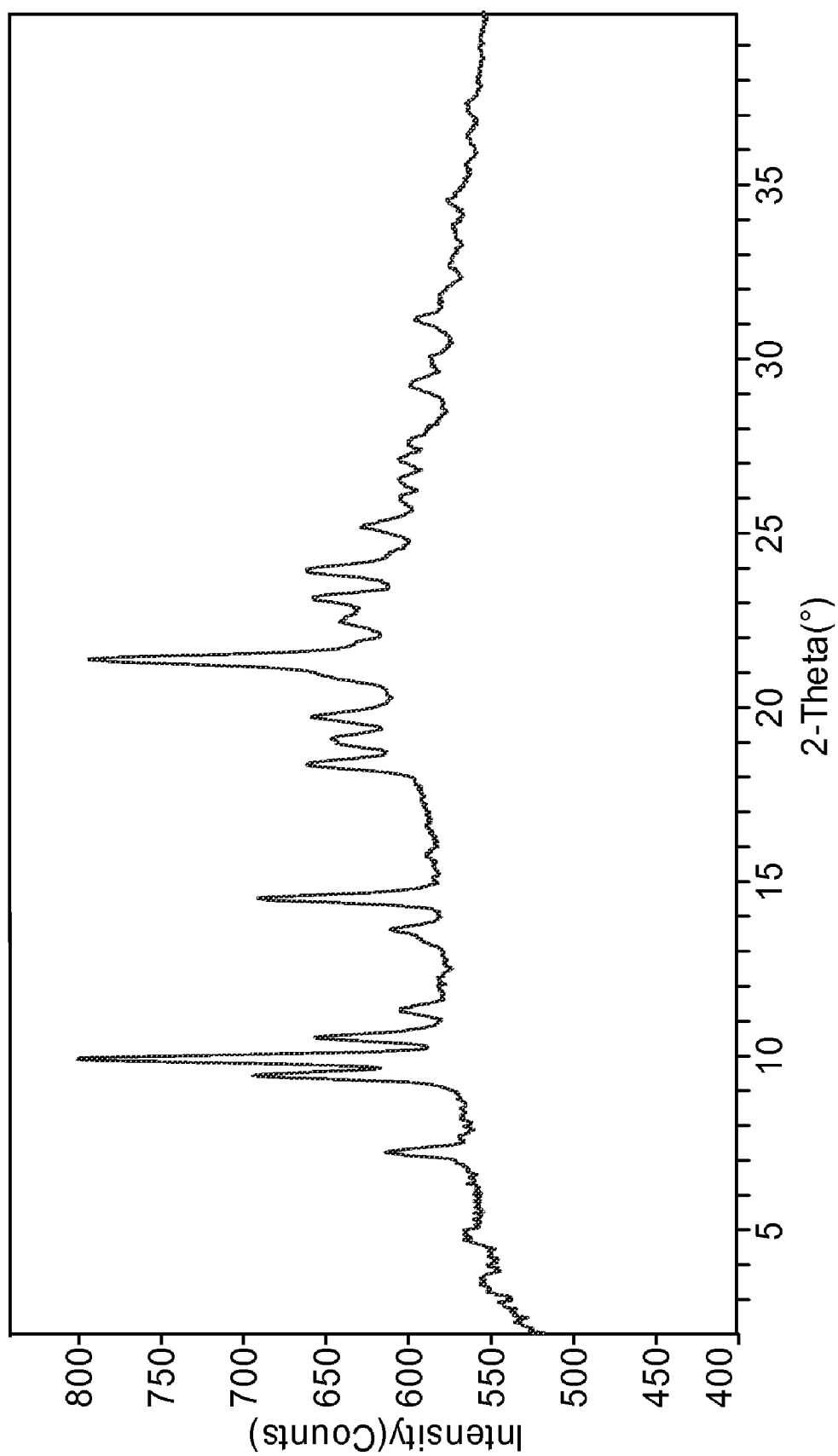
Figure 6:
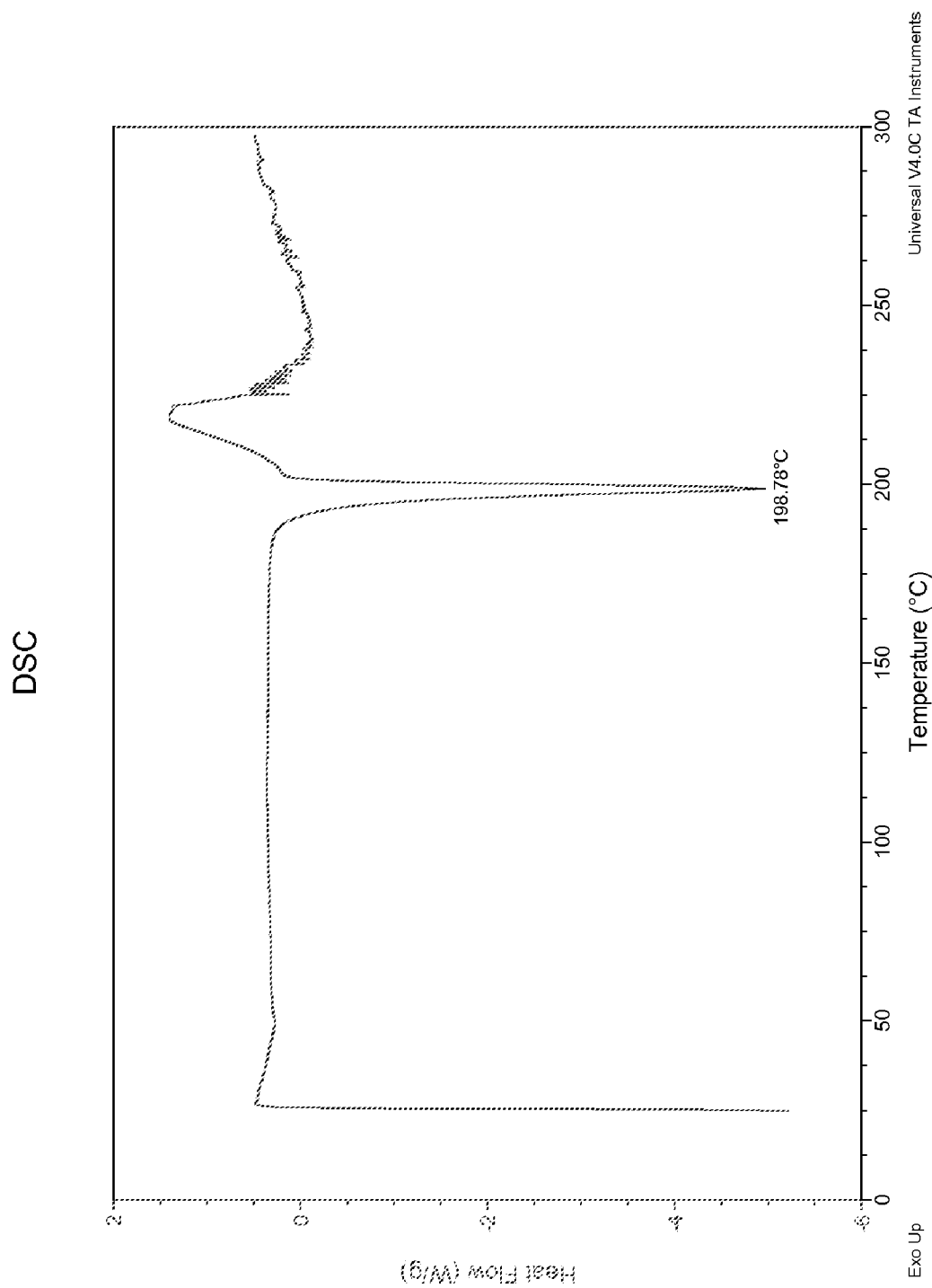
Figure 7:
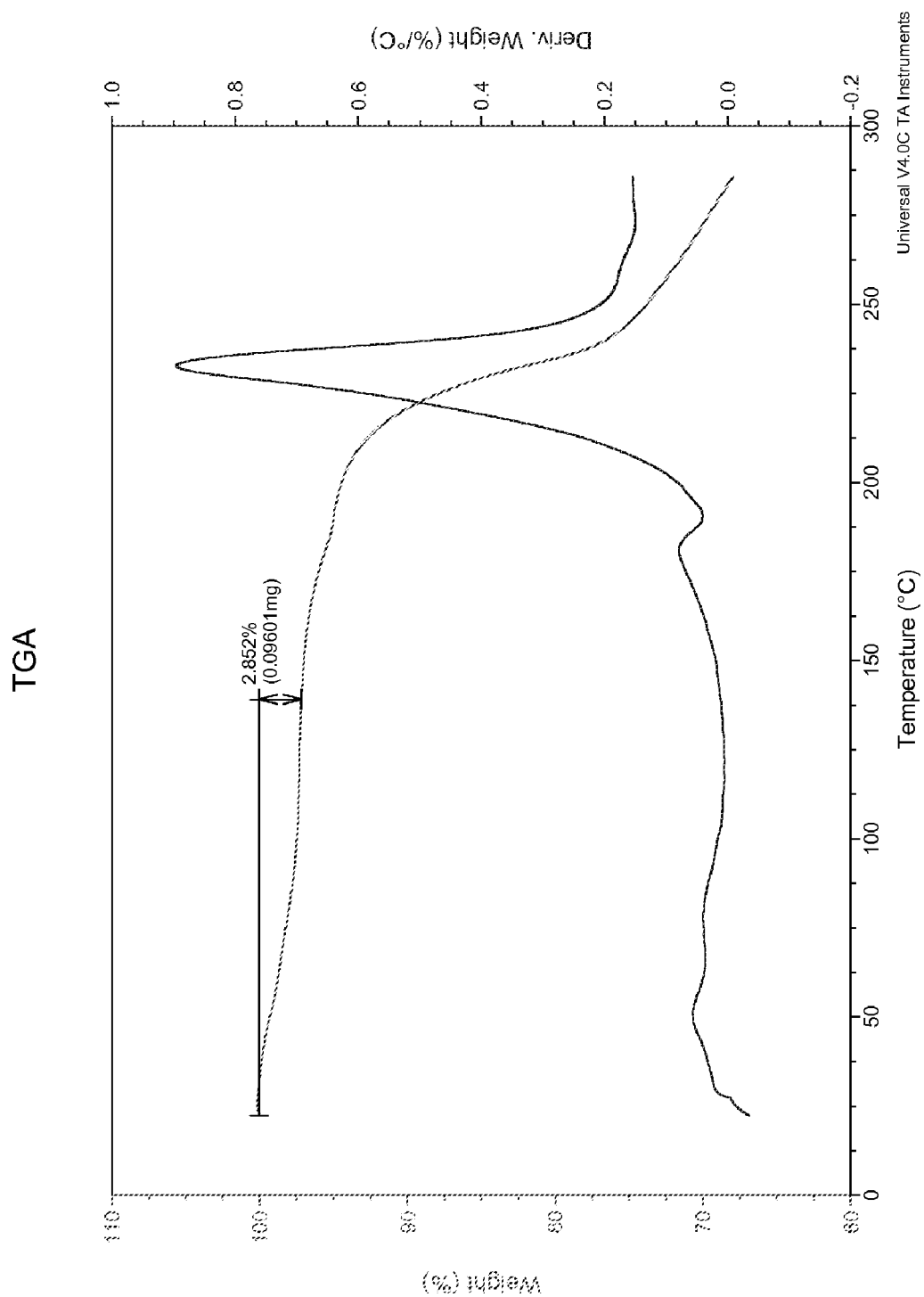
Figure 8:
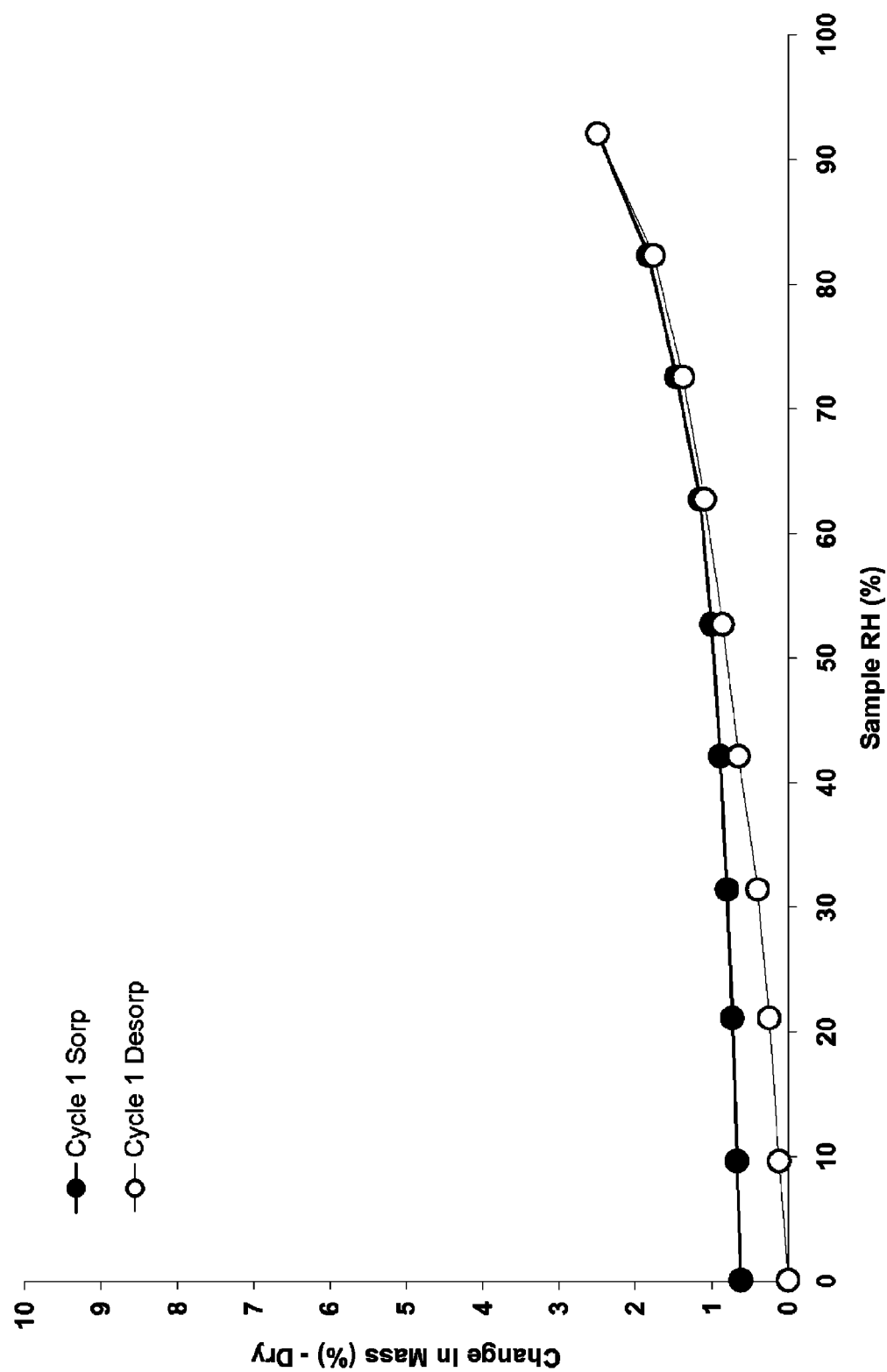

In another embodiment, the present invention comprises tianeptine hydrochloride. In another embodiment, the present invention comprises tianeptine hydrochloride, wherein the hydrochloride exhibits a PXRD diffractogram comprising a peak at about 7.23 degrees 2-theta. In another embodiment, the present invention comprises tianeptine hydrochloride, wherein the hydrochloride exhibits a PXRD diffractogram comprising a peak at about 9.91 degrees 2-theta. In another embodiment, the present invention comprises tianeptine hydrochloride, wherein the hydrochloride exhibits a PXRD diffractogram comprising a peak at about 14.53 degrees 2-theta. In another embodiment, the present invention comprises tianeptine hydrochloride, wherein the hydrochloride exhibits a PXRD diffractogram comprising peaks at about 7.23 and about 9.91 degrees 2-theta. In another embodiment, the present invention comprises tianeptine hydrochloride, wherein the hydrochloride exhibits a PXRD diffractogram comprising peaks at about 9.43 and about 14.53 degrees 2-theta. In another embodiment, the present invention comprises tianeptine hydrochloride, wherein the hydrochloride exhibits a PXRD diffractogram comprising peaks at about 7.23 and about 10.53 degrees 2-theta. In another embodiment, the present invention comprises tianeptine hydrochloride, wherein the hydrochloride exhibits a PXRD diffractogram comprising peaks at about 7.23, about 9.91, and about 14.53 degrees 2-theta. In another embodiment, the present invention comprises tianeptine hydrochloride, wherein the hydrochloride exhibits a PXRD diffractogram comprising peaks at about 9.43, about 10.53, about 14.53, and about 18.35 degrees 2-theta. In another embodiment, the present invention comprises tianeptine hydrochloride, wherein the hydrochloride exhibits a PXRD diffractogram comprising peaks at about 7.23, about 9.91, about 18.35, about 21.39, and about 23.93 degrees 2-theta. In another embodiment, the present invention comprises tianeptine hydrochloride, wherein the hydrochloride exhibits a PXRD diffractogram comprising peaks at about 9.91, about 14.53, about 18.35, and about 21.39 degrees 2-theta. In another embodiment, the present invention comprises tianeptine hydrochloride, wherein the hydrochloride exhibits a PXRD diffractogram comprising peaks at about 7.23, about 9.43, about 10.53, and about 18.35 degrees 2-theta. In another embodiment, the present invention comprises tianeptine hydrochloride, wherein the hydrochloride exhibits a PXRD diffractogram comprising peaks at about 9.43, about 9.91, about 10.53, about 14.53, and about 21.39 degrees 2-theta. In another embodiment, the present invention comprises tianeptine hydrochloride, wherein the hydrochloride exhibits a PXRD diffractogram comprising peaks at about 7.23, about 10.53, about 14.53, about 18.35, about 21.39, and about 23.93 degrees 2-theta. In another embodiment, the present invention comprises tianeptine hydrochloride, wherein the hydrochloride exhibits a PXRD diffractogram comprising peaks at about 7.23, about 9.43, about 9.91, about 10.53, about 14.53, about 18.35, about 21.39, and about 23.93 degrees 2-theta. In another embodiment, the present invention comprises tianeptine hydrochloride, wherein the hydrochloride exhibits a PXRD diffractogram substantially similar to FIG. 5. In another embodiment, the present invention comprises tianeptine hydrochloride, wherein the hydrochloride exhibits a DSC thermogram comprising an endothermic transition at about 199 degrees C. In another embodiment, the present invention comprises tianeptine hydrochloride, wherein the hydrochloride exhibits a DSC thermogram substantially similar to FIG. 6. In another embodiment, the present invention comprises tianeptine hydrochloride, wherein the hydrochloride exhibits a TGA thermogram substantially similar to FIG. 7. In another embodiment, the present invention comprises tianeptine hydrochloride, wherein the hydrochloride exhibits dynamic vapor sorption (DVS) characteristics substantially similar to FIG. 8. In another embodiment, tianeptine hydrochloride is incorporated into a controlled release pharmaceutical composition.

In another embodiment, the present invention comprises a tianeptine hydrochloride salt, wherein the hydrochloride salt is nonhygroscopic. In another embodiment, the present invention comprises a tianeptine hydrochloride salt, wherein the hydrochloride salt is nonhygroscopic from about 10% relative humidity to about 90% relative humidity. In another embodiment, the present invention comprises a tianeptine hydrochloride salt, wherein the hydrochloride salt is nonhygroscopic from about 20% relative humidity to about 80% relative humidity. In another embodiment, the present invention comprises a tianeptine hydrochloride salt, wherein the hydrochloride salt is nonhygroscopic from about 30% relative humidity to about 70% relative humidity. In another embodiment, the present invention comprises a tianeptine hydrochloride salt, wherein the hydrochloride salt is physically stable. In another embodiment, the present invention comprises a tianeptine hydrochloride salt, wherein the hydrochloride salt is physically stable from about 10% relative humidity to about 90% relative humidity. In another embodiment, the present invention comprises a tianeptine hydrochloride salt, wherein the hydrochloride salt is physically stable from about 20% relative humidity to about 80% relative humidity. In another embodiment, the present invention comprises a tianeptine hydrochloride salt, wherein the hydrochloride salt is physically stable from about 30% relative humidity to about 70% relative humidity.

According to the present invention, tianeptine hydrochloride salt can have various stoichiometric ratios of ionized tianeptine (cation) to chloride counterion (anion). For example, the ratio of cation:anion can be about 1:1 or 2:1. Other stoichiometric ratios are also included in the invention.

In another embodiment, the present invention comprises tianeptine hydrochloride salt, and methods of making and using the same. In another embodiment, the present invention comprises a hydrate of tianeptine hydrochloride salt. In another embodiment, the present invention comprises a solvate of tianeptine hydrochloride salt. In another embodiment, the present invention comprises one or more polymorphs of tianeptine hydrochloride salt or one or more polymorphs of a hydrate or a solvate of tianeptine hydrochloride salt. In another embodiment, the present invention comprises a co-crystal of tianeptine hydrochloride salt. In another embodiment, the present invention comprises an amorphous form of tianeptine hydrochloride salt, and methods of making and using the same.

In another embodiment, a tianeptine hydrochloride salt form can exist in a form such as, but not limited to, an anhydrous form, a hydrate form, or a solvate form. Such hydrate and solvate forms can have various stoichiometric ratios of ionized tianeptine to water or solvate molecules such as, but not limited to, about 1:1, 1:1.5, 2:1, or 1:2.

In another embodiment, the present invention provides a method of making a hydrochloride salt of tianeptine, comprising:

(c) providing tianeptine or a sodium salt thereof; and
(d) contacting said tianeptine or a sodium salt thereof with hydrochloric acid so as to crystallize said hydrochloride salt of tianeptine.

In a specific embodiment, said tianeptine is in the form of the sodium salt. In another embodiment, a solvent is added to said tianeptine or a sodium salt thereof prior to said hydrochloric acid. In another embodiment, step (b) is completed in the presence of a solvent such that a solution is formed prior to crystallization of the hydrochloride salt. In another embodiment, step (b) is completed in the presence of a solvent such that a suspension is formed prior to crystallization of the hydrochloride salt. In certain embodiments, a solvent is selected from the group consisting of: acetone, ethanol, nitromethane, methanol, acetonitrile, dichloromethane, water, and tetrahydrofuran (THF). In another embodiment, a solvent comprises a mixture of any two or more solvents, including, but not limited to, acetone, ethanol, nitromethane, methanol, acetonitrile, dichloromethane, water, and tetrahydrofuran.

Tianeptine free base and tianeptine sodium can be prepared by one or more methods available in the art, including, but not limited to, the method in U.S. Pat. No. 3,758,528.

In one embodiment of the present invention, an amount of tianeptine hydrochloride salt effective to modulate a mammal's physiology and/or to treat a mammal is administered to said mammal. In one aspect, the tianeptine hydrochloride salt is administered in an amount sufficient to effect modulation of a mammal's physiology and/or treatment.

In another embodiment, a method of treating a mammal suffering from depression is provided, comprising administering to said mammal an effective amount of a tianeptine hydrochloride salt. In another embodiment, a method of treating a mammal suffering from irritable bowel syndrome is provided, comprising administering to said mammal an effective amount of a tianeptine hydrochloride salt. In another embodiment, a method of treating a mammal suffering from attention deficit hyperactivity disorder is provided, comprising administering to said mammal an effective amount of a tianeptine hydrochloride salt. In another embodiment, a method of treating a mammal suffering from asthma is provided, comprising administering to said mammal an effective amount of a tianeptine hydrochloride salt. In another embodiment, said mammal is a human.

In another embodiment, the present invention includes the preparation of a medicament comprising a hydrochloride salt of tianeptine. Such a medicament can be used for treating depression, irritable bowel syndrome, attention deficit hyperactivity disorder, or asthma, in a mammal in need of such treatment. In another embodiment, said mammal is a human.

Pharmaceutical dosage forms of tianeptine hydrochloride salt can be administered in several ways including, but not limited to, oral administration. Oral pharmaceutical compositions and dosage forms are exemplary dosage forms. Optionally, the oral dosage form is a solid dosage form, such as a tablet, a caplet, a hard gelatin capsule, a starch capsule, a hydroxypropyl methylcellulose (HPMC) capsule, or a soft elastic gelatin capsule. Liquid dosage forms may also be provided by the present invention, including such non-limiting examples as a suspension, solution, syrup, or emulsion.

Tianeptine hydrochloride salt can be administered by controlled or delayed release means. Controlled release pharmaceutical products generally have a common goal of improving drug therapy over that achieved by their non-controlled release counterparts. Ideally, the use of an optimally designed controlled release preparation in medical treatment is characterized by a minimum of API (active pharmaceutical ingredient) substance being employed to cure or control the condition in a minimum amount of time. Advantages of controlled release pharmaceutical compositions generally include: 1) extended activity of the API; 2) reduced dosage frequency; 3) increased patient compliance; 4) usage of less total API; 5) reduction in local or systemic side effects; 6) minimization of API accumulation; 7) reduction in blood level fluctuations; 8) improvement in efficacy of treatment; 9) reduction of potentiation or loss of API activity; and 10) improvement in speed of control of diseases or conditions. (Kim, Cherng-ju, Controlled Release Dosage Form Design, 2 Technomic Publishing, Lancaster, Pa.: 2000).

Typical daily dosage forms of the invention comprise tianeptine hydrochloride salt, in an amount of from about 10.0 mg to about 50.0 mg, from about 12.5 mg to 37.5 mg, or from about 25.0 mg to about 37.5 mg. The dosage amounts described herein are expressed in amounts of tianeptine free base and do not include the weight of a counterion (e.g., chloride) or any water or solvent molecules.

In another embodiment of the invention, a pharmaceutical composition comprising tianeptine hydrochloride salt is administered orally as needed in an amount of from about 10.0 mg to about 50.0 mg, from about 12.5 mg to about 50.0 mg, from about 25.0 mg to about 50.0 mg, or from about 37.5 mg to about 50.0 mg tianeptine. For example, about 12.5 mg, about 25.0 mg, or about 37.5 mg. In specific embodiments, pharmaceutical compositions comprising tianeptine hydrochloride salt can be administered orally in amounts of about 25.0 mg or about 37.5 mg. The dosage amounts can be administered in single or divided doses. In another embodiment, a daily dose of a pharmaceutical composition comprising tianeptine hydrochloride salt comprises up to about 50.0 mg tianeptine. In other embodiments, the present invention is directed to compositions comprising tianeptine hydrochloride salt as described herein and one or more diluents, carriers, and/or excipients suitable for the administration to a mammal for the treatment or prevention of one or more of the conditions described herein. In one embodiment, a controlled release pharmaceutical composition of tianeptine hydrochloride requires a less complex mixture of excipients than other pharmaceutical compositions comprising another form of tianeptine.

The tianeptine hydrochloride salt of the present invention may also be used to prepare pharmaceutical dosage forms other than the oral dosage forms described above, such as topical dosage forms, parenteral dosage forms, transdermal dosage forms, and mucosal dosage forms. For example, such forms include creams, lotions, solutions, suspensions, emulsions, ointments, powders, patches, suppositories, and the like.

The tianeptine hydrochloride salt forms of the present invention can be characterized, e.g., by the TGA, DSC, DVS, single crystal x-ray diffractometer data, or by any one, any two, any three, any four, any five, any six, any seven, any eight, any nine, any ten, or any single integer number of PXRD 2-theta angle peaks, or by any combination of the data acquired from the analytical techniques described herein.

The present invention also relates to a novel phosphate salt of tianeptine. The properties of the phosphate salt of tianeptine are improved relative to one or more known forms of tianeptine, such as tianeptine free base or tianeptine sodium (the currently available form of tianeptine). The phosphate salt can take several forms including, but not limited to, hydrates and solvates as well as various stoichiometric ratios of ionized tianeptine to phosphate counterion. The invention also includes other forms of tianeptine phosphate salt including, but not limited to, polymorphs, co-crystals, and amorphous forms. The invention also provides novel pharmaceutical compositions comprising these forms, methods of making these forms, and related methods of treatment.

In one embodiment, the present invention comprises tianeptine phosphate salt.

In a further embodiment, the phosphate salt of tianeptine can be incorporated into a pharmaceutical composition. In a further embodiment, the phosphate salt of tianeptine can be incorporated into a controlled release pharmaceutical composition.

In another embodiment, the phosphate salt of tianeptine can be incorporated into a pharmaceutical composition comprising two or more layers of tianeptine phosphate such that one layer is substantially released prior to the substantial release of another layer in vivo. In another embodiment, the phosphate salt of tianeptine can be incorporated into a pharmaceutical composition comprising pellets, wherein the pellets have varying extents or compositions of coating so as to enable release of tianeptine over a substantially longer period of time than that of the currently available tianeptine (e.g., STABLON®).

In another embodiment, the phosphate salt of tianeptine can be incorporated into an osmotically active pharmaceutical composition suitable for oral administration. Osmotically active pharmaceutical compositions, osmotic pumps, osmotic drug delivery, and other osmotic technology suitable for oral administration can include, but are not limited to, OROS® Push-Pull and OROS® Tri-layer pharmaceutical compositions. In another embodiment, the phosphate salt of tianeptine can be incorporated into an OROS® drug delivery system. Such controlled release pharmaceutical compositions comprising the phosphate salt of tianeptine, such as an osmotically active pharmaceutical composition suitable for oral administration, may lead to a longer lasting therapeutic effect than that of tianeptine sodium salt in the currently marketed form.

Figure 9:
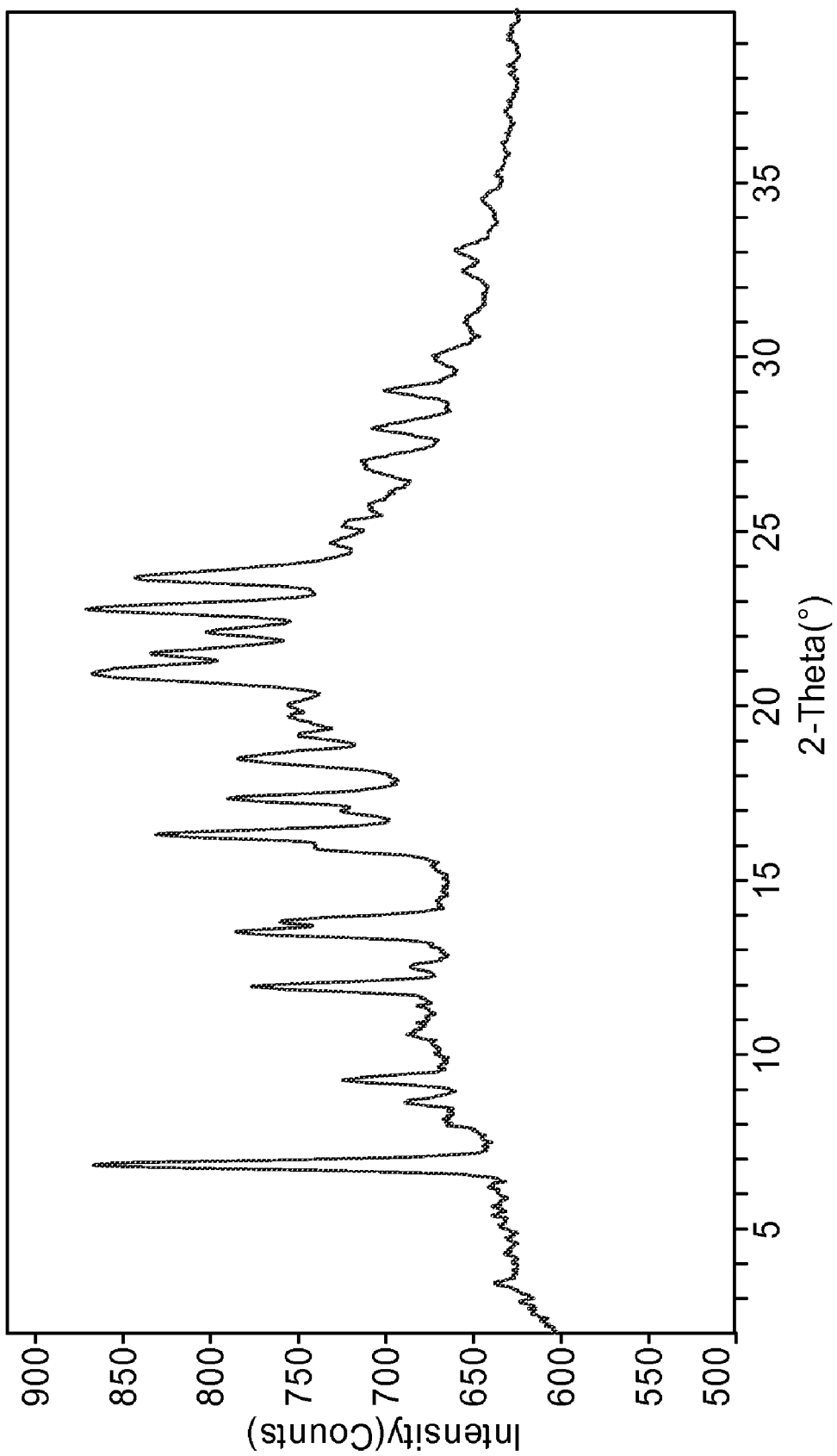
Figure 10:
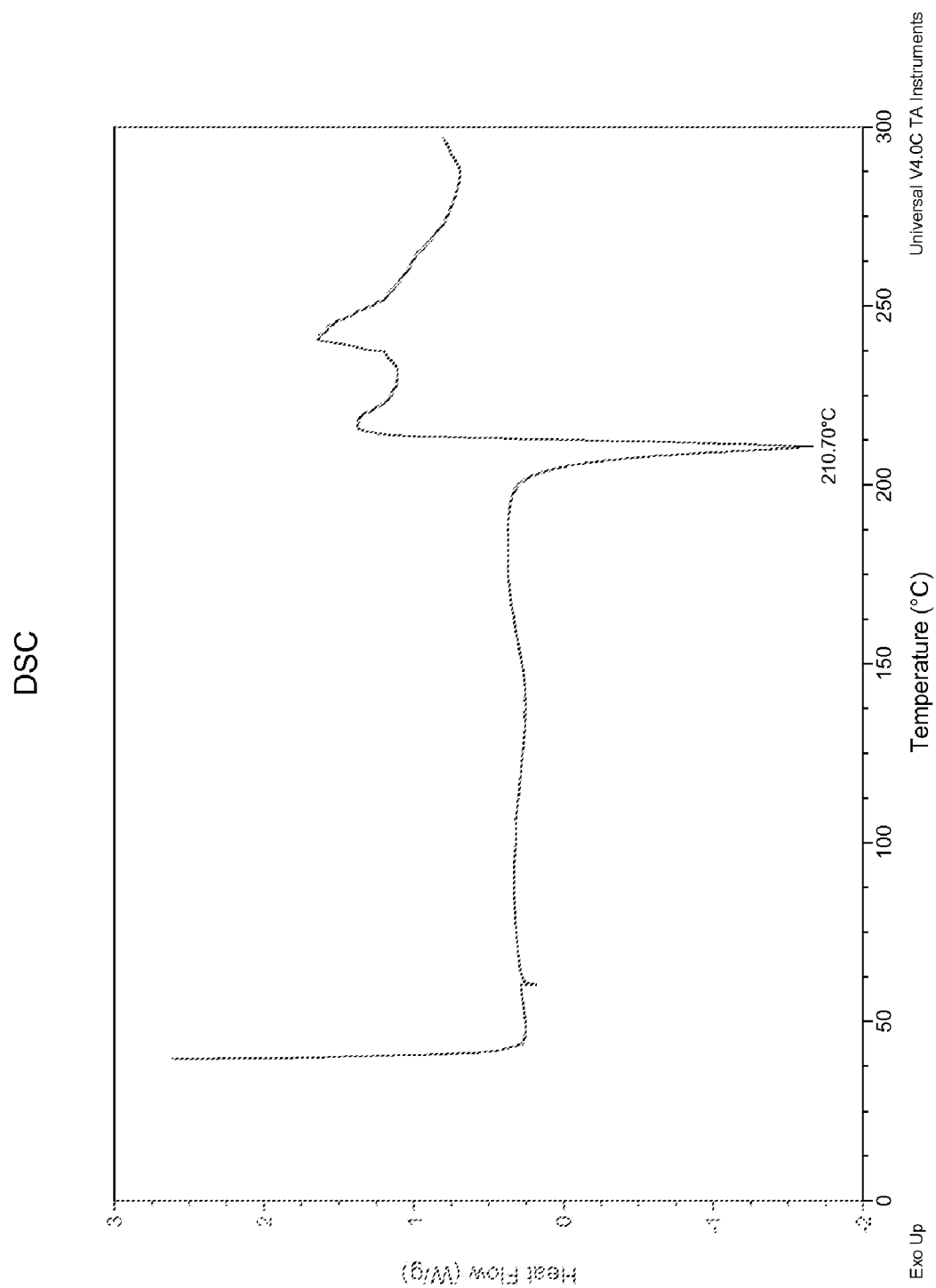
Figure 11:
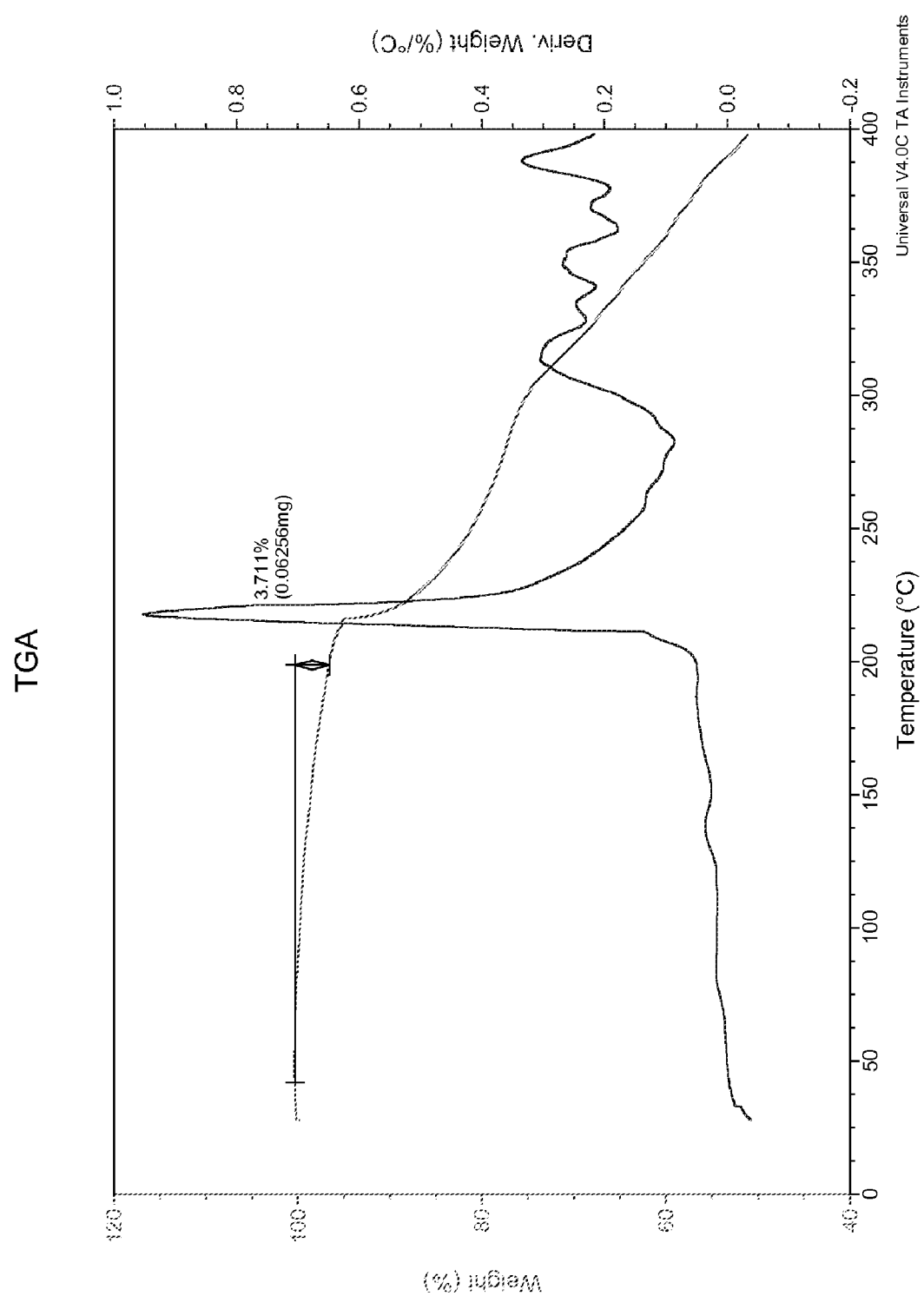
Figure 12:
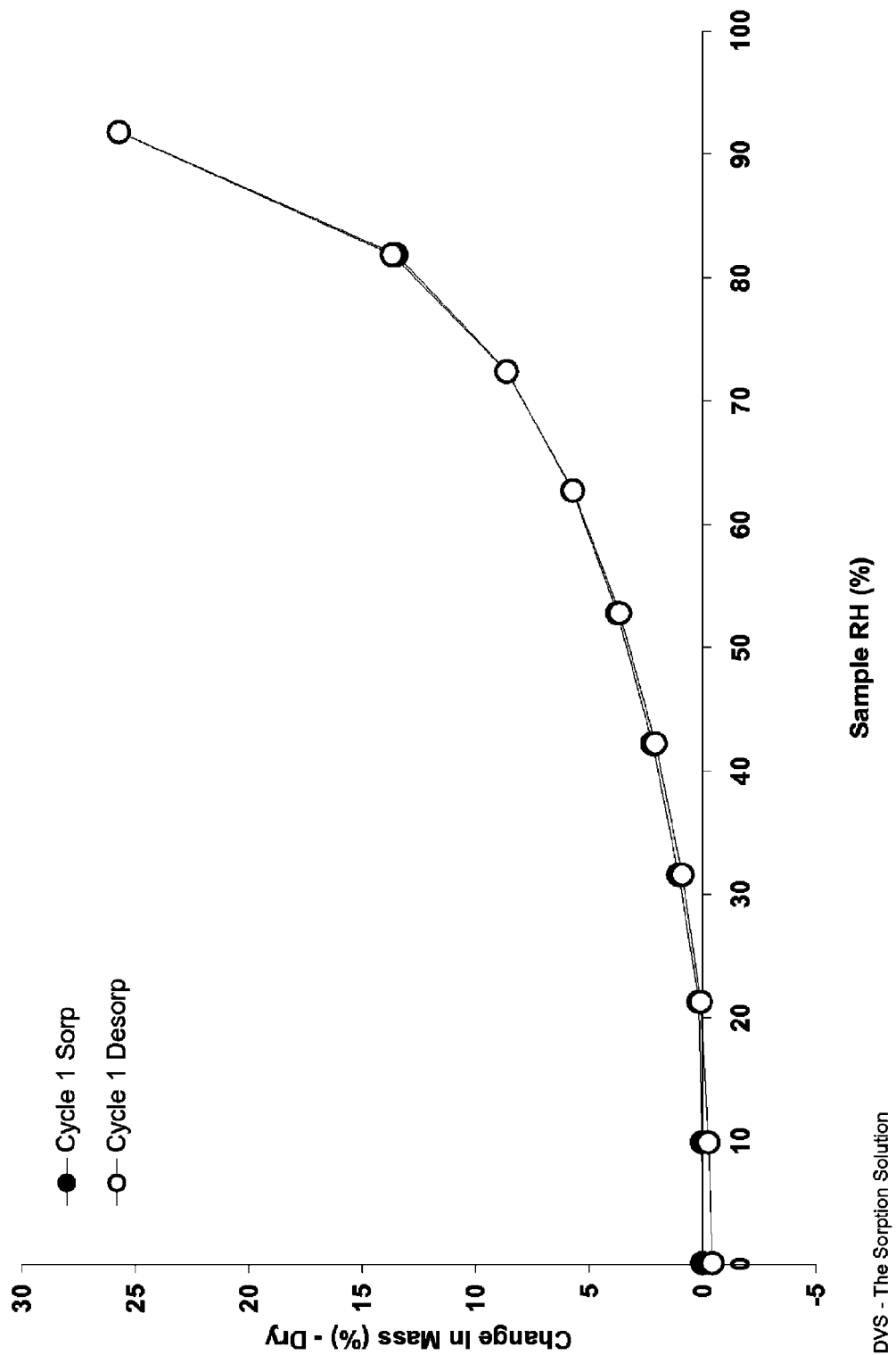

In another embodiment, the present invention comprises tianeptine phosphate. In another embodiment, the present invention comprises tianeptine phosphate, wherein the phosphate exhibits a PXRD diffractogram comprising a peak at about 6.83 degrees 2-theta. In another embodiment, the present invention comprises tianeptine phosphate, wherein the phosphate exhibits a PXRD diffractogram comprising a peak at about 9.27 degrees 2-theta. In another embodiment, the present invention comprises tianeptine phosphate, wherein the phosphate exhibits a PXRD diffractogram comprising a peak at about 11.95 degrees 2-theta. In another embodiment, the present invention comprises tianeptine phosphate, wherein the phosphate exhibits a PXRD diffractogram comprising peaks at about 6.83 and about 9.27 degrees 2-theta. In another embodiment, the present invention comprises tianeptine phosphate, wherein the phosphate exhibits a PXRD diffractogram comprising peaks at about 11.95 and about 13.53 degrees 2-theta. In another embodiment, the present invention comprises tianeptine phosphate, wherein the phosphate exhibits a PXRD diffractogram comprising peaks at about 16.31 and about 17.35 degrees 2-theta. In another embodiment, the present invention comprises tianeptine phosphate, wherein the phosphate exhibits a PXRD diffractogram comprising peaks at about 6.83, about 11.95, and about 13.53 degrees 2-theta. In another embodiment, the present invention comprises tianeptine phosphate, wherein the phosphate exhibits a PXRD diffractogram comprising peaks at about 16.31, about 17.35, about 18.47, and about 20.93 degrees 2-theta. In another embodiment, the present invention comprises tianeptine phosphate, wherein the phosphate exhibits a PXRD diffractogram comprising peaks at about 6.83, about 9.27, about 11.95, about 13.53, and about 16.31 degrees 2-theta. In another embodiment, the present invention comprises tianeptine phosphate, wherein the phosphate exhibits a PXRD diffractogram comprising peaks at about 20.93, about 21.49, about 22.77, and about 23.67 degrees 2-theta. In another embodiment, the present invention comprises tianeptine phosphate, wherein the phosphate exhibits a PXRD diffractogram comprising peaks at about 6.83, about 13.83, about 17.35, and about 18.47 degrees 2-theta. In another embodiment, the present invention comprises tianeptine phosphate, wherein the phosphate exhibits a PXRD diffractogram comprising peaks at about 9.27, about 11.95, about 13.53, about 16.31, and about 18.47 degrees 2-theta. In another embodiment, the present invention comprises tianeptine phosphate, wherein the phosphate exhibits a PXRD diffractogram comprising peaks at about 6.83, about 11.95, about 16.31, about 17.35, about 20.93, and about 22.77 degrees 2-theta. In another embodiment, the present invention comprises tianeptine phosphate, wherein the phosphate exhibits a PXRD diffractogram comprising peaks at about 6.83, about 9.27, about 11.95, about 13.53, about 13.83, about 15.93, about 16.31, about 17.35, about 18.47, about 20.93, about 21.49, about 22.77, and about 23.67 degrees 2-theta. In another embodiment, the present invention comprises tianeptine phosphate, wherein the phosphate exhibits a PXRD diffractogram substantially similar to FIG. 9. In another embodiment, the present invention comprises tianeptine phosphate, wherein the phosphate exhibits a DSC thermogram comprising an endothermic transition at about 211 degrees C. In another embodiment, the present invention comprises tianeptine phosphate, wherein the phosphate exhibits a DSC thermogram substantially similar to FIG. 10. In another embodiment, the present invention comprises tianeptine phosphate, wherein the phosphate exhibits a TGA thermogram substantially similar to FIG. 11. In another embodiment, the present invention comprises tianeptine phosphate, wherein the phosphate exhibits dynamic vapor sorption (DVS) characteristics substantially similar to FIG. 12. In another embodiment, tianeptine phosphate is incorporated into a controlled release pharmaceutical composition.

In another embodiment, the present invention comprises a tianeptine phosphate salt, wherein the phosphate salt is physically stable. In another embodiment, the present invention comprises a tianeptine phosphate salt, wherein the phosphate salt is physically stable from about 10% relative humidity to about 90% relative humidity. In another embodiment, the present invention comprises a tianeptine phosphate salt, wherein the phosphate salt is physically stable from about 20% relative humidity to about 80% relative humidity. In another embodiment, the present invention comprises a tianeptine phosphate salt, wherein the phosphate salt is physically stable from about 30% relative humidity to about 70% relative humidity.

According to the present invention, tianeptine phosphate salt can have various stoichiometric ratios of ionized tianeptine (cation) to phosphate counterion (anion). For example, the ratio of cation:anion can be about 1:1 or 2:1. Other stoichiometric ratios are also included in the invention.

In another embodiment, the present invention comprises tianeptine phosphate salt, and methods of making and using the same. In another embodiment, the present invention comprises a hydrate of tianeptine phosphate salt. In another embodiment, the present invention comprises a solvate of tianeptine phosphate salt. In another embodiment, the present invention comprises one or more polymorphs of tianeptine phosphate salt or one or more polymorphs of a hydrate or a solvate of tianeptine phosphate salt. In another embodiment, the present invention comprises a co-crystal of tianeptine phosphate salt. In another embodiment, the present invention comprises an amorphous form of tianeptine phosphate salt, and methods of making and using the same.

In another embodiment, a tianeptine phosphate salt form can exist in a form such as, but not limited to, an anhydrous form, a hydrate form, or a solvate form. Such hydrate and solvate forms can have various stoichiometric ratios of ionized tianeptine to water or solvate molecules such as, but not limited to, about 1:1, 1:1.5, 2:1, or 1:2.

In another embodiment, the present invention provides a method of making a phosphate salt of tianeptine, comprising:
  (e) providing tianeptine or a sodium salt thereof; and
  (f) contacting said tianeptine or a sodium salt thereof with phosphoric acid so as to crystallize said phosphate salt of tianeptine.

In a specific embodiment, said tianeptine is in the form of the sodium salt. In another embodiment, a solvent is added to said tianeptine or a sodium salt thereof prior to said hydrochloric acid. In another embodiment, step (b) is completed in the presence of a solvent such that a solution is formed prior to crystallization of the phosphate salt. In another embodiment, step (b) is completed in the presence of a solvent such that a suspension is formed prior to crystallization of the phosphate salt. In certain embodiments, a solvent is selected from the group consisting of: acetone, ethanol, nitromethane, methanol, acetonitrile, dichloromethane, water, and tetrahydrofuran (THF). In another embodiment, a solvent comprises a mixture of any two or more solvents, including, but not limited to, acetone, ethanol, nitromethane, methanol, acetonitrile, dichloromethane, water, and tetrahydrofuran.

Tianeptine free base and tianeptine sodium can be prepared by one or more methods available in the art, including, but not limited to, the method in U.S. Pat. No. 3,758,528.

In one embodiment of the present invention, an amount of tianeptine phosphate salt effective to modulate a mammal's physiology and/or to treat a mammal is administered to said mammal. In one aspect, the tianeptine phosphate salt is administered in an amount sufficient to effect modulation of a mammal's physiology and/or treatment.

In another embodiment, a method of treating a mammal suffering from depression is provided, comprising administering to said mammal an effective amount of a tianeptine phosphate salt. In another embodiment, a method of treating a mammal suffering from irritable bowel syndrome is provided, comprising administering to said mammal an effective amount of a tianeptine phosphate salt. In another embodiment, a method of treating a mammal suffering from attention deficit hyperactivity disorder is provided, comprising administering to said mammal an effective amount of a tianeptine phosphate salt. In another embodiment, a method of treating a mammal suffering from asthma is provided, comprising administering to said mammal an effective amount of a tianeptine phosphate salt. In another embodiment, said mammal is a human.

In another embodiment, the present invention includes the preparation of a medicament comprising a phosphate salt of tianeptine. Such a medicament can be used for treating depression, irritable bowel syndrome, attention deficit hyperactivity disorder, or asthma, in a mammal in need of such treatment. In another embodiment, said mammal is a human.

Pharmaceutical dosage forms of tianeptine phosphate salt can be administered in several ways including, but not limited to, oral administration. Oral pharmaceutical compositions and dosage forms are exemplary dosage forms. Optionally, the oral dosage form is a solid dosage form, such as a tablet, a caplet, a hard gelatin capsule, a starch capsule, a hydroxypropyl methylcellulose (HPMC) capsule, or a soft elastic gelatin capsule. Liquid dosage forms may also be provided by the present invention, including such non-limiting examples as a suspension, solution, syrup, or emulsion.

Tianeptine phosphate salt can be administered by controlled or delayed release means. Controlled release pharmaceutical products generally have a common goal of improving drug therapy over that achieved by their non-controlled release counterparts. Ideally, the use of an optimally designed controlled release preparation in medical treatment is characterized by a minimum of API (active pharmaceutical ingredient) substance being employed to cure or control the condition in a minimum amount of time. Advantages of controlled release pharmaceutical compositions generally include: 1) extended activity of the API; 2) reduced dosage frequency; 3) increased patient compliance; 4) usage of less total API; 5) reduction in local or systemic side effects; 6) minimization of API accumulation; 7) reduction in blood level fluctuations; 8) improvement in efficacy of treatment; 9) reduction of potentiation or loss of API activity; and 10) improvement in speed of control of diseases or conditions. (Kim, Cherng-ju, Controlled Release Dosage Form Design, 2 Technomic Publishing, Lancaster, Pa.: 2000).

Typical daily dosage forms of the invention comprise tianeptine phosphate salt, in an amount of from about 10.0 mg to about 50.0 mg, from about 12.5 mg to 37.5 mg, or from about 25.0 mg to about 37.5 mg. The dosage amounts described herein are expressed in amounts of tianeptine free base and do not include the weight of a counterion (e.g., phosphate) or any water or solvent molecules.

In another embodiment of the invention, a pharmaceutical composition comprising tianeptine phosphate salt is administered orally as needed in an amount of from about 10.0 mg to about 50.0 mg, from about 12.5 mg to about 50.0 mg, from about 25.0 mg to about 50.0 mg, or from about 37.5 mg to about 50.0 mg tianeptine. For example, about 12.5 mg, about 25.0 mg, or about 37.5 mg. In specific embodiments, pharmaceutical compositions comprising tianeptine phosphate salt can be administered orally in amounts of about 25.0 mg or about 37.5 mg. The dosage amounts can be administered in single or divided doses. In another embodiment, a daily dose of a pharmaceutical composition comprising tianeptine phosphate salt comprises up to about 50.0 mg tianeptine. In other embodiments, the present invention is directed to compositions comprising tianeptine phosphate salt as described herein and one or more diluents, carriers, and/or excipients suitable for the administration to a mammal for the treatment or prevention of one or more of the conditions described herein. In one embodiment, a controlled release pharmaceutical composition of tianeptine phosphate requires a less complex mixture of excipients than other pharmaceutical compositions comprising another form of tianeptine.

The tianeptine phosphate salt of the present invention may also be used to prepare pharmaceutical dosage forms other than the oral dosage forms described above, such as topical dosage forms, parenteral dosage forms, transdermal dosage forms, and mucosal dosage forms. For example, such forms include creams, lotions, solutions, suspensions, emulsions, ointments, powders, patches, suppositories, and the like.

The tianeptine phosphate salt forms of the present invention can be characterized, e.g., by the TGA, DSC, DVS, single crystal x-ray diffractometer data, or by any one, any two, any three, any four, any five, any six, any seven, any eight, any nine, any ten, or any single integer number of PXRD 2-theta angle peaks, or by any combination of the data acquired from the analytical techniques described herein.

Although the invention has been described with respect to various embodiments, it should be realized this invention is also capable of a wide variety of further and other embodiments within the spirit and scope of the appended claims.

EXAMPLES

Example 1

Tianeptine hemisulfate monohydrate (7-[(3-chloro-6, 11-dihydro-6-methyldibenzo[c,f][1,2]thiazepin-11-yl)amino]heptanoic acid S,S-dioxide hemisulfate monohydrate)

Example 1a

15 STABLON® (tianeptine sodium) tablets were ground in a mortar and pestle, and mixed with 15 mL tetrahydrofuran (THF) to extract tianeptine. The mixture was vortexed and sonicated to mix. The non-dissolved components were filtered using a Büchner funnel. The THF solvent was evaporated from the filtered clear solution, and the remaining composition was redissolved in 1.5 mL deionized water. Four equivalents of sulfuric acid were added to crystallize tianeptine hemisulfate monohydrate.

Example 1b

Tianeptine sodium (1054.16 grams) was dissolved in 50:50 acetic acid:water (4 liters) at 50° C. to give a colorless solution. The solution was hot filtered and to it was added sulfuric acid (66 milliliters) over approximately three minutes at 95° C. The solution produced crystalline tianeptine hemisulfate monohydrate within one hour at 95° C. The temperature was then ramped to 104° C. for 100 minutes, 80° C. for 220 minutes, 25° C. for 40 minutes, and 5° C. for 100 minutes. The mixture was then allowed to stir at 5° C. overnight (approximately 20 hours). The solid was then filtered and washed with 50:50 acetic acid:water (2×1 liter), water (3×1 liter), acetone (1×600 milliliters). The solid was then dried at 40° C. in vacuo.

Example 1c

Tianeptine sodium (100 grams) was dissolved in 50:50 isopropanol:water (500 milliliters) at room temperature to give a colorless solution. The solution was filtered and to it was added 45.4% sulfuric acid in water (73.2 milliliters). Crystalline tianeptine hemisulfate monohydrate was completely crystallized within two hours at which point the mixture was filtered. The solid was washed with 50:50 isopropanol:water (500 mL) and water (300 mL) and then allowed to dry under ambient conditions overnight.

Tianeptine hemisulfate monohydrate comprises a 1 to 0.5 to 1 ratio of ionized tianeptine to sulfate counterion to water.

Tianeptine hemisulfate monohydrate crystals representative of those obtained by completing the methods described in any of Examples 1a through 1c above were characterized using PXRD, DSC, TGA, dynamic vapor sorption (DVS), single crystal X-ray diffraction, UV/visible absorption, Fourier Transform Infrared Spectroscopy (FTIR) and Raman spectroscopy. The tianeptine hemisulfate monohydrate exhibits a PXRD diffractogram comprising peaks, for example, at about 8.25, 8.97, 11.49, 13.91, 14.73, 16.95, 18.07, 19.39, 20.59, 21.99, 22.83, and about 23.27 degrees 2-theta (See FIG. 1). DSC showed an endothermic transition at about 193 degrees C. (See FIG. 2). TGA showed the tianeptine hemisulfate monohydrate lost about 5.0 percent weight between about room temperature and about 160 degrees C. (See FIG. 3).

Dynamic vapor sorption (DVS) analysis was completed on tianeptine hemisulfate monohydrate from about 0 to about 90 percent relative humidity at about 25 degrees C. (See FIG. 4). The DVS analysis showed tianeptine hemisulfate monohydrate is stable from about 10% to about 90% relative humidity. This is characteristic of a non-hygroscopic material. Below 10% relative humidity, water mass was lost.

Single crystal data: $2(C_{21}H_{27}ClN_2O_4S_1).(SO_4).2(H_2O)$; M=503.99; Monoclinic, P2(1)/n; a=9.3816(4) angstroms; b=25.2869(10) angstroms; c=19.9621(7) angstroms; α=90 degrees; β=103.144(2) degrees; γ=90 degrees; V=4611.6(3) cubic angstroms; T=100(2) K; Z=8; $D_c$=1.452 grams/cubic centimeter; λ=0.71073 angstroms.

Figure 13:
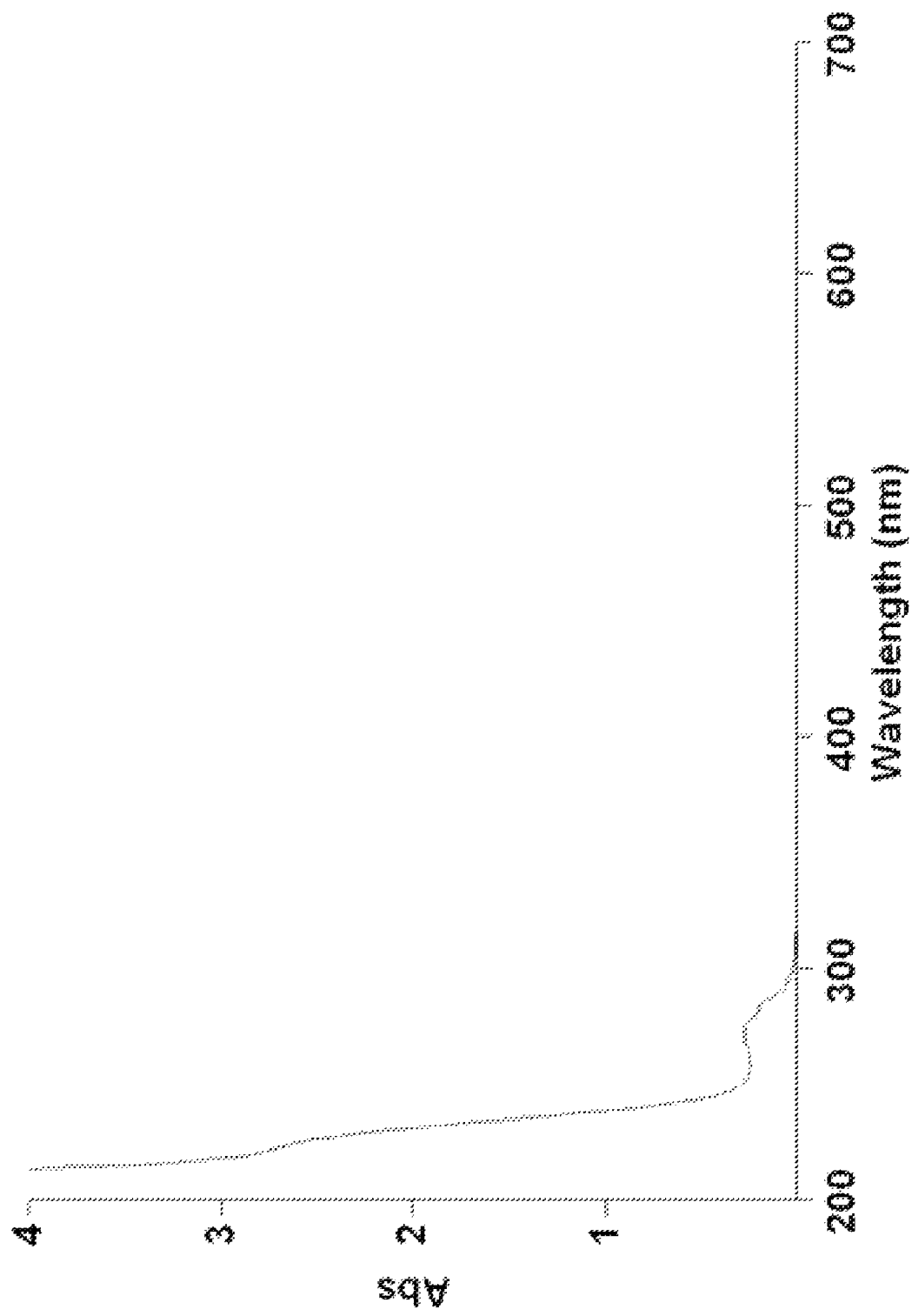

Tianeptine hemisulfate monohydrate exhibits a UV/visible spectrum comprising a maximum absorbance (λ max), for example, at about 208 nm and comprising a weak absorbance, for example, at about 275 nm (See FIG. 13).

Figure 14:
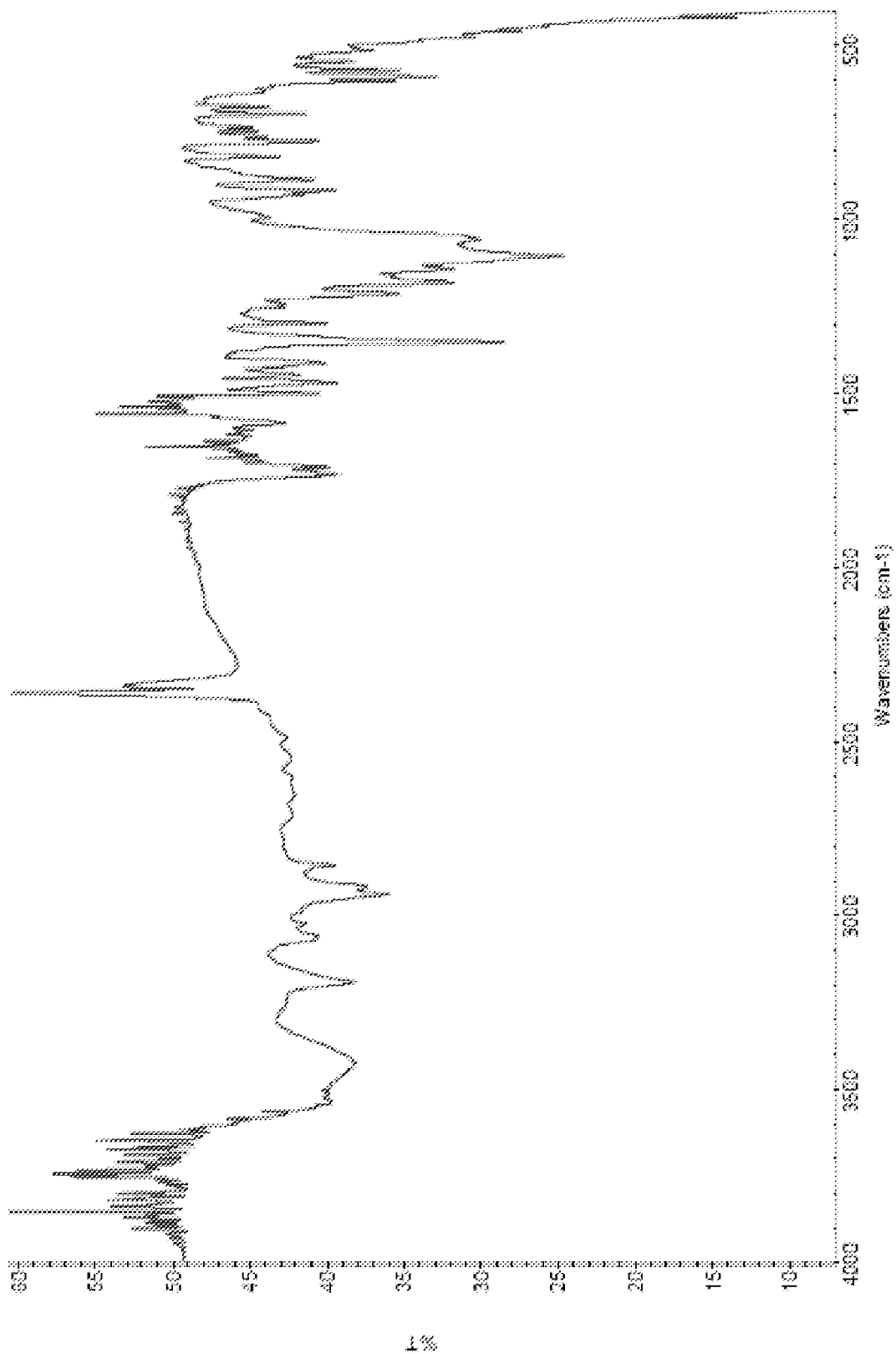

Tianeptine hemisulfate monohydrate exhibits an FTIR spectrum comprising peaks, for example, at about 1351, 1713, 1732, 2855, 2916, 2939, 3193 and 3540 $cm^{-1}$ (See FIG. 14).

Figure 15:
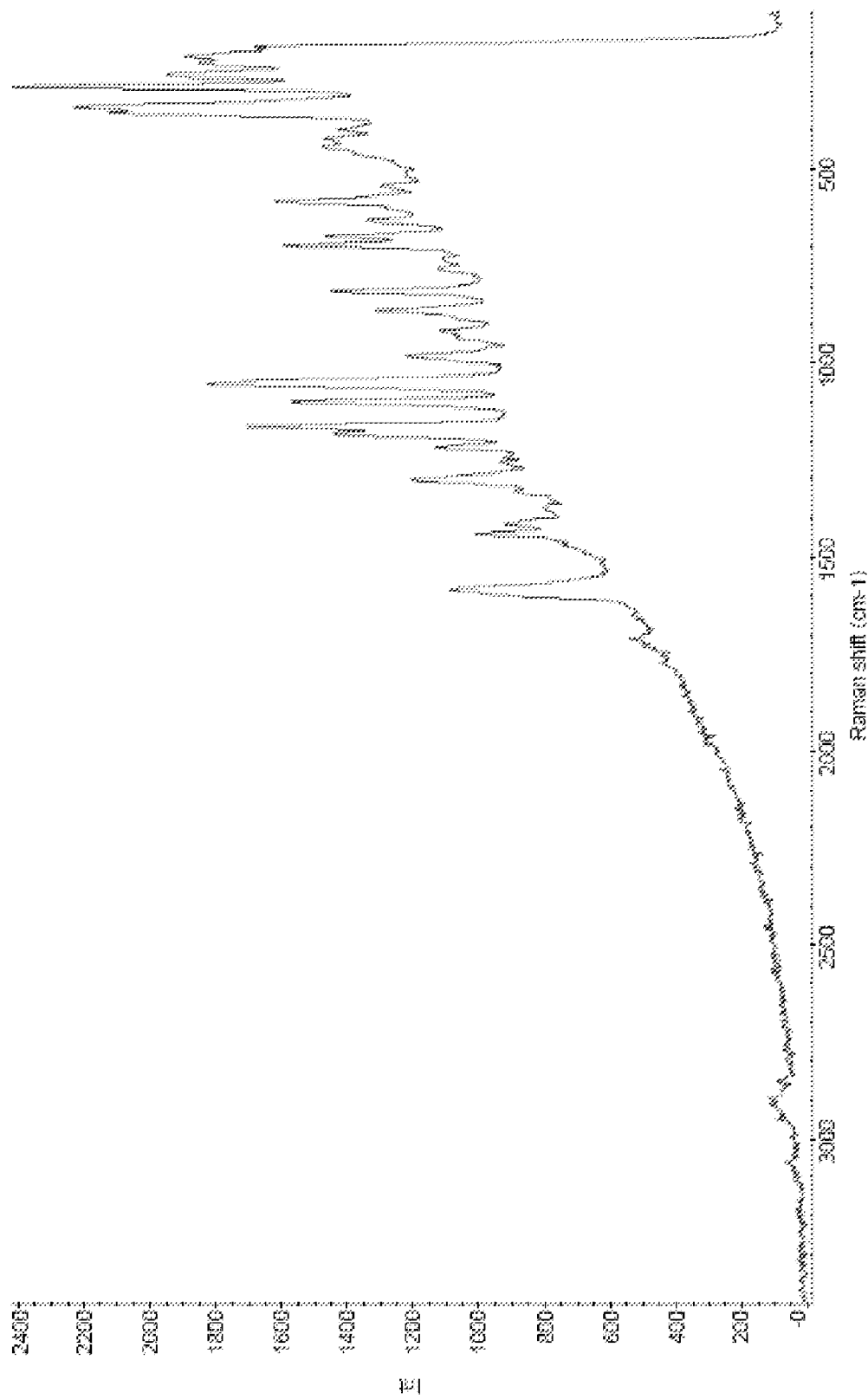

Tianeptine hemisulfate monohydrate exhibits a Raman spectrum comprising peaks, for example, at about 286, 339, 582, 672, 695, 1053, 1099, 1163, 1182, 1300 and 1586 $cm^{-1}$ (See FIG. 15).

The following analytical techniques were used.

Differential Scanning Calorimetry

DSC analysis of each sample was performed using a Q1000 Differential Scanning Calorimeter (TA Instruments, New Castle, Del., U.S.A.), which uses Advantage for QW-Series, version 1.0.0.78, Thermal Advantage Release 2.0 (©2001 TA Instruments-Water LLC), with the following components: QDdv.exe version 1.0.0.78 build 78.2; RHBASE.DLL version 1.0.0.78 build 78.2; RHCOMM.DLL version 1.0.0.78 build 78.0; RHDLL.DLL version 1.0.0.78 build 78.1; an TGA.DLL version 1.0.0.78 build 78.1. In addition, the analysis software used was Universal Analysis 2000 for Windows 95/95/2000/NT, version 3.1E; Build 3.1.0.40 (©2001 TA Instruments-Water LLC), or another version as specified in the drawings or otherwise herein.

For all of the DSC analyses, an aliquot of a sample was weighed into either a standard aluminum pan (Pan part # 900786.091; lid part # 900779.901) or a hermetic aluminum pan (Pan part # 900793.901; lid part # 900794.901 (TA Instruments, New Castle Del. USA)). Non-solvated samples were loaded into standard pans and were sealed either by crimping for dry samples or press fitting for wet samples (such as slurries). Solvated samples (including hydrates) were loaded into hermetic pans and hermetically sealed. The sample pan was loaded into the Q1000 Differential Scanning Calorimeter, which is equipped with an autosampler, and a thermogram was obtained by individually heating the same using the control software at a rate of 10° C./minute from $T_{min}$ (typically 30° C.) to $T_{max}$ (typically 300° C.) using an empty aluminum pan as a reference. Dry nitrogen (compressed nitrogen, grade 4.8 (BOC Gases, Murray Hill, N.J. USA)) was used as a sample purge gas and was set at a flow rate of 50 mL/minute. Thermal transitions were viewed and analyzed using the analysis software provided with the instrument.

Thermogravimetric Analysis

Thermogravimetric analysis (TGA) of samples was performed using a Q500 Thermogravimetric Analyzer (TA Instruments, New Castle, Del., U.S.A.), which uses Advantage for QW-Series, version 1.0.0.78, Thermal Advantage Release 2.0 (2001 TA Instruments-Water LLC). In addition, the analysis software used was Universal Analysis 2000 for Windows 95/98/2000/NT, version 3.1E; Build 3.1.0.40 (2001 TA Instruments-Water LLC), or another version as specified in the drawings or otherwise herein.

For the TGA experiments, the purge gas used was dry nitrogen, the balance purge was 40 mL/minute $N_2$, and the sample purge was 60 mL/minute $N_2$.

TGA was performed on the sample by placing a sample of the tianeptine sulfate salt in a platinum pan. The starting temperature was typically 20 degrees C. with a heating rate of 10 degrees C./minute, and the ending temperature was 300 degrees C.

Powder X-Ray Diffraction

Powder x-ray diffraction patterns were obtained using a D/Max Rapid X-ray Diffractometer (Rigaku/MSC, The Woodlands, Tex., U.S.A.).

The D/Max Rapid X-ray Diffractometer was equipped with a copper source ($Cu/K_\alpha$ 1.5406 Å), manual x-y stage, and 0.3 mm collimator. A sample was loaded into a 0.3 mm quartz capillary tube (Charles Supper Company, Natick, Mass., U.S.A.) by sectioning off the closed end of the tube and tapping the small, open end of the capillary tube into a bed of the powdered sample or into the sediment of a slurried sample. The loaded capillary tube was mounted in a holder that was placed and fitted into the x-y stage. A diffractogram was acquired using control software (RINT Rapid Control Software, Rigaku Rapid/XRD, version 1.0.0 (©1999 Rigaku Co.)) under ambient conditions at a power setting of 46 kV at 40 mA in transmission mode, while oscillating about the omega-axis from 0-5 degrees at 1 degree/second, and spinning about the phi-axis over 360 degrees at 2 degrees/second. The exposure time was 15 minutes unless otherwise specified.

The diffractogram obtained was integrated of 2-theta from 2-40 degrees and chi (1 segment) from 0-36 degrees at a step size of 0.02 degrees using the cyllnt utility in the RINT Rapid display software (RINT Rapid display software, version 1.18 (Rigaku/MSC)) provided by Rigaku with the instrument. The dark counts value was set to 8 as per the system calibration by Rigaku. No normalization or omega, chi, or phi offsets were used for the integration. The diffractograms included herein show raw data (no background subtraction).

The relative intensity of peaks in a diffractogram is not necessarily a limitation of the PXRD pattern because peak intensity can vary from sample to sample, e.g., due to crystalline impurities. Further, the angles of each peak can vary by about +/−0.1 degrees, or by about +/−0.05. The entire pattern or most of the pattern peaks may also shift by about +/−0.1 degrees to about +/−0.2 degrees due to differences in calibration, settings, and other variations from instrument to instrument and from operator to operator. All reported PXRD peaks in the Figures, Examples, and elsewhere herein are reported with an error of about ±0.1 degrees 2-theta. Unless otherwise noted, all diffractograms are obtained at about room temperature (about 24 degrees C. to about 25 degrees C.).

Single Crystal X-Ray Diffraction

The X-ray intensity data were measured at 100(2) K on a Bruker KAPPA APEX II CCD area detector system equipped with a graphite monchromator and a MoKα fine-focus sealed tube (λ=0.71073 Å) operated at 1.5 kW power (50 kV, 30 mA). Eight tianeptine molecules comprise the unit cell. The sulfate ion formed a salt on the secondary amine of two tianeptine molecules. Hydrogen bonding was observed between the sulfate ion and the carboxylic acid tail of two tianeptine molecules and one water molecule.

UV/Visible Absorption Spectroscopy

The UV-visible spectrum was measured with a Cary 50 UV-Vis analyzer (Vankel, Palo Alto, Calif.). Tianeptine hemisulfate monohydrate was dissolved in 50:50 methanol/water (0.150 mg/mL), filtered through a 0.45 um syringe filter, and then diluted 2× with the same solvent (0.075 mg/mL final concentration). A 1.0 mL aliquot of sample was added to a quartz cuvette having a 1.0 cm pathlength.

Fourier Transform Infrared Spectroscopy

FTIR analysis was performed on a Nexus 470 FTIR Instrument from Thermo Electron Corp. (Philadelphia, Pa.). Tianeptine hemisulfate monohydrate was ground together with KBr and compressed into a translucent disk. Analysis was performed in E.S.P. mode using 32 scans. A fresh background measurement was collected prior to sample analysis.

Raman Spectroscopy

Raman characterization was performed on a Nicolet Raman System from Thermo Electron Corp., equipped with a 785 nm laser-fitted microscope and a 10× objective. Dispersive Raman spectra were collected using 30 exposures with a 4 second window per exposure. A fresh background measurement was collected prior to sample analysis.

Example 2

Tianeptine hydrochloride (7-[(3-chloro-6,11-dihydro-6-methyldibenzo[c,f][1,2]thiazepin-11-yl)amino]heptanoic acid S,S-dioxide hydrochloride)

31 STABLON® (tianeptine sodium) tablets were ground in a mortar and pestle, and mixed with 23 mL tetrahydrofuran (THF) to extract tianeptine. The mixture was vortexed and sonicated to mix. The non-dissolved components were filtered using a Büchner funnel. The THF solvent was evaporated from the clear filtered solution, and the remaining composition was added to 4 mL deionized water. Four equivalents of hydrochloric acid were added to crystallize tianeptine hydrochloride.

Crystals representative of those obtained by completing the method above were characterized using PXRD, DSC, TGA, and dynamic vapor sorption (DVS). The tianeptine hydrochloride exhibits a PXRD diffractogram comprising peaks, for example, at about 7.23, 9.43, 9.91, 10.53, 14.53, 18.35, 21.39, and about 23.93 degrees 2-theta (See FIG. 5). DSC showed an endothermic transition at about 199 degrees C. (See FIG. 6). TGA showed the tianeptine hydrochloride lost about 2.9 percent weight between about room temperature and about 140 degrees C. (See FIG. 7).

Dynamic vapor sorption (DVS) analysis was completed on tianeptine hydrochloride from about 0 to about 90 percent relative humidity at about 25 degrees C. (See FIG. 8). The DVS analysis showed tianeptine hydrochloride is stable up to at least about 90% relative humidity. Over the entire humidity range, tianeptine hydrochloride absorbed less than about 2.5% water by mass.

Example 3

Tianeptine phosphate (7-[(3-chloro-6,11-dihydro-6-methyldibenzo[c,f][1,2]thiazepin-11-yl)amino]heptanoic acid S,S-dioxide phosphate)

15 STABLON® (tianeptine sodium) tablets were ground in a mortar and pestle, and mixed with 15 mL tetrahydrofuran to extract tianeptine. The mixture was vortexed and sonicated to mix. The non-dissolved components were filtered using a Büchner funnel. The THF solvent was evaporated from the clear solution, and the remaining composition was redissolved in 2.5 mL THF. Five equivalents of phosphoric acid were added to crystallize tianeptine phosphate.

Crystals representative of those obtained by completing the method above were characterized using PXRD, DSC, TGA, and dynamic vapor sorption (DVS). The tianeptine phosphate exhibits a PXRD diffractogram comprising peaks, for example, at about 6.83, 9.27, 11.95, 13.53, 13.83, 15.93, 16.31, 17.35, 18.47, 20.93, 21.49, 22.77, and about 23.67 degrees 2-theta (See FIG. 9). DSC showed an endothermic transition at about 211 degrees C. (See FIG. 10). TGA showed the tianeptine phosphate lost about 3.7 percent weight between about room temperature and about 199 degrees C. (See FIG. 11).

Dynamic vapor sorption (DVS) analysis was completed on tianeptine phosphate from about 0 to about 90 percent relative humidity at about 25 degrees C. (See FIG. 12). The DVS analysis showed tianeptine phosphate absorbed about 25% water by mass at 90% relative humidity.

Example 4

Comparative Dynamic Vapor Sorption (DVS) Data for Tianeptine Sodium

Figure 4:
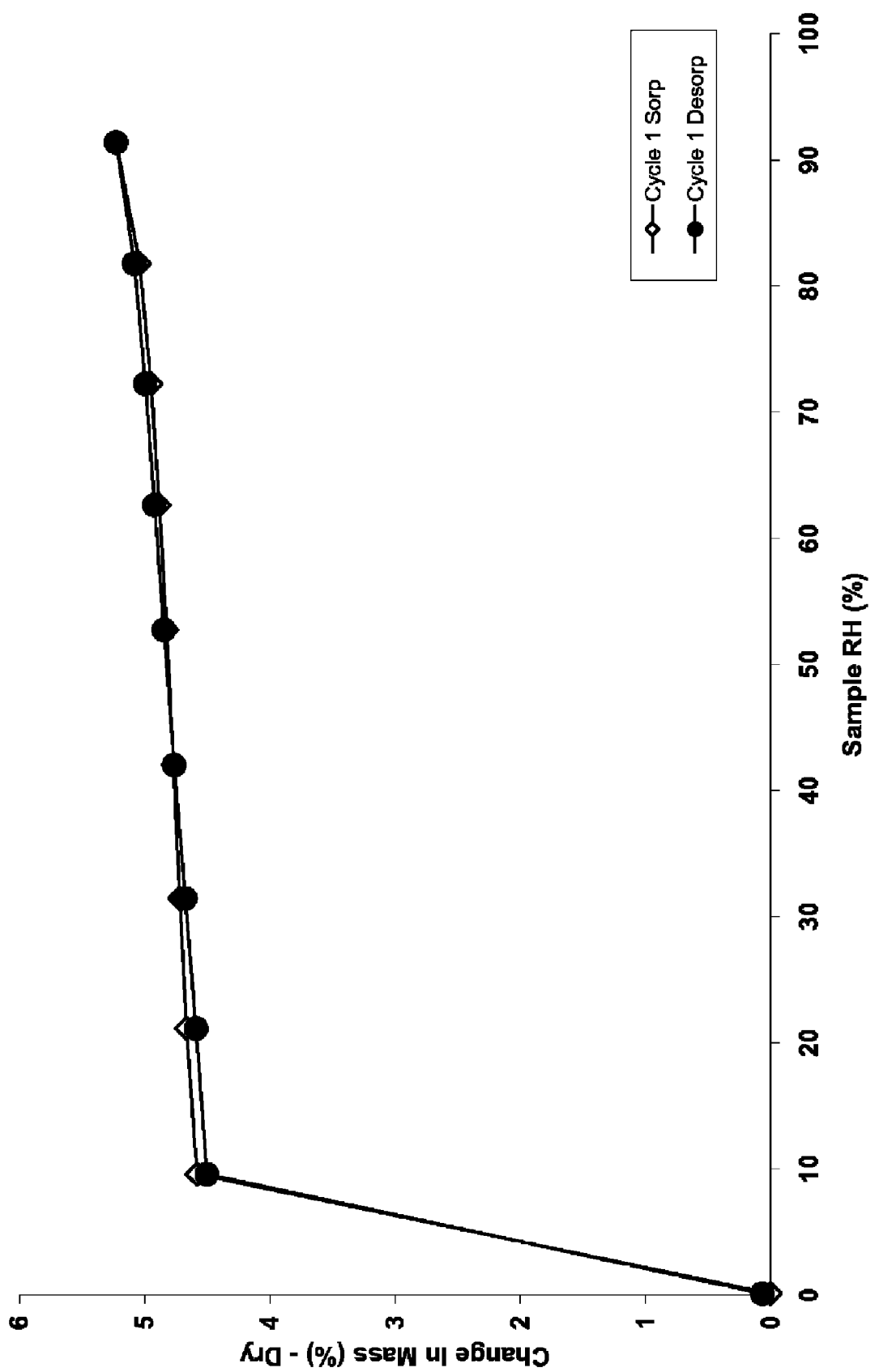
Figure 16:
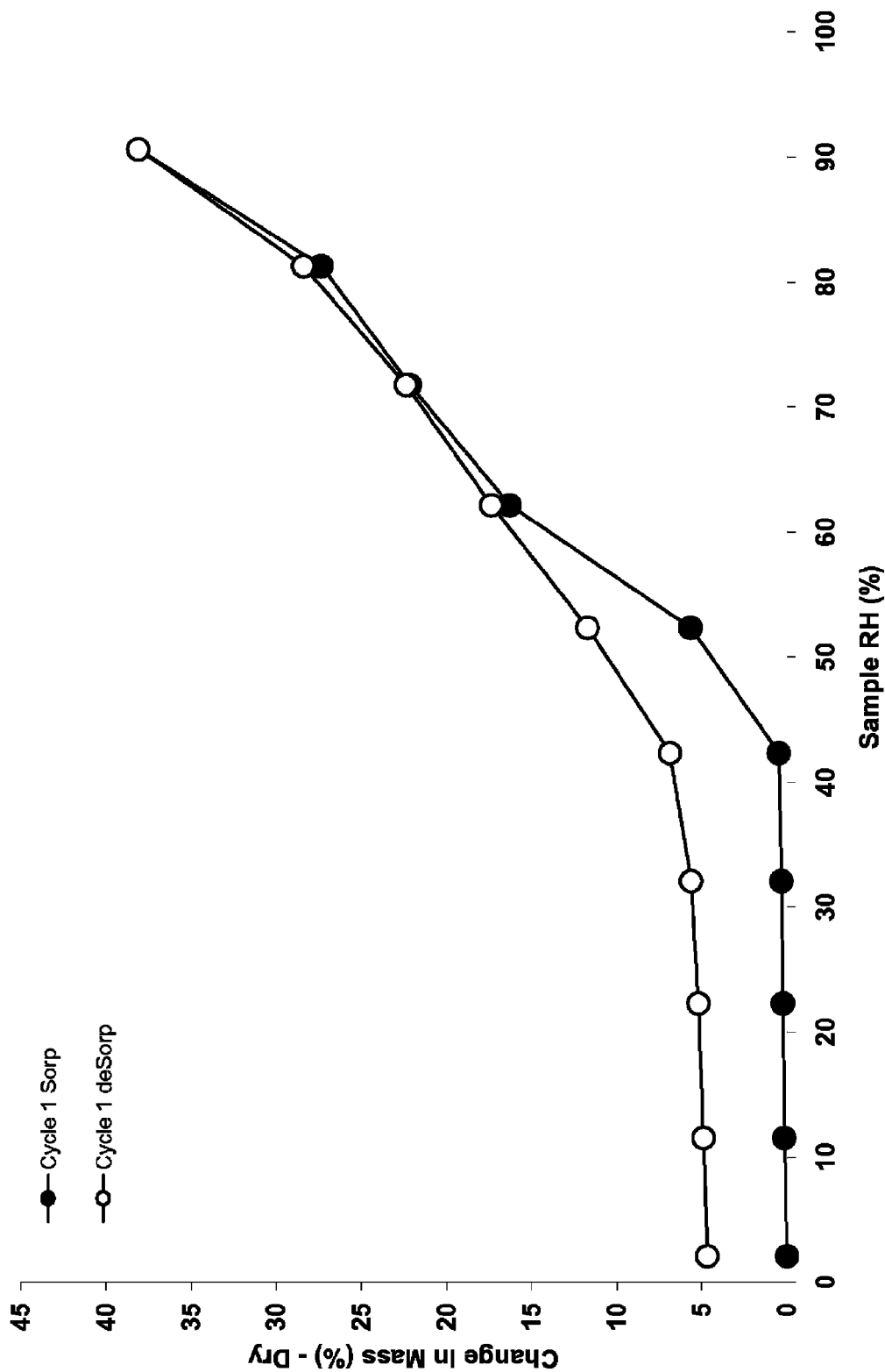

FIG. 16 shows comparative DVS data for tianeptine sodium (at about 25 degrees C.) to be compared with the DVS data for tianeptine hemisulfate monohydrate in FIG. 4. Tianeptine sodium began to deliquesce at about 60% relative humidity and had absorbed about 38% water (by mass) at about 90% relative humidity.

Example 5

Aqueous Solubility of Tianeptine Hemisulfate Monohydrate

Figure 17:
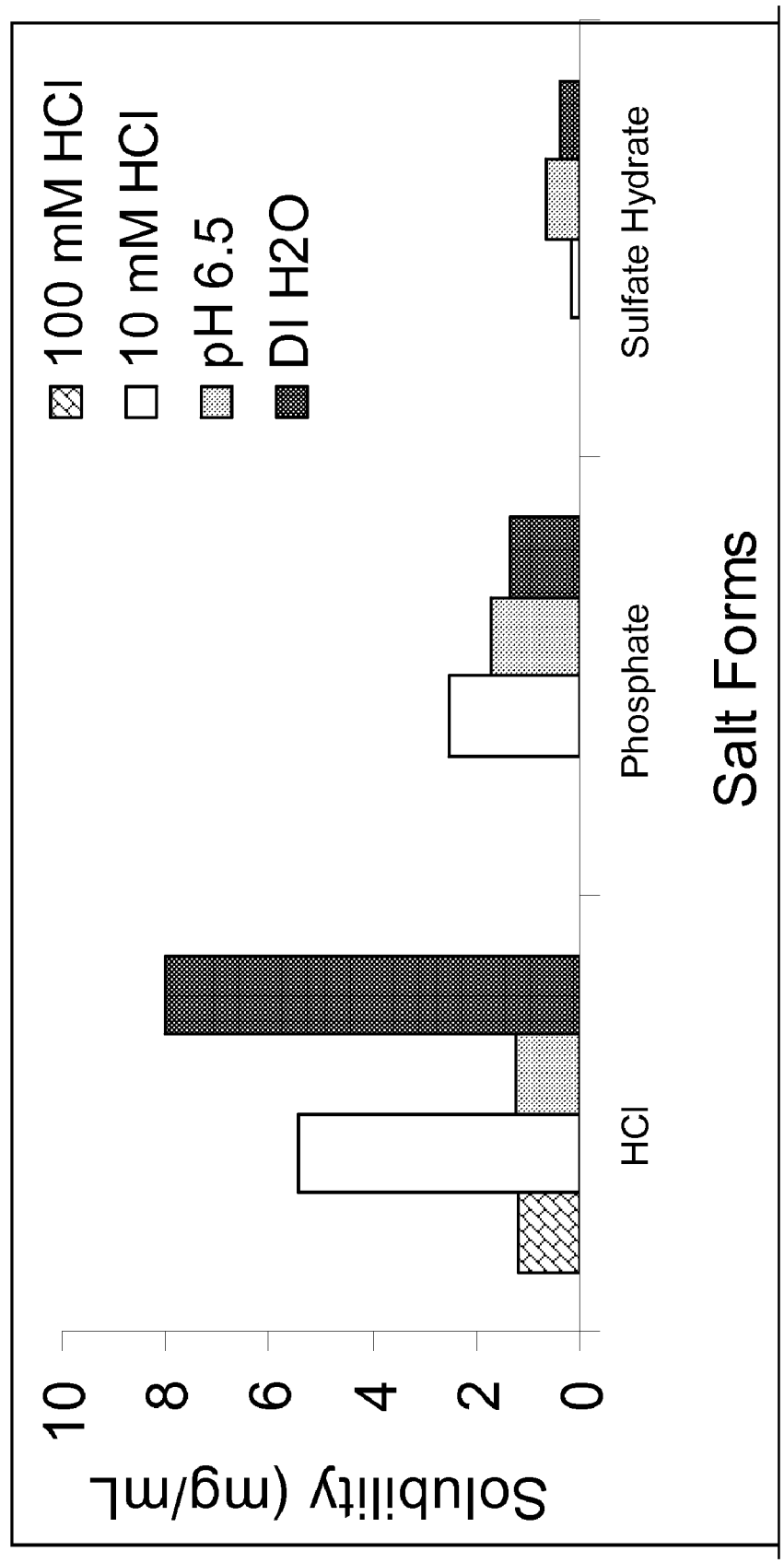

The aqueous solubility of tianeptine hemisulfate monohydrate was measured at room temperature by adding excess tianeptine hemisulfate monohydrate (from Example 1) to a solution and equilibrating for 24 hours under constant mixing. Three solutions were used, including 10 mM HCl solution, pH=6.5 (50 mM sodium phosphate) buffer solution, and deionized water. The remaining solids were removed from each solution and analyzed for solid-state form. Tianeptine hemisulfate monohydrate did not show any conversion to the free zwitterion form. In all three solutions, the solubility of tianeptine hemisulfate monohydrate was less than 1 mg/mL. FIG. 17 shows a comparison of the solubilities of tianeptine hemisulfate monohydrate, tianeptine hydrochloride, and tianeptine phosphate.

Example 6

Three formulations of tianeptine sulfate were made. The compositions are described below.

| Component | Role | Quantity per Tablet (mg) | | |
| --- | --- | --- | --- | --- |
| | | F1 | F2 | F3 |
| Tianeptine Hemisulfate Monohydrate | Active | 28.84 mg | 28.84 mg | 28.84 mg |
| Avicel PH200 | Filler | 60.00 mg | 60.00 mg | 60.00 mg |
| Methocel K100 LV CR Premium | Release controlling polymer | 108.66 mg | 81.50 mg | 54.33 mg |
| Methocel K4M CR Premium | Release controlling polymer | 0.00 mg | 27.16 mg | 54.33 mg |
| Magnesium Stearate | Lubricant | 2.00 mg | 2.00 mg | 2.00 mg |
| Colloidal silica | Flow aid | 0.50 mg | 0.50 mg | 0.50 mg |
| Total | | 200.00 mg | 200.00 mg | 200.00 mg |

Example 7

Figure 18:
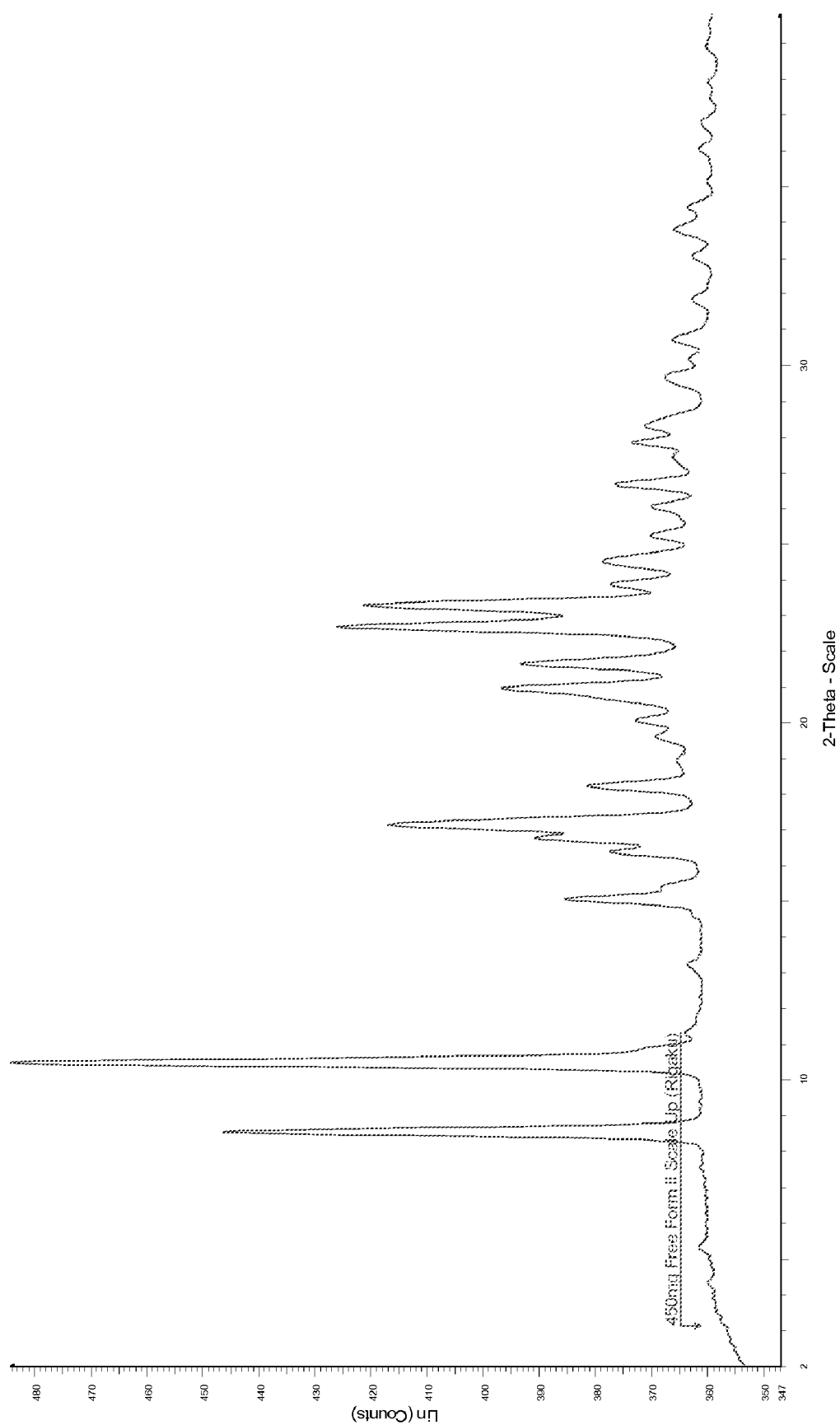

The pH solubility profile of the following tianeptine forms was measured: tianeptine hydrochloride; tianeptine hemisulfate monohydrate; tianeptine tosylate; tianeptine free form (Form II zwitterion, as described and identified in U.S. Publication No. US2008/0221081 A1, and for which the PXRD diffractogram is depicted in FIG. 18); and tianeptine sodium.

Tianeptine tosylate for use in this example was prepared by the following process. Tianeptine free form II (2.072 grams) was combined with p-toluenesulfonic acid (0.923 grams). To the solid mixture was added acetonitrile (50.0 milliliters). The mixture was heated to yield a clear solution. The solution was allowed to cool to room temperature and was then seeded with tianeptine tosylate (approximately 5 milligrams). The solution was allowed to stir overnight which yielded complete crystallization of the product. The suspension was then cooled to 0° C. and filtered to isolate the white crystalline solid.

The following provides another process by which tianeptine tosylate can be prepared. Tianeptine sodium (442.0 milligrams) is combined with p-toluenesulfonic acid (199.3 milligrams). To the solid mixture is added a 1:1 solution of ethyl acetate and toluene (10 milliliters total). The mixture is sonicated briefly to yield a solution and then stirred for approximately 15 minutes. Throughout the stirring, crystallization is evident as observed by formation of a white suspension. The solid is collected by filtration and is then dried at 75° C. under vacuum for 60 hours.

The following provides yet another process by which tianeptine tosylate can be prepared. Tianeptine free form II (45.5 milligrams) is combined with p-toluenesulfonic acid (21.5 milligrams). To the solid mixture is added acetonitrile (1.0 milliliters). The mixture is heated gently to yield a solution which is allowed to cool to room temperature and sit for 1 hour. A glass rod is used to scratch the inside of the vial containing the solution. Crystallization is induced and is nearly complete after about 15 minutes. The solid is collected by filtration and is characterized to be tianeptine tosylate.

Procedure for pH Solubility Profile Measurement:

Each tianeptine form was added to buffer in a glass vial. A stir bar was added and the vials were closed. The sealed vials were incubated at 37° C. under constant mixing for 24-36 hours. Post incubation, the remaining solids were removed from the solution via centrifuge filtration using a 0.2 um pore size filter. The pH of each filtrate was measured and then the solution was diluted 2 to 10 fold and assayed for tianeptine content using HPLC (UV detection). The remaining solids were characterized by powder X-ray diffraction to determine the resulting solid form in each vial (equilibrium form). Data for each tianeptine form can be found in Tables 1-5 below.

TABLE 1

Solubility starting from tianeptine hydrochloride in various buffers

| Buffer System | Initial Buffer pH | Experiment Temp (C.) | Solubility (mg/mL) | Final pH | Equilibrium Form |
| --- | --- | --- | --- | --- | --- |
| 100 mM HCl | 1 | 37 | 3.15 | 1.4 | HCl |
| 10 mM HCl | 2 | 37 | 7.47 | 2.2 | HCl |
| 100 mM chloroacetate | 3 | 37 | 3.81 | 2.5 | form II |
| 100 mM acetate | 5 | 37 | 0.06 | 4.4 | form II |
| 100 mM piperazine | 6 | 37 | 0.03 | 5.3 | form II |
| 100 mM phosphate | 7 | 37 | 0.02 | 6.4 | form II |
| 100 mM triethanolamine | 8 | 37 | 0.34 | 7.4 | form II |
| 100 mM glycine | 10 | 37 | 2.75 | 8.7 | form II |

TABLE 2

Solubility starting from tianeptine hemisulfate monohydrate in various buffers

| Buffer System | Initial Buffer pH | Experiment Temp (C.) | Solubility (mg/mL) | Final pH | Equilibrium Form |
| --- | --- | --- | --- | --- | --- |
| 100 mM HCl | 1 | 37 | 0.33 | 1.4 | sulfate |
| 10 mM HCl | 2 | 37 | 0.20 | 2.4 | sulfate |
| 100 mM chloroacetate | 3 | 37 | 0.25 | 3.0 | sulfate |
| 100 mM acetate | 5 | 37 | 0.12 | 4.7 | form II |
| 100 mM piperazine | 6 | 37 | 0.10 | 5.5 | form II |
| 100 mM phosphate | 7 | 37 | 0.10 | 6.6 | form II |
| 100 mM triethanolamine | 8 | 37 | 0.36 | 7.6 | form II |
| 100 mM glycine | 10 | 37 | 3.61 | 8.7 | form II |

TABLE 3

Solubility starting from tianeptine tosylate in various buffers

| Buffer System | Initial Buffer pH | Experiment Temp (° C.) | Solubility (mg/mL) | Final pH | Equilibrium Form |
| --- | --- | --- | --- | --- | --- |
| 100 mM HCl | 1 | 37 | 0.96 | 1.03 | tosylate |
| 10 mM HCl | 2 | 37 | 0.88 | 2.05 | tosylate |
| 100 mM chloroacetate | 3 | 37 | 1.01 | 3.02 | tosylate |
| 100 mM acetate | 5 | 37 | 0.06 | 4.61 | form II |
| 100 mM piperazine | 6 | 37 | 0.04 | 5.65 | form II |
| 100 mM phosphate | 7 | 37 | 0.05 | 6.76 | form II |
| 100 mM triethanolamine | 8 | 37 | 0.32 | 7.67 | form II |
| 100 mM glycine | 10 | 37 | 9.14 | 8.88 | form II |

TABLE 4

Solubility starting from tianeptine Form II in various buffers

| Buffer System | Initial Buffer pH | Experiment Temp (° C.) | Solubility (mg/mL) | Final pH | Equilibrium Form |
|---|---|---|---|---|---|
| 100 mM HCl | 1 | 37 | 1.36 | 1.17 | HCl |
| 10 mM HCl | 2 | 37 | 2.66 | 2.47 | form II |
| 100 mM chloroacetate | 3 | 37 | 0.83 | 3.08 | form II |
| 100 mM acetate | 5 | 37 | 0.04 | 5.06 | form II |
| 100 mM piperazine | 6 | 37 | 0.04 | 6.01 | form II |
| 100 mM phosphate | 7 | 37 | 0.06 | 7.08 | form II |
| 100 mM triethanolamine | 8 | 37 | 0.40 | 7.98 | form II |
| 100 mM glycine | 10 | 37 | 9.72 | 9.61 | form II |

TABLE 5

Solubility starting from tianeptine sodium in various buffers

| Buffer System | Initial Buffer pH | Experiment Temp (° C.) | Solubility (mg/mL) | Final pH | Equilibrium Form |
|---|---|---|---|---|---|
| 100 mM HCl | 1 | 37 | 1.86 | 1.68 | HCl |
| 100 mM HCl | 1 | 37 | 7.898 | 9.10 | form II |
| 10 mM HCl | 2 | 37 | 7.46 | 9.17 | form I & II |
| 10 mM HCl | 2 | 37 | 66.192 | 9.250 | na |
| 100 mM chloroacetate | 3 | 37 | 0.06 | 4.63 | form I & II |
| 100 mM chloroacetate | 3 | 37 | 60.54 | 9.41 | form II |
| 100 mM acetate | 5 | 37 | 1.50 | 8.45 | form I & II |
| 100 mM piperazine | 6 | 37 | 0.27 | 7.75 | form II |
| 100 mM phosphate | 7 | 37 | 39.53 | 9.40 | form II |
| 100 mM triethanolamine | 8 | 37 | 85.43 | 8.92 | form II |
| 100 mM glycine | 10 | 37 | 43.56 | 10.20 | na | na = not applicable because there was not enough residual solid

The tianeptine sodium samples described in Table 5 were repeated for three pH conditions (initial pH 1, 2, and 3) and at different target concentrations of drug. For example, for the pH 1 conditions, 60-70 mg of tianeptine sodium was added to 100 mM HCl. For the second sample, 60-70 mg of tianeptine sodium was added to 100 mM HCl and then additional tianeptine sodium was added until a suspension was achieved. This was done to achieve supersaturation of the drug. Accordingly, because there was a higher concentration of tianeptine sodium in the second sample, upon conversion of the tianeptine sodium salt to the equilibrium form, the final pH was different. The final pH and form impacts the solubility.

Figure 19:
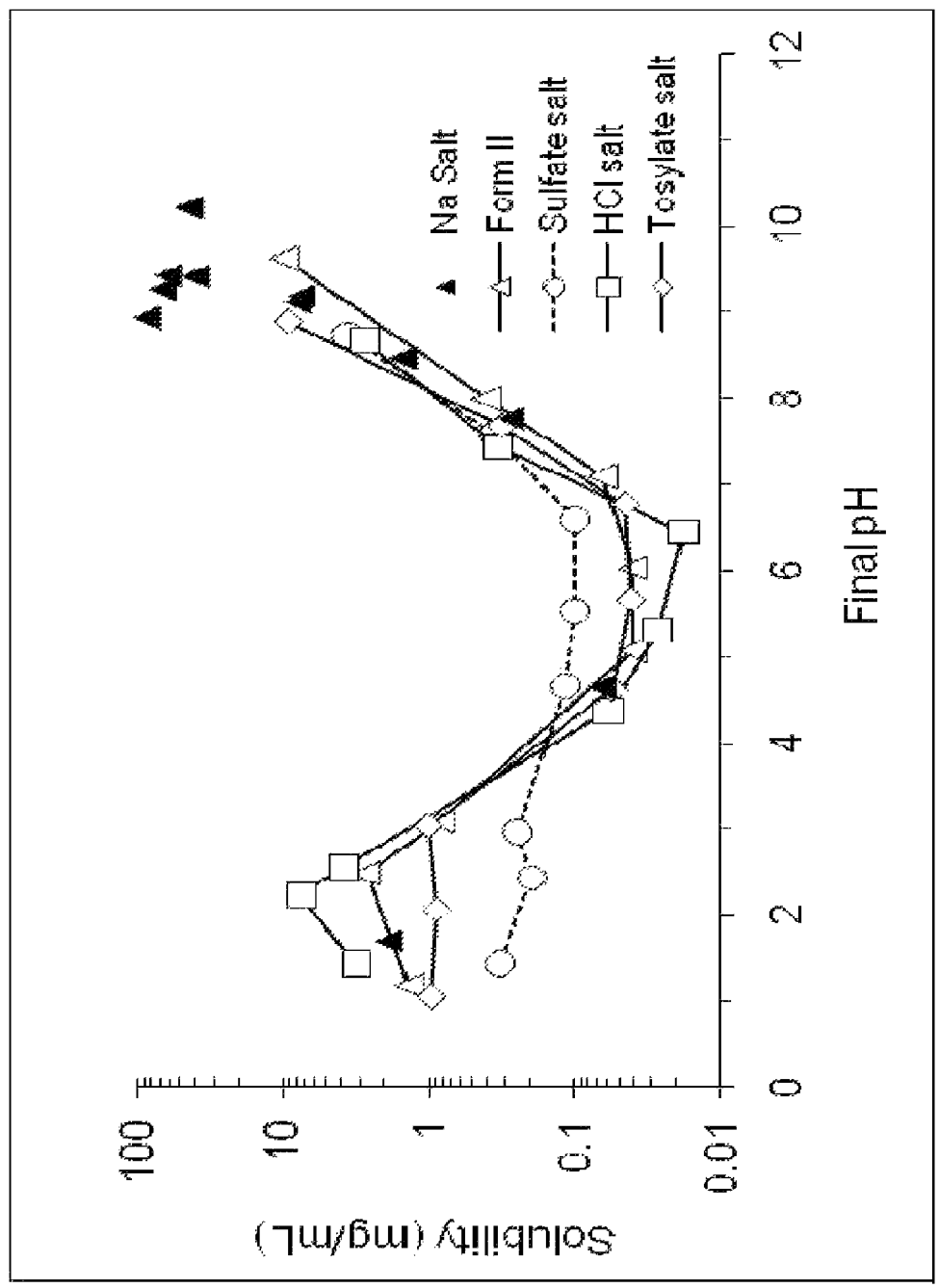

The pH solubility data for the various forms of tianeptine are plotted in FIG. 19.

As shown in FIG. 19, tianeptine hemisulfate monohydrate has a substantially flat solubility profile from pH 1 to pH 7 in contrast to the other forms of tianeptine, which have significantly higher solubility below pH 4.5 and a dramatic drop in solubility above pH 4.5. Uniform solubility over the entire pH range of the gastrointestinal tract is preferred for an oral controlled release dosage form. Such a solubility profile may reduce variability in tianeptine absorption if extended residence time in the stomach is highly variable (which is likely, especially in the presence of food). In the case of tianeptine hydrochloride, for instance, the data suggests that an extended residence time in the stomach may result in faster dissolution and absorption. Conversely, the dramatic drop in solubility in the intestines could then limit its dissolution and therefore absorption. Tianeptine hemisulfate monohydrate, with its comparatively uniform solubility profile, can reduce this variability, which may be beneficial for a controlled release dosage form. Solubility can have a significant impact on observed absorption variability.

Example 8

In Vitro Dissolution Study

Tablets containing tianeptine hemisulfate monohydrate were made using the three formulations identified as F1, F2 and F3 from Example 6 (except for the omission of colloidal silica). Tablets were also made using formulations analogous to F1, F2 and F3 from Example 6, except for the omission of colloidal silica and using the sodium salt of tianeptine as the active instead of tianeptine hemisulfate monohydrate. These tablets were tested in a USPII dissolution apparatus in order to assess the impact of salt form on drug release.

Required amounts of tianeptine hemisulfate monohydrate, Avicel PH200, and Methocel K4M and/or Methocel K100 for formulations F1, F2 and F3, respectively, were mixed for 10 minutes in an appropriately-sized glass jar using a Turbula blender. Then magnesium stearate was added and the blend was mixed for an additional 5 minutes. The typical powder blend batch size was 4 g.

Tablets (200±5 mg) were compressed manually using a Carver press with 8-mm flat round tooling, at typical compression forces ~650 kgf (~130 MPa).

Tablets containing tianeptine sodium salt (from CF Pharma, Budapest, Hungary (Lot HAT-357AB)) were similarly prepared.

Two separate dissolution experiments were performed. In one experiment, drug release from the tablets (F1, F2 and F3) containing tianeptine hemisulfate monohydrate was measured. In a second experiment, drug release from the tablets (F1, F2 and F3) containing tianeptine sodium salt was measured. In each experiment, the drug release from the tablets was measured using a USP dissolution apparatus, type II (paddle), particularly, a Varian VK 7000 USP Dissolution Apparatus II (rotating paddles). A Varian Cary 50 UV spectrophotometer was used for quantification of samples. 10 um PE full flow filters were used for automatically pumped sample lines.

The dissolution conditions were as follows:

| | |
|---|---|
| Medium and volume: | 900 mL simulated gastric fluid (SGF), pH ~1.2 |
| | 900 mL simulated intestinal fluid (SIF), pH ~6.5 |
| Degassing: | No degassing |
| Vessel type: | Peak-bottom vessel |
| Temperature: | 37.3 ± 0.5° C. |
| Paddle Height: | ~10 m m between paddle bottom and vessel peak |
| Agitation Rate: | 100 rpm |
| Detection: | In-line by UV absorption at 208 nm |
| Time-points: | every 6 minutes until 2 hours, then every 12 minutes until 3 hours, then every 30 minutes until 30 hours or until maximum absorbance plateau established |

The SGF dissolution medium was prepared by adding 2.0 g of NaCl and 7.0 ml of concentrated HCl to sufficient water to make 1000 ml solution, and then scaled as appropriate.

The SIF dissolution medium was prepared by adding 6.8 g of monobasic potassium phosphate ($KH_2PO_4$) and 0.66 g of sodium hydroxide (NaOH) to sufficient water to make 1000 ml solution (resulting pH~6.5), and then scaled as appropriate.

Release profile was normalized in accordance with the following calculation: (Absorbance)/(Absorbance at final time-point)×100%=% Dissolved normalized.

Results of the tianeptine hemisulfate monohydrate experiment are given in Table 6 below. The "% released" values in Table 6 were obtained by averaging over three replicates per formulation per medium.

TABLE 6

| | % released | | | | | |
|---|---|---|---|---|---|---|
| | SGF | | | SIF | | |
| Time (hours) | F1 (tianeptine hemisulfate monohydrate) | F2 (tianeptine hemisulfate monohydrate) | F3 (tianeptine hemisulfate monohydrate) | F1 (tianeptine hemisulfate monohydrate) | F2 (tianeptine hemisulfate monohydrate) | F3 (tianeptine hemisulfate monohydrate) |
| 0.00 | 0.59 | 0.80 | 0.43 | 0.30 | 0.39 | 0.28 |
| 0.10 | 0.09 | 0.28 | 0.21 | 0.44 | 0.30 | 0.42 |
| 0.20 | 0.61 | 0.79 | 0.68 | 1.31 | 0.82 | 1.02 |
| 0.30 | 1.33 | 1.42 | 1.05 | 2.42 | 1.36 | 1.46 |
| 0.40 | 2.19 | 2.11 | 1.49 | 3.41 | 1.97 | 2.12 |
| 0.50 | 3.26 | 2.86 | 1.90 | 4.57 | 2.85 | 2.69 |
| 0.60 | 4.41 | 3.67 | 2.43 | 5.97 | 3.50 | 3.26 |
| 0.70 | 5.72 | 4.60 | 2.95 | 6.95 | 4.28 | 3.88 |
| 0.80 | 7.02 | 5.60 | 3.55 | 8.52 | 5.08 | 4.59 |
| 0.90 | 8.38 | 6.59 | 4.14 | 9.73 | 6.08 | 5.17 |
| 1.00 | 9.82 | 7.62 | 4.76 | 11.19 | 7.24 | 5.88 |
| 1.10 | 11.47 | 8.70 | 5.35 | 12.53 | 7.95 | 6.58 |
| 1.20 | 12.83 | 9.75 | 5.96 | 14.08 | 8.98 | 7.28 |
| 1.30 | 14.28 | 10.86 | 6.61 | 15.18 | 9.94 | 7.96 |
| 1.40 | 15.76 | 11.97 | 7.27 | 16.56 | 10.87 | 8.64 |
| 1.50 | 17.39 | 13.04 | 7.97 | 17.88 | 11.91 | 9.41 |
| 1.60 | 18.77 | 14.13 | 8.63 | 19.03 | 12.85 | 10.16 |
| 1.70 | 20.31 | 15.25 | 9.33 | 20.44 | 13.88 | 10.91 |
| 1.80 | 21.87 | 16.31 | 10.04 | 21.69 | 14.80 | 11.61 |
| 1.90 | 23.41 | 17.37 | 10.77 | 22.95 | 15.79 | 12.31 |
| 2.00 | 24.88 | 18.49 | 11.55 | 24.17 | 16.77 | 13.03 |
| 2.20 | 27.83 | 20.60 | 13.07 | 26.74 | 18.67 | 14.47 |
| 2.40 | 30.98 | 22.67 | 14.67 | 29.38 | 20.63 | 15.86 |
| 2.60 | 34.07 | 24.77 | 16.32 | 32.22 | 22.51 | 17.35 |
| 2.80 | 36.87 | 26.79 | 18.13 | 34.70 | 24.49 | 18.84 |
| 3.00 | 39.60 | 28.78 | 19.76 | 37.11 | 26.51 | 20.31 |
| 3.50 | 45.91 | 33.85 | 24.16 | 42.52 | 31.30 | 24.12 |
| 4.00 | 51.43 | 38.59 | 28.34 | 47.47 | 35.69 | 27.88 |
| 4.50 | 56.64 | 43.23 | 32.58 | 52.16 | 39.77 | 31.49 |
| 5.00 | 61.59 | 48.18 | 36.54 | 56.67 | 43.99 | 34.82 |
| 5.50 | 66.23 | 52.51 | 40.13 | 60.91 | 47.70 | 37.83 |
| 6.00 | 70.71 | 56.38 | 43.55 | 64.84 | 51.19 | 40.69 |
| 6.50 | 74.74 | 59.98 | 46.96 | 68.72 | 54.34 | 43.40 |
| 7.00 | 78.39 | 63.52 | 50.04 | 72.28 | 57.57 | 46.10 |
| 7.50 | 81.75 | 66.93 | 53.19 | 75.68 | 60.81 | 48.79 |
| 8.00 | 84.70 | 70.11 | 56.16 | 78.80 | 64.00 | 51.68 |
| 8.50 | 87.58 | 73.16 | 59.11 | 81.80 | 66.98 | 54.46 |
| 9.00 | 90.24 | 76.25 | 61.92 | 84.51 | 69.83 | 57.22 |
| 9.50 | 92.99 | 79.12 | 64.80 | 86.90 | 72.51 | 59.89 |
| 10.00 | 94.80 | 81.94 | 67.57 | 89.03 | 75.14 | 62.55 |
| 10.50 | 96.69 | 84.59 | 70.39 | 90.94 | 77.55 | 65.13 |
| 11.00 | 97.72 | 86.88 | 72.84 | 92.80 | 79.96 | 67.76 |
| 11.50 | 98.41 | 89.02 | 75.29 | 94.61 | 82.07 | 70.15 |
| 12.00 | 98.87 | 90.92 | 77.66 | 96.07 | 83.92 | 72.43 |

TABLE 6-continued

| | % released | | | | | |
|---|---|---|---|---|---|---|
| | SGF | | | SIF | | |
| Time (hours) | F1 (tianeptine hemisulfate monohydrate) | F2 (tianeptine hemisulfate monohydrate) | F3 (tianeptine hemisulfate monohydrate) | F1 (tianeptine hemisulfate monohydrate) | F2 (tianeptine hemisulfate monohydrate) | F3 (tianeptine hemisulfate monohydrate) |
| 12.50 | 99.21 | 92.48 | 79.81 | 97.07 | 85.67 | 74.62 |
| 13.00 | 99.84 | 93.90 | 81.85 | 97.74 | 87.41 | 76.83 |
| 13.50 | 99.67 | 95.23 | 83.96 | 98.27 | 89.13 | 78.84 |
| 14.00 | 99.63 | 96.23 | 85.97 | 98.53 | 90.75 | 80.72 |
| 14.50 | 99.57 | 97.12 | 87.96 | 98.84 | 92.52 | 82.55 |
| 15.00 | 99.65 | 97.79 | 89.93 | 99.04 | 94.25 | 84.41 |
| 15.50 | 99.74 | 98.31 | 91.88 | 99.31 | 95.61 | 86.07 |
| 16.00 | 99.70 | 98.67 | 93.57 | 99.56 | 96.51 | 87.68 |
| 16.50 | 99.87 | 99.08 | 94.94 | 99.64 | 97.24 | 89.22 |
| 17.00 | 100.00 | 99.27 | 96.09 | 99.84 | 97.65 | 90.55 |
| 17.50 | 100.16 | 99.40 | 96.97 | 100.12 | 98.01 | 91.66 |
| 18.00 | | 99.49 | 97.62 | | 98.30 | 92.70 |
| 18.50 | | 99.56 | 98.14 | | 98.51 | 93.79 |
| 19.00 | | 99.46 | 98.49 | | 98.15 | 94.66 |
| 19.50 | | 99.55 | 98.53 | | 98.38 | 95.67 |
| 20.00 | | 99.57 | 98.79 | | 98.68 | 96.46 |
| 20.50 | | 99.61 | 98.96 | | 98.91 | 97.06 |
| 21.00 | | 99.73 | 99.11 | | 99.14 | 97.54 |
| 21.50 | | 99.81 | 99.07 | | 99.34 | 97.87 |
| 22.00 | | 99.86 | 99.25 | | 99.61 | 98.28 |
| 22.5 | | 99.97 | 99.32 | | 99.77 | 98.59 |
| 23 | | 100.00 | 99.35 | | 100.00 | 98.90 |
| 23.5 | | 100.08 | 99.45 | | 100.19 | 99.13 |
| 24 | | | 99.57 | | | 99.29 |
| 24.5 | | | 99.71 | | | 99.56 |
| 25 | | | 99.73 | | | 99.69 |

Results of the tianeptine sodium salt experiment are given in Table 7 below. The "% released" values in Table 7 were obtained from one replicate per formulation per medium.

TABLE 7

| | % released | | | | | |
|---|---|---|---|---|---|---|
| | SGF | | | SIF | | |
| Time (hours) | F1 (tianeptine sodium salt) | F2 (tianeptine sodium salt) | F3 (tianeptine sodium salt) | F1 (tianeptine sodium salt) | F2 (tianeptine sodium salt) | F3 (tianeptine sodium salt) |
| 0.00 | 0.62 | 0.63 | 0.46 | 0.23 | 0.35 | 0.29 |
| 0.10 | 5.14 | 5.03 | 3.91 | 4.20 | 3.33 | 4.21 |
| 0.20 | 8.66 | 7.98 | 6.31 | 6.30 | 4.97 | 6.64 |
| 0.30 | 11.30 | 10.14 | 8.11 | 7.84 | 6.17 | 8.52 |
| 0.40 | 13.60 | 11.92 | 9.59 | 9.30 | 7.24 | 9.86 |
| 0.50 | 15.65 | 13.48 | 10.97 | 10.68 | 8.43 | 11.15 |
| 0.60 | 17.60 | 15.17 | 12.26 | 12.29 | 9.59 | 12.34 |
| 0.70 | 19.58 | 16.73 | 13.45 | 13.95 | 10.87 | 13.48 |
| 0.80 | 21.58 | 18.14 | 14.62 | 15.59 | 12.21 | 14.55 |
| 0.90 | 23.42 | 19.56 | 15.72 | 17.25 | 13.55 | 15.62 |
| 1.00 | 25.09 | 21.01 | 16.92 | 18.69 | 14.95 | 16.63 |
| 1.10 | 26.87 | 22.43 | 17.90 | 20.34 | 16.04 | 17.62 |
| 1.20 | 28.66 | 23.73 | 18.93 | 21.87 | 17.40 | 18.56 |
| 1.30 | 30.20 | 25.11 | 19.91 | 23.39 | 18.66 | 19.67 |
| 1.40 | 31.80 | 26.52 | 21.01 | 24.71 | 19.74 | 20.73 |
| 1.50 | 33.38 | 27.70 | 21.99 | 26.20 | 20.86 | 21.77 |
| 1.60 | 34.87 | 29.06 | 23.46 | 27.58 | 21.94 | 22.74 |
| 1.70 | 36.34 | 30.27 | 23.90 | 29.00 | 23.04 | 23.67 |
| 1.80 | 38.03 | 31.52 | 24.77 | 30.33 | 24.15 | 24.68 |
| 1.90 | 39.03 | 32.73 | 25.69 | 31.65 | 25.13 | 25.54 |
| 2.00 | 40.53 | 33.96 | 26.56 | 32.92 | 26.16 | 26.42 |
| 2.20 | 43.07 | 36.18 | 28.32 | 35.51 | 28.25 | 28.15 |
| 2.40 | 45.61 | 38.59 | 30.06 | 37.93 | 30.26 | 29.78 |
| 2.60 | 47.99 | 40.82 | 31.63 | 40.20 | 32.04 | 31.41 |
| 2.80 | 50.37 | 42.95 | 33.25 | 42.40 | 34.03 | 33.03 |
| 3.00 | 52.54 | 45.16 | 34.82 | 44.67 | 35.96 | 34.58 |
| 3.50 | 57.87 | 50.35 | 38.62 | 49.71 | 40.64 | 38.24 |

TABLE 7-continued

| | % released | | | | | |
|---|---|---|---|---|---|---|
| | SGF | | | SIF | | |
| Time (hours) | F1 (tianeptine sodium salt) | F2 (tianeptine sodium salt) | F3 (tianeptine sodium salt) | F1 (tianeptine sodium salt) | F2 (tianeptine sodium salt) | F3 (tianeptine sodium salt) |
| 4.00 | 62.80 | 55.10 | 42.17 | 54.63 | 45.08 | 41.71 |
| 4.50 | 67.20 | 59.47 | 45.54 | 59.79 | 49.44 | 45.06 |
| 5.00 | 70.94 | 63.87 | 48.72 | 64.71 | 53.46 | 48.30 |
| 5.50 | 74.56 | 68.16 | 51.87 | 70.10 | 57.37 | 51.37 |
| 6.00 | 77.84 | 72.07 | 55.20 | 72.47 | 62.05 | 54.40 |
| 6.50 | 80.86 | 75.44 | 58.32 | 76.17 | 66.55 | 57.20 |
| 7.00 | 84.20 | 78.52 | 61.79 | 79.74 | 70.01 | 60.07 |
| 7.50 | 86.84 | 81.37 | 64.85 | 82.88 | 73.28 | 63.27 |
| 8.00 | 89.38 | 83.91 | 67.87 | 85.57 | 76.17 | 66.45 |
| 8.50 | 91.54 | 86.23 | 70.18 | 87.94 | 79.32 | 69.32 |
| 9.00 | 93.34 | 88.39 | 72.79 | 90.09 | 82.11 | 72.15 |
| 9.50 | 95.28 | 90.25 | 74.94 | 91.81 | 84.72 | 74.60 |
| 10.00 | 96.67 | 92.05 | 77.59 | 93.21 | 87.08 | 76.94 |
| 10.50 | 97.77 | 93.60 | 79.35 | 94.62 | 89.23 | 79.06 |
| 11.00 | 98.13 | 95.09 | 81.30 | 96.77 | 90.97 | 81.11 |
| 11.50 | 98.06 | 96.07 | 83.44 | 97.99 | 92.57 | 83.12 |
| 12.00 | 98.34 | 97.08 | 85.48 | 98.46 | 94.05 | 85.02 |
| 12.50 | 98.41 | 97.60 | 86.95 | 98.50 | 95.18 | 86.96 |
| 13.00 | 98.60 | 98.10 | 88.45 | 98.65 | 96.08 | 88.59 |
| 13.50 | 98.56 | 98.30 | 89.83 | 98.64 | 96.84 | 90.29 |
| 14.00 | 98.71 | 98.70 | 90.91 | 98.85 | 97.54 | 91.58 |
| 14.50 | 98.79 | 98.84 | 91.94 | 98.76 | 98.07 | 92.92 |
| 15.00 | 98.91 | 98.86 | 92.73 | 98.89 | 98.42 | 94.25 |
| 15.50 | 98.93 | 99.04 | 93.62 | 99.00 | 98.72 | 95.17 |
| 16.00 | 99.13 | 98.95 | 94.34 | 99.11 | 98.85 | 96.10 |
| 16.50 | 99.31 | 99.01 | 95.45 | 99.16 | 99.10 | 96.96 |
| 17.00 | 99.36 | 99.16 | 96.89 | 99.28 | 99.23 | 97.57 |
| 17.50 | 99.26 | 99.28 | 97.92 | 99.42 | 99.17 | 98.08 |
| 18.00 | 99.46 | 99.33 | 98.42 | 99.45 | 99.27 | 98.69 |
| 18.50 | 99.54 | 99.43 | 99.04 | 99.54 | 99.48 | 99.07 |
| 19.00 | 99.70 | 99.61 | 98.41 | 99.63 | 99.57 | 99.50 |
| 19.50 | 99.63 | 99.64 | 99.57 | 99.67 | 99.61 | 99.62 |
| 20.00 | 99.83 | 99.77 | 99.57 | 99.78 | 99.65 | 99.91 |
| 20.50 | 99.90 | 99.80 | 99.61 | 99.94 | 99.90 | 99.92 |
| 21.00 | 99.99 | 99.93 | 99.43 | 99.91 | 99.94 | 100.06 |
| 21.50 | 100.09 | 99.91 | 99.71 | 100.00 | 99.96 | 100.12 |
| 22.00 | 100.00 | 100.00 | 100.00 | 100.00 | 100.00 | 100.00 |

Figure 20:
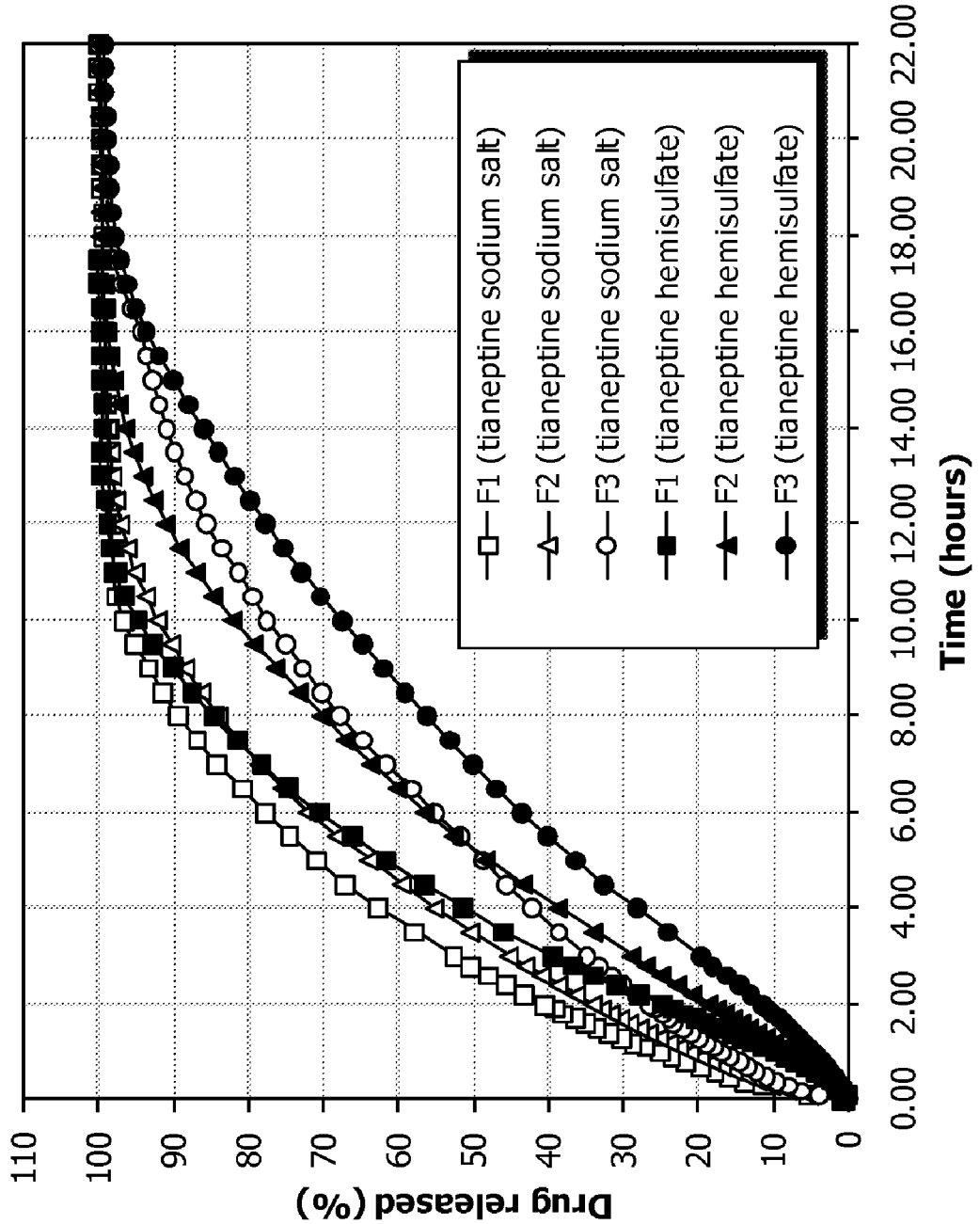
Figure 21:
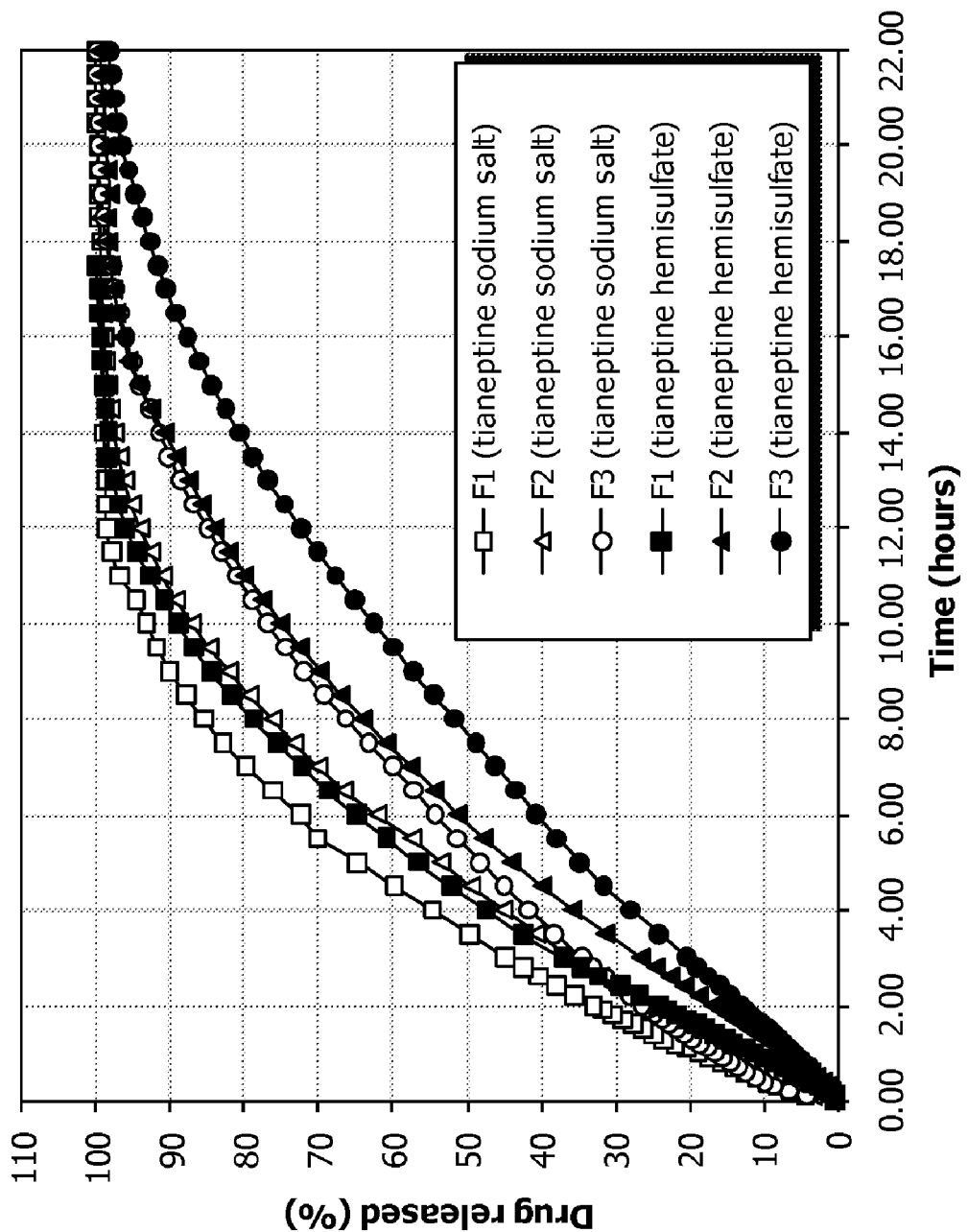

As shown by these results, the sodium salt (which is amorphous) is more soluble in SGF and in SIF than the hemisulfate monohydrate salt. In particular, as shown in FIGS. 20 and 21, which depict the results for the tablets containing tianeptine hemisulfate monohydrate tablets as compared to the tablets containing tianeptine sodium salt, tablets prepared with the sodium salt release faster, especially during early dissolution times.

Figure 22:
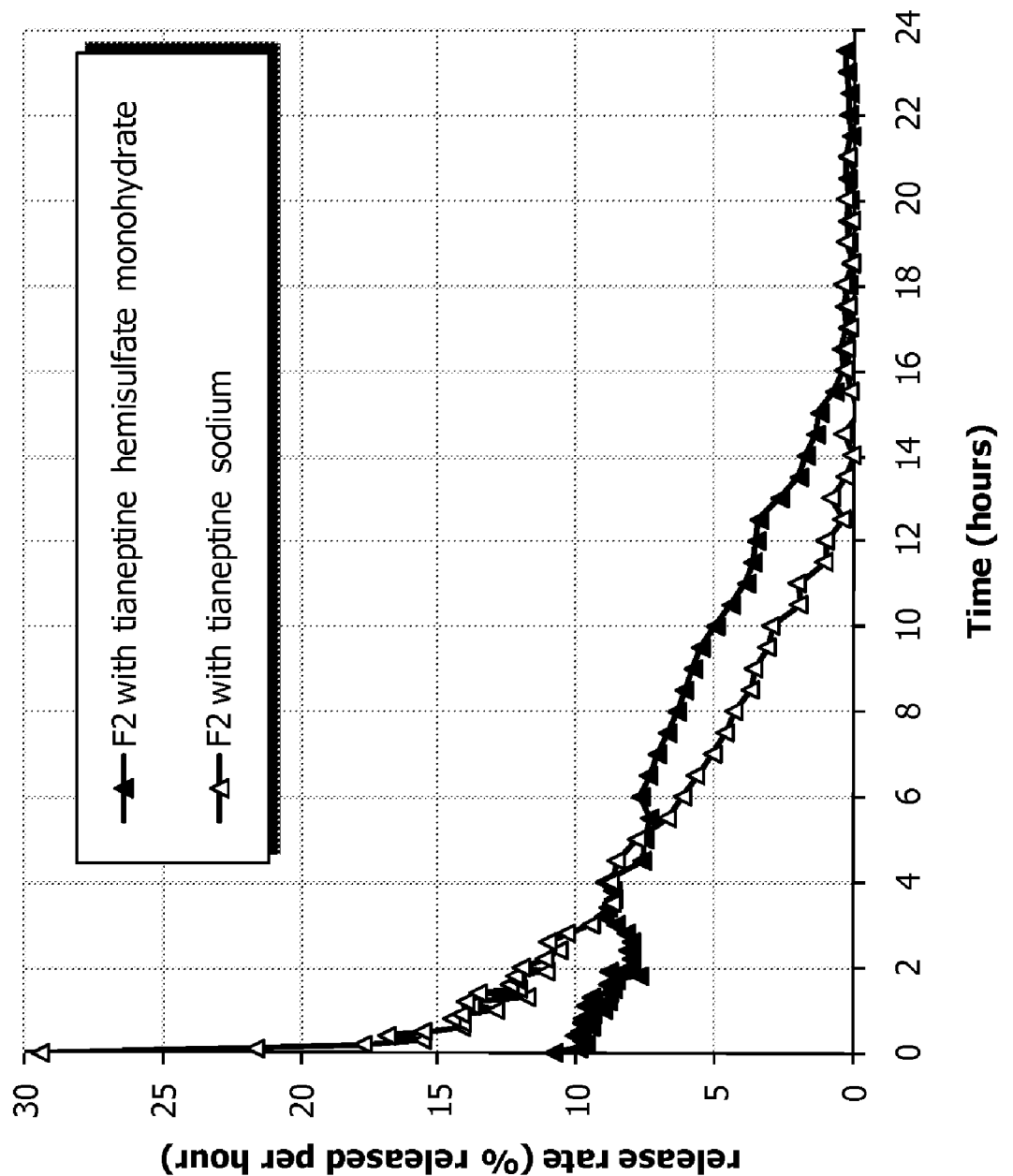
Figure 23:
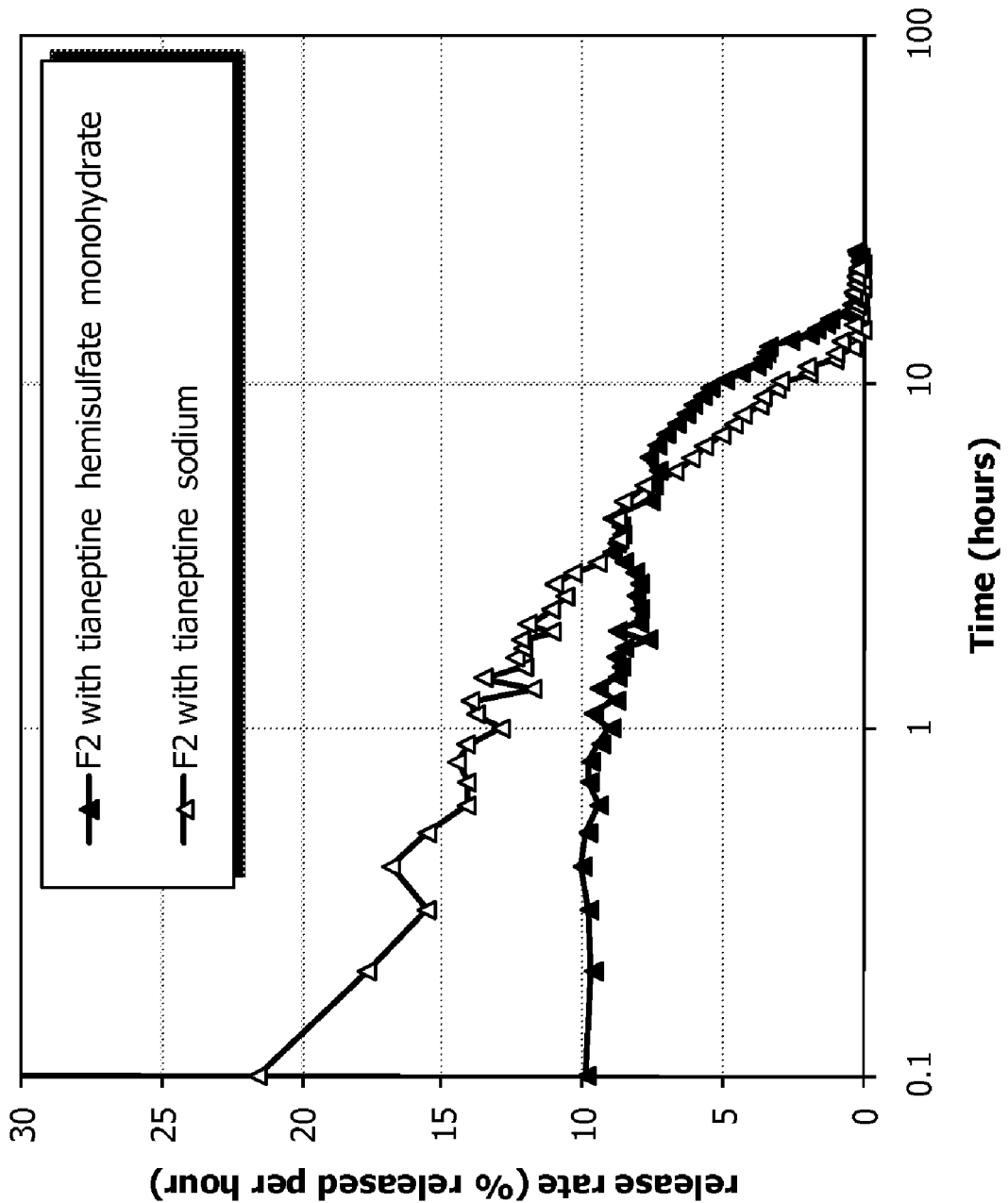

To further emphasize differences in release kinetics between the tablets prepared with the tianeptine sodium salt and the tianeptine hemisulfate monohydrate salt, release rates were calculated from the corresponding release profile data by taking first derivative with respect to time. As illustrated in FIG. 22 (tablet formulation F2 for each salt is used as an example), formulations based on the hemisulfate monohydrate salt result in much more steady release rates throughout the duration of the dissolution experiment than those for formulations based on the sodium salt. This difference can especially be seen when the x-axis (time) is presented in logarithmic coordinates, as illustrated in FIG. 23.

Example 9
Biological Assay
Behavioral Despair Test in Mouse (IP Administration)

The behavioral despair test in mouse, also known as the forced swim test, is an acute in vivo assay which detects antidepressant activity in test compounds.

The method, which detects antidepressant activity, follows that described by Porsolt et al (*Behavioural Despair in Mice: A Primary Screening Test for Antidepressants, Arch. Int. Pharmacodyn.*, 229 327-336, 1977). Mice forced to swim in a situation from which they cannot escape rapidly become immobile. Antidepressants decrease the duration of immobility.

Animals:

Male Rj NMRI (purchased from Elevage Janvier, France) with a body weight in the range of 20-28 g were delivered and stabilized for at least 5 days after delivery in MACROLON cages (25×19×13 cm, 10 animals per cage) on wood litter with free access to water and food (Code 11-3 from SAFE). The animals were housed under artificial lighting (12 hours) at a controlled ambient temperature of 21±3° C. and relative humidity between 30-80%.

Following testing, all animals were sacrificed by exposure to a mixture of $O_2/CO_2$ (20%/80%) followed by $CO_2$ or cervical elongation.

Formulations and Test Compounds

In STUDY A, tianeptine hemisulfate monohydrate, as a white powder, was dissolved in physiological saline. Tianeptine sodium (available from a commercial source), as a white powder was dissolved in physiological saline, pH adjusted to 8.62. The control was the vehicle, physiological saline. The reference compound, imipramine hydrochloride as a white powder (purchased from Sigma), was dissolved in physiological saline.

In STUDY B, tianeptine hemisulfate monohydrate, as a white powder, was dissolved in physiological saline, pH adjusted to 8.71 (STUDY B). The control was the vehicle, physiological saline. The reference compound, imipramine hydrochloride as a white powder (purchased from Sigma), was dissolved in physiological saline.

Additional formulation excipient included 1N hydrochloric acid, 2M sodium hydroxide and physiological saline (purchased from Laboratoire Aguettant).

Tianeptine hemisulfate monohydrate, tianeptine sodium, and imipramine hydrochloride formulation were stored at ambient temperature (approximately +20° C.). The vehicle solution was stored at approximately +4° C. Test compound, reference and vehicle were administered to the test animal in a volume of 10 mL/kg body weight. All formulations were administered at a volume of 10 mL/kg body weight.

Assay Procedure:

At the start of the assay, mice in each group were given a single dose of vehicle, reference compound, tianeptine hemisulfate monohydrate or tianeptine sodium at a dose as detailed below, 30 min prior to entrance into the swim chamber. After 30 minutes, the mice were individually placed in a cylinder (Height=24 cm; Diameter=13 cm) containing 10 cm water (22° C.) from which they could not escape. The mice were placed in the water for 6 minutes and the duration of immobility during the last 4 minutes was measured. 10 mice were studied per group. The test was performed blind. Viewpoint video-tracking software was utilized to record immobility time.

Study Design:

Tianeptine hemisulfate monohydrate was evaluated in two studies of the behavioral despair assay as detailed below.

In STUDY A, 10 animals each were assigned to one of six groups. Three groups were treated with tianeptine hemisulfate monohydrate, administered at 100 mg/kg, 150 mg/kg and 200 mg/kg, respectively. Tianeptine hemisulfate monohydrate was administered i.p., 30 minutes before the test and compared with animals dosed with vehicle. One group was treated with tianeptine sodium at 150 mg/kg, administered i.p, 30 minutes prior to testing. One group was treated with the reference compound (imipramine hydrochloride), administered at 32 mg/kg, i.p, 30 minutes prior to testing and a sixth group was treated with control vehicle, administered i.p, 30 minutes prior to testing.

In STUDY B, 10 animals each were assigned to one of four groups. Two groups were treated with tianeptine hemisulfate monohydrate, administered at 30 mg/kg and 60 mg/kg, respectively. Tianeptine hemisulfate monohydrate was administered i.p., 30 minutes before the test and compared with animals dosed with vehicle. The third group of animals was treated with the reference compound (imipramine hydrochloride), administered at 32 mg/kg, i.p, 30 minutes prior to testing and the fourth group was treated with control vehicle, administered i.p, 30 minutes prior to testing.

Results (STUDY A):

Animals were tested according to the procedure described above, with duration of immobility measured and tabulated below. The measured results were evaluated using the Student's t-test with * values indicating a statistically significant difference, with a p value of less than 0.001.

TABLE 8

STUDY A

| Treatment administered i.p. 30 min prior to testing | Duration of Immobility (sec) | | |
|---|---|---|---|
| | mean ± s.e.m. | p value | % change from control |
| Vehicle | 203.2 ± 5.5 | — | — |
| Tianeptine hemisulfate monohydrate (100 mg/kg) | 83.1 ± 21.2* | <0.0001 | −59% |
| Tianeptine hemisulfate monohydrate (150 mg/kg) | 115.5 ± 13.6* | <0.0001 | −43% |
| Tianeptine hemisulfate monohydrate (200 mg/kg) | 108.8 ± 19.8* | 0.0002 | −46% |
| Tianeptine sodium (150 mg/kg) | 102.0 ± 13.0* | <0.0001 | −50% |
| Imipramine (32 mg/kg) | 64.1 ± 16.1* | <0.0001 | −68% |

Tianeptine hemisulfate monohydrate, at 100 mg/kg, 150 mg/kg and 200 mg/kg decreased the duration of immobility, as compared with animals dosed with vehicle (−59%, −43% and −46% p<0.001 respectively). All animals showed Straub tail, hyperactivity and circling. Several animals had problems with swimming; two animals drowned, one at 100 mg/kg and one at 200 mg/kg. The data for these animals were not included in the results.

Tianeptine sodium, at 150 mg/kg similarly decreased the duration of immobility, as compared with animals dosed with vehicle (−50%, p<0.001). All animals showed straub tail, hyperactivity and circling. Several animals had problems with swimming; two animals drowned and the data for these animals is not included in the results.

In comparison, imipramine hydrochloride treated animals (at 32 mg/kg) also decreased the duration of immobility, as compared with vehicle control (−68%, p<0.001).

Results (STUDY B):

Animals were tested according to the procedure described above, with duration of immobility measured and tabulated below. The measured results were evaluated using the Student's t-test with * values indicating a statistically significant difference, with a p value of less than 0.001.

TABLE 9

STUDY B

| Treatment administered i.p. 30 min prior to testing | Duration of Immobility (sec) | | |
|---|---|---|---|
| | mean ± s.e.m. | p value | % change from control |
| Vehicle | 179.5 ± 12.1 | — | — |
| Tianeptine hemisulfate monohydrate (30 mg/kg) | 25.8 ± 8.7* | <0.0001 | −86% |
| Tianeptine hemisulfate monohydrate (60 mg/kg) | 29.7 ± 9.7* | <0.0001 | −83% |
| Imipramine (32 mg/kg) | 20.9 ± 8.5* | <0.0001 | −88% |

Tianeptine hemisulfate monohydrate, at 30 mg/kg and 60 mg/kg decreased the duration of immobility, as compared with animals dosed with vehicle (−86% and −83% p<0.001, respectively). At both doses, abnormal behavior (including Straub tail and circling) was observed in all ten mice prior to the test.

In comparison, imipramine hydrochloride treated animals (at 32 mg/kg) also decreased the duration of immobility, as compared with vehicle control (−88%, p<0.001).

The results of STUDIES A and B suggest the presence of antidepressant-like activity for tianeptine hemisulfate monohydrate over the dose-range 30 mg/kg-200 mg/kg i.p.

Example 10

Clinical Trial Study, Pharmacokinetics of Tianeptine Formulations

The clinical trial described below evaluated the single dose pharmacokinetics (PK) in a formulation selection, double-blind, randomized, four-treatment-sequence, four-period cross-over cohort with each treatment-sequence (n=3 per treatment sequence) receiving 25 mg of each of three tianeptine hemisulfate monohydrate controlled release (CR) tablet formulations and one 25-mg dose (2 tablets of 12.5 mg) of the marketed tianeptine sodium STABLON® immediate release (IR) formulation in random order based on a computer-generated randomization schedule.

Twelve subjects were enrolled in the trial. Subjects were healthy men or healthy, non-lactating women 21 to 55 years of age, inclusive. Clinical chemistry, hematology, and urinalysis tests were within normal, allowable limits (if out of range, was to be considered clinically significant to be exclusionary) and performed within 21 days of receiving the first dose of study drug. Body mass index was between 18 and 30 kg/m², inclusive. Vital signs were normal after 5 minutes resting in supine position (95 mm Hg<systolic blood pressure<140 mm Hg, 50 mm Hg<diastolic blood pressure<90 mm Hg, 45 bpm<heart rate<90 bpm). 12-Lead automatic electrocardiogram (ECG; incomplete right bundle branch block could be accepted) was normal: 120 ms<PR<210 ms, QRS<120 ms, QTc (Bazett)≦430 msec for males and ≦450 msec for females. A subject was considered to have completed the study if the subject did not experience vomiting during the first 6 hours following the administration of study drug, completed all assessments as planned, did not meet withdrawal criteria, and completed the 24-hour PK blood sample collections for all four treatment periods.

Study Drug Information and Administration:

The clinical formulations containing tianeptine hemisulfate monohydrate were once-a-day, controlled release matrix tablets consisting of hydroxypropyl methylcellulose as the rate-controlling polymer and microcrystalline cellulose as the erodible filler. Three CR tablet formulations (F1, F2, and F3, as provided in Example 6, with in vitro release profiles exhibiting 90% drug release in approximately 9, 12, and 15 hours, respectively) were employed in the study. These three formulations were equivalent in composition except for the release controlling polymers Methocel K100 LV CR Premium to Methocel K4M CR Premium ratios. All three CR formulations were white to off-white round tablets containing 25 mg of tianeptine (equivalent to 28.84 mg of tianeptine hemisulfate monohydrate). Placebo tablets were matching tablets with zero tianeptine. The STABLON® IR tablets (purchased in Austria) were two 12.5-mg white to off-white tablets (25 mg total) of the marketed product. All tianeptine hemisulfate monohydrate investigational products were stored at a temperature between 15° C. and 25° C. in an appropriate locked room under the responsibility of the investigator. The STABLON® IR tablets were stored according to the commercial packaging: Do not store above 25° C.; Protect from light.

All study drugs were taken under fasted conditions with 240 mL of non-carbonated water, between approximately 8:00 and 10:00 a.m. on Days 1, 4, 7, and 10. To maintain the blinding of the administered treatment, the subjects were asked to close their eyes and open their mouth and the two tablets (2×12.5 mg STABLON® tablets or 1×25 mg CR formulation+1 matching placebo tablet) were placed on their tongue and they were asked to swallow. Study drug was swallowed whole and not chewed, divided, dissolved, or crushed. Subjects remained in an upright position from the time of study drug administration until 4 hours after study drug administration. At approximately 2 hours after dosing (but not earlier), subjects drank 1 glass (approximately 240 mL) of water; drinking of water was allowed from then onwards. Four hours after drug intake, a standardized lunch was served on Day 1 for all subjects. The lunch was the same for all dosing days. The exact start times of lunch and dinner (9 hours post dosing) were recorded in the CRF, together with any deviation regarding the timing of lunch and dinner. Throughout the study, prescription or non-prescription medication (including vitamins and herbal supplements) other than the study drug were prohibited, except for paracetamol. The use of paracetamol was allowed until 3 days before each study drug administration. Throughout the study, a maximum of 3 doses per day of 500-mg paracetamol, and no more than 3 g per week, was allowed for the treatment of headache or other pain.

Subjects were dosed on days 1, 4, 7 and 10; a follow-up visit included day 17±2 days.

Pharmacokinetic (PK) Evaluations:

Subjects were dosed on days 1, 4, 7 and 10, and blood samples (4.5 mL each to obtain approximately 2 mL of plasma) for PK assessment were collected at days 1, 2, 4, 5, 7, 8, 10 and 11. Specifically, samples were taken before dosing (t=0) and at 0.25, 0.5, 1.0, 1.5, 2.0, 2.5, 3.0, 4.0, 6.0, 8.0, 10.0, 12.0, 14.0, 16.0, 24.0, 28.0, 32.0, and 36.0 hours after dosing on each dosing day. These samples were stored at −20° C.

Plasma samples were analyzed to determine concentrations of tianeptine, using a validated and sensitive liquid chromatography-mass spectrometry/mass spectrometry (LC-MS/MS) bioanalytical method under the supervision of ICON Development Solution (Manchester, UK). The limit of quantification (LoQ) for tianeptine was 5 ng/mL.

Data Analysis:

All available data were included in data listings.

The PK analysis set included all subjects who received at least one dose of study drug and did not have major deviations related to study drug intake. All available PK data were used. Subjects with missing data in some but not all periods were included in the analysis.

Based on the individual plasma concentration-time data, using the actual sampling times, the following PK parameters of tianeptine were estimated for each of the treatments:

$C_{max}$=observed maximum plasma concentration (ng/mL)

$T_{max}$=time to reach the observed maximum plasma concentration (h)

$T_{lag}$=Interval between time of drug administration and the time of the first analyte concentration above the limit of quantification (h)

$AUC_{24h}$=Area under the plasma concentration versus time curve calculated using the trapezoidal method over the dosing interval (24 hours; only for CR formulation) (ng.h/mL)

$AUC_{last}$=area under the plasma concentration-time curve from 0 to $t_{last}$ hours post-dosing, calculated by linear trapezoidal summation AUC$_\infty$=area under the plasma concentration-time curve from time 0 to infinite time, calculated according to the following equation AUC$_\infty$=AUC$_{last}$+C$_{last}$/$\lambda_z$ (ng.h/mL); AUC$_\infty$ was reported if t$_{1/2,\lambda}$ was assessable % AUC$_{\infty,ex}$=percentage of AUC$_\infty$ obtained by extrapolation, calculated by the following equation:

$$\frac{AUC_\infty - AUC_{last}}{AUC_\infty} * 100$$

$\lambda_z$=first-order rate constant associated with the terminal portion of the curve, determined as the negative slope of the terminal log-linear phase of the drug concentration-time curve t$_{1/2,\lambda}$=elimination half-life associated with the terminal slope ($\lambda_z$) of the semilogarithmic drug concentration-time curve, calculated as 0.693/$\lambda_z$ F$_{rel}$=relative bioavailability: the percentage of the administered dose that was systemically available, calculated as: [(AUC$_{\infty(test)}$/AUC$_{\infty(ref)}$)*(D$_{(ref)}$/D$_{(test)}$)]*100, where the reference treatment was a non-intravenous administration. Test: F1, F2, and F3 CR formulations; Reference: IR formulation.

PK parameters for tianeptine were calculated using non-compartmental analysis. Actual post-treatment blood sampling times were used in all final PK analyses. Per protocol times were used to calculate mean plasma concentrations for graphical displays. The PK analysis and descriptive statistics were performed using validated pharmacokinetics and statistical software.

C$_{max}$ and T$_{max}$ were taken directly from the data. The elimination rate constant, $\lambda_z$, was calculated as the negative of the slope of the terminal log-linear segment of the plasma concentration-time curve. The range of data used for each subject and dose were determined by visual inspection of a semilogarithmic plot of concentration vs. time. At least three data points were used to estimate $\lambda_z$. Other PK parameters were calculated as described above.

Results:

Of the 12 subjects who were enrolled, all 12 completed the study. The mean age was 37.7 years with a range of 23 to 55 years. All 12 subjects were Caucasian and half (50.0%) were male. The demographic and baseline characteristics of the 12 subjects were similar among the four treatment sequences. There were no protocol deviations that interfered with the interpretation of the study data and no subjects were excluded from analyses due to deviations.

All pre-dose samples were obtained approximately 12 to 22 minutes before study drug administration, and (relative) differences between actual and scheduled post-treatment sampling times were limited and were not considered a reason for exclusion. The elimination rate constant $\lambda_z$ and the half-life t$_{1/2,\lambda}$ were calculated only if the coefficient of determination (R$^2_{adj}$) for the estimate of the terminal elimination phase was higher than 0.80. If % AUC$_{\infty,ex}$ exceeded 20%, AUC$_\infty$ was calculated but excluded from descriptive statistics.

Figure 24:
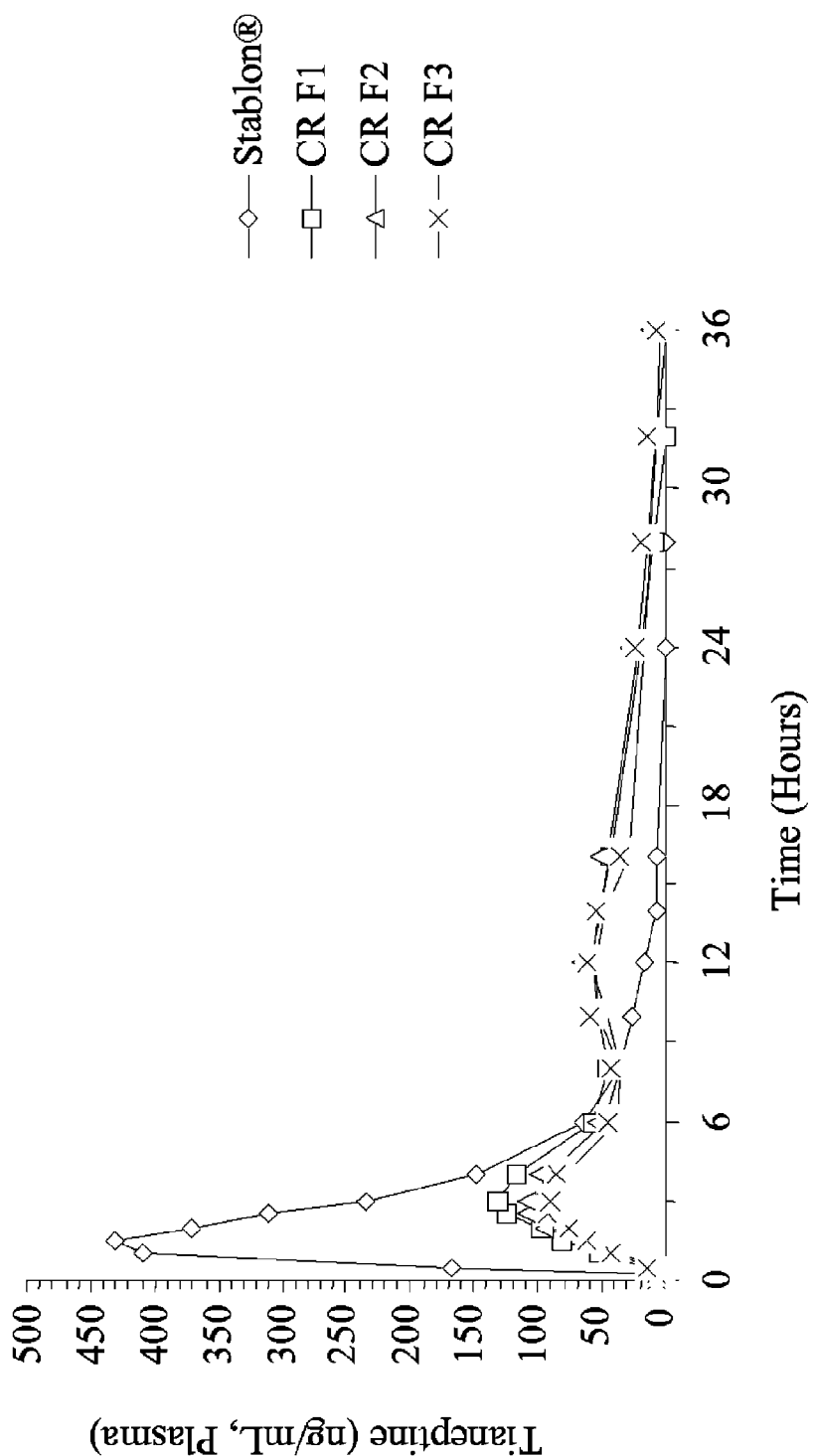

Mean plasma concentration-time profiles on the linear concentration scale for all 4 treatments are shown in FIG. 24. Table 10 below, lists the mean (±SD) pharmacokinetic parameters of tianeptine after administration of tianeptine at 25 mg as STABLON® IR tablet formulation and tianeptine hemisulfate monohydrate CR tablet formulation F1, F2, and F3, respectively.

TABLE 10

Pharmacokinetic Parameters

| Parameter | STABLON® (n = 12) | F1 (n = 12) | F2 (n = 12) | F3 (n = 11) |
|---|---|---|---|---|
| C$_{max}$, ng/mL | 464 ± 104 | 149 ± 71 | 111 ± 56 | 100 ± 41 |
| T$_{max}$, h | 1.50 (1.00-2.00) | 2.50 (1.50-4.00) | 2.51 (1.50-4.00) | 3.00 (2.00-12.0) |
| AUC$_{last}$, ng h/mL | 1535 ± 354 | 1350 ± 301 | 1290 ± 453 | 1073 ± 458 |
| AUC$_\infty$, ng h/mL | 1571 ± 382 | 1383 ± 293 | 1377 ± 442 | 1172 ± 537 |
| F$_{rel}$, % | 100 | 90.9 ± 18.0 | 89.5 ± 20.2 | 73.0 ± 26.4 |
| t$_{1/2}$, h | 3.0 ± 0.6 | 5.3 ± 0.9 | 5.7 ± 2.3 | 5.9 ± 3.6 |
| C$_{24h}$, ng/mL | BQL | 18.8 ± 8.4 | 22.3 ± 12.0 | 16.1 ± 14.7 |

C$_{max}$ = maximum plasma concentration;
T$_{max}$ = time to maximum plasma concentration;
AUC$_\infty$ = area under the plasma concentration-time curve to infinity;
AUC$_{last}$ = area under the plasma concentration-time curve from 0 to t$_{last}$ hours post-dosing;
t$_{1/2}$ = elimination half-life;
F$_{rel}$ = relative bioavailability;
BQL = below the quantification limit;
T$_{max}$: median (minimum-maximum)

The results from this study may be summarized as follows. After oral administration of the STABLON® IR tablet formulation, tianeptine was rapidly absorbed and showed a peak plasma concentration 1 to 2 hours after administration. Tianeptine plasma concentrations declined with a terminal half-life of about 3 hours.

All three tianeptine hemisulfate monohydrate CR formulations (F1, F2 and F3) showed plasma concentration levels after a lag time of 0.3 to 0.4 hours, peaking at about 2.5 to 3 hours (slightly later for F3 than for F1 and F2). For F1, maximum concentrations of tianeptine were about 3 times lower than those after the STABLON® IR formulation, whereas for F2 and F3, peak plasma concentrations of tianeptine were 4 to 5 times lower than after the STABLON®IR formulation. Plasma concentrations of tianeptine declined until about 8 hours, followed by a gradual increase to a second peak concentration observed at about 12 hours after dosing. Plasma concentrations of this second peak were in the order of 0.4 times the initial C$_{max}$ for F1 and 0.5 to 0.6 times C$_{max}$ for F2 and F3. After this second peak, plasma concentrations further declined with an estimated half-life of 5.3 hours after F1, 5.7 hours after F2, and 5.9 hours after F3 as calculated, until 36 hours after administration. Average 24-hour concentrations were 0.13 times the C$_{max}$ after F1, 0.20 times C$_{max}$ after F2, and 0.16 times C$_{max}$ after F3, predicting the most limited peak to trough ratio after QD repeated administration for F2. The relative bioavailability of tianeptine as compared with the STABLON® IR formulation was 91% for F1, 90% for F2, and 73% for F3. Inter-individual variability in exposure of tianeptine as expressed in % CV tended to increase from CR formulation F1 to F2 to F3.

STABLON® IR tablet formulation showed PK characteristics consistent with what is known in the literature: it was rapidly absorbed, showed a peak plasma concentration at 1 to 2 hours after administration, and declined with a half-life of about 3 hours.

Tianeptine hemisulfate monohydrate CR formulations (F1, F2 and F3) showed peak plasma concentrations that were much lower than after the STABLON® IR formulation at median time of about 2.5 to 3 hours (slightly later for F3 than for F1 and F2) after administration. Peak concentrations of tianeptine were higher for the F1 CR formulation than for F2 and F3 CR formulations. After the C$_{max}$, absorption of tianeptine from the CR formulations (F1, F2 and F3) continued, resulting in a second peak around 10 to 16 hours after administration. Differences between first and second peak were larger for F1 (second peak in the order of 0.4 times the $C_{max}$) than for F2 and F3 (second peak 0.5 to 0.6 times $C_{max}$). Plasma concentrations declined with a half-life of 5 to 6 hours. Differences between $C_{24\,h}$ and $C_{max}$ were larger for F1 and F3 ($C_{24\,h}/C_{max}$ ratios 0.13 and 0.16, respectively) than for F2 ($C_{24\,h}/C_{max}$ ratio 0.20), which predicts the smallest peak/trough ratio for F2 after repeated administration. CR formulation F2 showed the most limited peak/trough ratio as well as a high bioavailability.

In conclusion, the tianeptine hemisulfate monohydrate CR formulations (F1, F2 and F3) showed a more gradual absorption as demonstrated by a later peak time, lower $C_{max}$, and a more gradual decline than occurred after administration of the STABLON® IR formulation. In contrast with the STABLON® IR formulation, after the first $C_{max}$, absorption of tianeptine from the CR formulations continued, resulting in a second peak around 10 to 16 hours after administration.

What is claimed is:

1. 7-[(3-chloro-6,11-dihydro-6-methyldibenzo[c,f][1,2]thiazepin-11-yl)amino]heptanoic acid S,S-dioxide hemisulfate monohydrate, represented by formula (II):

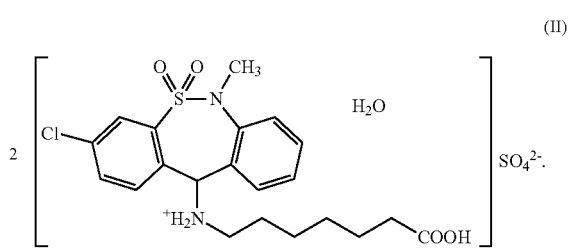

2. The 7-[(3-chloro-6,11-dihydro-6-methyldibenzo[c,f][1,2]thiazepin-11-yl)amino]heptanoic acid S,S-dioxide hemisulfate monohydrate of claim 1, in crystalline form.

3. The 7-[(3-chloro-6,11-dihydro-6-methyldibenzo[c,f][1,2]thiazepin-11-yl)amino]heptanoic acid S,S-dioxide hemisulfate monohydrate of claim 1, wherein said hemisulfate monohydrate is present, in at least a detectable amount, as crystalline 7-[(3-chloro-6,11-dihydro-6-methyldibenzo[c,f][1,2]thiazepin-11-yl)amino]heptanoic acid S,S-dioxide hemisulfate monohydrate.

4. The 7-[(3-chloro-6,11-dihydro-6-methyldibenzo[c,f][1,2]thiazepin-11-yl)amino]heptanoic acid S,S-dioxide hemisulfate monohydrate of claim 3, wherein said crystalline hemisulfate monohydrate is present in an amount of about 20% to about 100% by weight of said hemisulfate monohydrate.

5. The 7-[(3-chloro-6,11-dihydro-6-methyldibenzo[c,f][1,2]thiazepin-11-yl)amino]heptanoic acid S,S-dioxide hemisulfate monohydrate of claim 1, wherein said hemisulfate monohydrate is characterized by an X-ray powder diffractogram comprising a peak at about 8.97 degrees 2-theta.

6. The 7-[(3-chloro-6,11-dihydro-6-methyldibenzo[c,f][1,2]thiazepin-11-yl)amino]heptanoic acid S,S-dioxide hemisulfate monohydrate of claim 1, wherein said hemisulfate monohydrate is characterized by an X-ray powder diffractogram comprising a peak at about 11.49 degrees 2-theta.

7. The 7-[(3-chloro-6,11-dihydro-6-methyldibenzo[c,f][1,2]thiazepin-11-yl)amino]heptanoic acid S,S-dioxide hemisulfate monohydrate of claim 1, wherein said hemisulfate monohydrate is characterized by an X-ray powder diffractogram comprising peaks at about 8.25 and about 8.97 degrees 2-theta.

8. The 7-[(3-chloro-6,11-dihydro-6-methyldibenzo[c,f][1,2]thiazepin-11-yl)amino]heptanoic acid S,S-dioxide hemisulfate monohydrate of claim 1, wherein said hemisulfate monohydrate is characterized by an X-ray powder diffractogram comprising peaks at about 8.25, about 13.91 and about 14.73 degrees 2-theta.

9. The 7-[(3-chloro-6,11-dihydro-6-methyldibenzo[c,f][1,2]thiazepin-11-yl)amino]heptanoic acid S,S-dioxide hemisulfate monohydrate of claim 1, wherein said hemisulfate monohydrate is characterized by an X-ray powder diffractogram comprising peaks at about 8.97, about 18.07, about 19.39 and about 20.59 degrees 2-theta.

10. The 7-[(3-chloro-6,11-dihydro-6-methyldibenzo[c,f][1,2]thiazepin-11-yl)amino]heptanoic acid S,S-dioxide hemisulfate monohydrate of claim 1, wherein said hemisulfate monohydrate is characterized by an X-ray powder diffractogram comprising peaks at about 8.97, about 11.49, about 13.91, about 18.07, about 19.39 and about 20.59 degrees 2-theta.

11. The 7-[(3-chloro-6,11-dihydro-6-methyldibenzo[c,f][1,2]thiazepin-11-yl)amino]heptanoic acid S,S-dioxide hemisulfate monohydrate of claim 1, wherein said hemisulfate monohydrate is characterized by an X-ray powder diffractogram comprising peaks at about 8.25, about 8.97, about 11.49, about 13.91, about 14.73, about 16.95, about 18.07, about 19.39, about 20.59, about 21.99, about 22.83 and about 23.27 degrees 2-theta.

12. The 7-[(3-chloro-6,11-dihydro-6-methyldibenzo[c,f][1,2]thiazepin-11-yl)amino]heptanoic acid S,S-dioxide hemisulfate monohydrate of claim 1, wherein said hemisulfate monohydrate is characterized by an X-ray powder diffractogram substantially as shown in FIG. 1.

13. The 7-[(3-chloro-6,11-dihydro-6-methyldibenzo[c,f][1,2]thiazepin-11-yl)amino]heptanoic acid S,S-dioxide hemisulfate monohydrate of claim 1, wherein said hemisulfate monohydrate is characterized by a differential scanning calorimetry thermogram comprising an endothermic transition at about 193° C.

14. The 7-[(3-chloro-6,11-dihydro-6-methyldibenzo[c,f][1,2]thiazepin-11-yl)amino]heptanoic acid S,S-dioxide hemisulfate monohydrate of claim 1, wherein said hemisulfate monohydrate is nonhygroscopic from about 10% to about 90% relative humidity as measured at 25° C. by dynamic vapor sorption.

15. The 7-[(3-chloro-6,11-dihydro-6-methyldibenzo[c,f][1,2]thiazepin-11-yl)amino]heptanoic acid S,S-dioxide hemisulfate monohydrate of claim 1, wherein the ratio of 7-[(3-chloro-6,11-dihydro-6-methyldibenzo[c,f][1,2]thiazepin-11-yl)amino]heptanoic acid S,S-dioxide to sulfuric acid to water is about 2:1:2.

16. Crystalline 7-[(3-chloro-6,11-dihydro-6-methyldibenzo[c,f][1,2]thiazepin-11-yl)amino]heptanoic acid S,S-dioxide hemisulfate monohydrate, characterized by an X-ray powder diffractogram comprising peaks at about 8.97, about 11.49, about 14.73, about 20.59, about 22.83 and about 23.27 degrees 2-theta.

17. A method of making 7-[(3-chloro-6,11-dihydro-6-methyldibenzo[c,f][1,2]thiazepin-11-yl)amino]heptanoic acid S,S-dioxide hemisulfate monohydrate of formula (II):

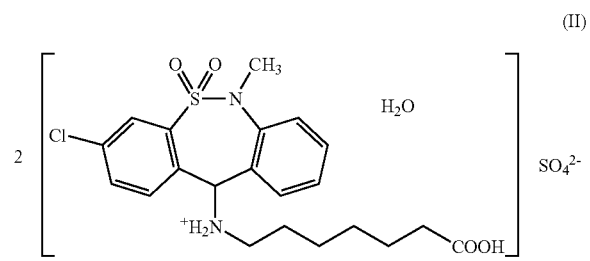

(II)

comprising the steps of:
(a) dissolving 7-[(3-chloro-6,11-dihydro-6-methyldibenzo[c,f][1,2]thiazepin-11-yl)amino]heptanoic acid S,S-dioxide or the sodium salt thereof in a mixture of water and acetic acid;
(b) adding a solution of sulfuric acid in a solvent comprising water alone or in combination with acetic acid to the reaction mixture of step (a); and
(c) crystallizing the compound of formula (II).

18. The method of claim 17, further comprising the steps of:
(d) isolating the compound of formula (II) obtained in step (c) from the reaction mixture;
(e) washing the compound of formula (II) with a mixture of water and acetic acid;
(f) further washing the compound of formula (II) with water; and
(g) drying the compound of formula (II).

19. The method of claim 17, wherein the method is carried out without isolating an intermediate of the following formula:

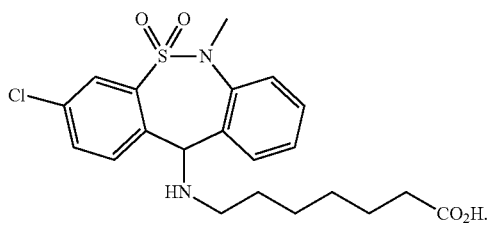

20. A method of treating a mammal suffering from depression, comprising administering to said mammal an effective amount of the 7-[(3-chloro-6,11-dihydro-6-methyldibenzo[c,f][1,2]thiazepin-11-yl)amino]heptanoic acid S,S-dioxide hemisulfate monohydrate of claim 1.

21. A pharmaceutical composition comprising the 7-[(3-chloro-6,11-dihydro-6-methyldibenzo[c,f][1,2]thiazepin-11-yl)amino]heptanoic acid S,S-dioxide hemisulfate monohydrate of claim 1 and a pharmaceutically acceptable carrier.

22. The composition of claim 21, wherein said pharmaceutical composition is a controlled release pharmaceutical composition.

23. A controlled release matrix tablet comprising:
a pharmaceutically effective amount of 7-[(3-chloro-6,11-dihydro-6-methyldibenzo[c,f][1,2]thiazepin-11-yl)amino]heptanoic acid S,S-dioxide hemisulfate monohydrate; and
one or more release controlling polymers,
wherein the tablet, when orally administered to a patient, provides a mean maximum plasma concentration ($C_{max}$) of 7-[(3-chloro-6,11-dihydro-6-methyldibenzo[c,f][1,2]thiazepin-11-yl)amino]heptanoic acid S,S-dioxide from about 100 ng/mL to about 150 ng/mL.

24. The tablet of claim 23, wherein said tablet has a dissolution rate in vitro, when measured using a USP dissolution apparatus, type II (paddle) at 100 rpm in 900 mL simulated gastric fluid (pH about 1.2) at about 37° C., of less than 14% 7-[(3-chloro-6,11-dihydro-6-methyldibenzo[c,f][1,2]thiazepin-11-yl)amino]heptanoic acid S,S-dioxide hemisulfate monohydrate released after 1 hour, between 45% and 80% 7-[(3-chloro-6,11-dihydro-6-methyldibenzo[c,f][1,2]thiazepin-11-yl)amino]heptanoic acid S,S-dioxide hemisulfate monohydrate released after 7 hours, and greater than 90% 7-[(3-chloro-6,11-dihydro-6-methyldibenzo[c,f][1,2]thiazepin-11-yl)amino]heptanoic acid S,S-dioxide hemisulfate monohydrate released after 16 hours, by weight.

25. The tablet of claim 23, wherein said tablet, when orally administered to a patient, provides a mean maximum plasma concentration ($C_{max}$) of 7-[(3-chloro-6,11-dihydro-6-methyldibenzo[c,f][1,2]thiazepin-11-yl)amino]heptanoic acid S,S-dioxide from about 100 ng/mL to about 120 ng/mL.

26. The tablet of claim 23, wherein said tablet, when orally administered to a patient, provides a median time to mean maximum plasma concentration ($T_{max}$) of 7-[(3-chloro-6,11-dihydro-6-methyldibenzo[c,f][1,2]thiazepin-11-yl)amino]heptanoic acid S,S-dioxide ranging from about 2.5 hours to about 3.0 hours.

27. The tablet of claim 23, wherein said tablet, when orally administered to a patient, provides a plasma concentration time curve with a mean area under the curve ranging from about 1170 ng.hr/mL to about 1380 ng.hr/mL.

28. The tablet of claim 23, wherein said one or more release controlling polymers comprises hydroxypropyl methylcellulose.

29. The tablet of claim 23, wherein said one or more release controlling polymers comprises a first hydroxypropyl methylcellulose having a viscosity of 80 to 120 cps (2% solution in water) and a second hydroxypropyl methylcellulose having a viscosity of 3,000 to 5,600 cps (2% solution in water).

30. The tablet of claim 29, wherein said first hydroxypropyl methylcellulose and said second hydroxypropyl methylcellulose are present in a ratio of about 2:1 to about 4:1.

* * * * *